(12) United States Patent
Allawi et al.

(10) Patent No.: US 9,096,893 B2
(45) Date of Patent: Aug. 4, 2015

(54) METHODS FOR ANALYSIS OF NUCLEIC ACID MOLECULES DURING AMPLIFICATION REACTIONS

(71) Applicant: Hologic, Inc., Marlborough, MA (US)

(72) Inventors: Hatim T. Allawi, Middleton, WI (US); Victor I. Lyamichev, Madison, WI (US)

(73) Assignee: HOLOGIC, INC., Bedford, MA (US)

( * ) Notice: Subject to any disclaimer, the term of this patent is extended or adjusted under 35 U.S.C. 154(b) by 27 days.

(21) Appl. No.: 13/941,122

(22) Filed: Jul. 12, 2013

(65) Prior Publication Data

US 2014/0057259 A1   Feb. 27, 2014

Related U.S. Application Data

(62) Division of application No. 12/404,240, filed on Mar. 13, 2009, now abandoned.

(60) Provisional application No. 61/036,953, filed on Mar. 15, 2008.

(51) Int. Cl.
*C12Q 1/68* (2006.01)

(52) U.S. Cl.
CPC ............ *C12Q 1/6832* (2013.01); *C12Q 1/6823* (2013.01); *C12Q 1/6827* (2013.01); *C12Q 1/6851* (2013.01)

(58) Field of Classification Search
CPC .......... C12Q 2525/161; C12Q 1/6823; C12Q 2537/149; C12Q 2561/109; C12Q 2561/113; C12Q 2565/1015; C12Q 1/6827; C12Q 1/6851; C12Q 2521/313; C12Q 2531/113; C12Q 1/6832
See application file for complete search history.

(56) References Cited

U.S. PATENT DOCUMENTS

| | | |
|---|---|---|
| 6,759,226 B1 | 7/2004 | Ma |
| 6,767,723 B2 | 7/2004 | Tonoike |
| 6,767,724 B2 | 7/2004 | Lee |
| 6,780,585 B1 | 8/2004 | Dong |
| 6,780,982 B2 | 8/2004 | Lyamichev |
| 6,783,940 B2 | 8/2004 | McLaughlin |

(Continued)

FOREIGN PATENT DOCUMENTS

| | | |
|---|---|---|
| WO | WO89/09284 | 10/1989 |
| WO | WO90/01069 | 2/1990 |

(Continued)

OTHER PUBLICATIONS

Affidavit of Erick Ottoson, Declaration and Exhibit A, Oct. 25, 2005, 04-C-0680-C.

(Continued)

*Primary Examiner* — Teresa E Strzelecka
(74) *Attorney, Agent, or Firm* — Casimir Jones S.C.

(57) ABSTRACT

The present invention provides systems, methods and kits for performing a detection assay (e.g., invasive cleavage assay) in combination with an amplification assay (e.g., PCR), where the detection assay employs enzyme footprint probes with relatively short (e.g., 6-12 bases) analyte-specific regions configured to provide a preferred footprint length of duplex for use with a particular nucleic acid modifying enzyme. In some embodiments, such assays are used for target quantification, and in other embodiments, such assays are used for genotyping. In certain embodiments, the use of such short probes allows for assays with increased dynamic range.

21 Claims, 33 Drawing Sheets

(56) References Cited

U.S. PATENT DOCUMENTS

| | | |
|---|---|---|
| 6,790,645 B2 | 9/2004 | Brzostowicz |
| 6,814,935 B2 | 11/2004 | Harms |
| 6,855,553 B1 | 2/2005 | Bedingham |
| 6,872,816 B1 | 3/2005 | Hall |
| 6,875,572 B2 | 4/2005 | Prudent |
| 6,893,819 B1 | 5/2005 | Sorge |
| 6,913,881 B1 | 7/2005 | Aizenstein |
| 6,932,110 B2 | 8/2005 | Mijers |
| 6,932,943 B1 | 8/2005 | Cracauer |
| 6,962,780 B2 | 11/2005 | Nakayama |
| 7,011,944 B2 | 3/2006 | Prudent |
| 7,026,168 B2 | 4/2006 | Bedingham |
| 7,045,289 B2 | 5/2006 | Allawi |
| 7,060,436 B2 | 6/2006 | Lyamichev |
| 7,067,643 B2 | 6/2006 | Dahlberg |
| 7,087,381 B2 | 8/2006 | Dahlberg |
| 7,101,672 B2 | 9/2006 | Dong |
| 7,118,860 B2 | 10/2006 | Sorge |
| 7,122,364 B1 | 10/2006 | Lyamichev |
| 7,150,982 B2 | 12/2006 | Allawi |
| 7,157,621 B2 | 1/2007 | Allen |
| 7,195,871 B2 | 3/2007 | Lyamichev |
| 7,256,020 B2 | 8/2007 | Lyamichev |
| 7,273,696 B2 | 9/2007 | Dahlberg |
| 7,276,597 B2 | 10/2007 | Sorge |
| 7,297,780 B2 | 11/2007 | Skrzypczynski |
| 7,303,869 B2 | 12/2007 | Stevens |
| 7,306,917 B2 | 12/2007 | Prudent |
| 7,309,573 B2 | 12/2007 | Sorge |
| 7,312,033 B2 | 12/2007 | Accola |
| 7,354,708 B2 | 4/2008 | Hall |
| 7,381,530 B2 | 6/2008 | Hall |
| 7,381,532 B2 | 6/2008 | Sorge |
| 7,384,746 B2 | 6/2008 | Lyamichev |
| 7,407,782 B2 | 8/2008 | Prudent |
| 7,432,048 B2 | 10/2008 | Neri |
| 7,435,390 B2 | 10/2008 | Cracauer |
| 7,462,451 B2 | 12/2008 | Skrzypczynski |
| 7,473,773 B2 | 1/2009 | Elagin |
| 7,482,118 B2 | 1/2009 | Allawi |
| 7,482,121 B2 | 1/2009 | Sorge |
| 7,482,127 B2 | 1/2009 | Agarwal |
| 7,527,928 B2 | 5/2009 | Neri |
| 7,527,948 B2 | 5/2009 | Hudson |
| 2004/0214174 A1* | 10/2004 | Neri et al. ............ 435/6 |
| 2006/0147955 A1* | 7/2006 | Allawi et al. ............ 435/6 |

FOREIGN PATENT DOCUMENTS

| | | |
|---|---|---|
| WO | WO90/15157 | 12/1990 |
| WO | WO91/09950 | 11/1991 |
| WO | WO92/06200 | 4/1992 |
| WO | WO92/02638 | 12/1992 |
| WO | WO94/29482 | 12/1994 |
| WO | WO95/14106 | 5/1995 |
| WO | WO96/20287 | 7/1996 |
| WO | WO96/40999 | 12/1996 |
| WO | WO97/27214 | 7/1997 |
| WO | WO98/23774 | 6/1998 |
| WO | WO98/42873 | 10/1998 |
| WO | WO98/50403 | 11/1998 |
| WO | WO99/67641 | 12/1999 |
| WO | WO00/39587 | 7/2000 |
| WO | WO01/32922 | 5/2001 |
| WO | WO01/57256 | 8/2001 |
| WO | WO01/88190 | 11/2001 |
| WO | WO01/90337 | 11/2001 |
| WO | WO01/98537 | 12/2001 |
| WO | WO02/00934 | 1/2002 |
| WO | WO02/070755 | 9/2002 |
| WO | WO02/090572 | 11/2002 |

OTHER PUBLICATIONS

Amended Answer and Counterclaims, Dec. 30, 2004, 04-C-0680-C.
Answer by Plaintiff to Counterclaims, Jan. 19, 2005 04-C-0680-C.
Answer to Counterclaim, Oct. 11, 2005, 1:05-cv-00275.
Answer, Oct. 20, 2004, 04-C-0680-C.
Answer, Affirmative Defenses and Counterclaim, filed Oct. 7, 2002, 02-C-0507-C.
Answer, Sep. 21, 2005, 1:05-cv-00275.
Brief for Defendant-Appellant Stratagene Corp., Filed May 12, 2006, 04-CV-0680.
Brief for Plaintiff-Appellee Third Wave Technologies, filed Jun. 26, 2006, 04-C-0680-C.
Brief in Opposition to Deft. Motion for Judgment as a Matter of Law, Oct. 26, 2005, 04-C-0680-C.
Brief in Opposition to Stratagene's Rule 59 Motion, Oct. 25, 2005, 04-C-0680-C.
Brief in Reply in Support of Deft. Motion for a New Trial Based on Evidentiary Issues, Nov. 1, 2005, 04-C-0680-C.
Brief in Reply in Support of Deft. Motion for Judgment as a Matter of Law, or Alternatively, a New Trial on Liability, Nov. 1, 2005, 04-C-0680-C.
Brief in Support of Deft. Motion for Judgment as a Matter of Law, or Alternatively, a New Trial on Liability, Oct. 4, 2005, 04-C-0680-C.
Brief on Deft. Motion for a New Trial Based on Evidentiary Issues, Oct. 4, 2005, 04-C-0680-C.
Complaint, May 6, 2005 (Including Exhibits A and B), 1:05-cv-00275.
Complaint, Sep. 15, 2004, 04-C-0680-C.
Complaint, Aug. 30, 2000, 00-C-5353.
Complaint, filed Sep. 6, 2002, 02-C-0507-C.
Court Daily Transcripts, Aug. 23, 2005 to Sep. 2, 2005, 04-C-0680--C.
Defendant's Amended Responses to TWT's Expedited Third Set of Interrogatories (Nos. 15-16), Mar. 28, 2003, 02-C-0507-C.
Defendant's Brief in Opposition to Plaintiff's Motion to Strike Eragen's Affirmative Defenses and Counterclaim of Invalidity, Nov. 15, 2002, 02-C-0507-C.
Defendant's Responses to TWT's Expedited Third Set of Interrogatories (Nos. 15-16), Jan. 27, 2003, 02-C-0507-C.
Defendant's Rule 26(a)(1) Disclosures; Nov. 4, 2002, 02-C-0507-C.
Defendant's Surreply in Opposition to Plaintiff's Motion to Strike Eragen's Affirmative Defenses and Counterclaim of Invalidity, Nov. 27, 2002, 02-C-0507-C.
Defendant's Trial Exhibit 1315, 04-C-0680-C.
Defendant's Trial Exhibit 1316, 04-C-0680-C.
Docket Sheet for Civil Case No. 00-C-0494-S (W.D. Wis.), filed Aug. 10, 2000.
Docket Sheet for Civil Case No. 04-C-0680-C (W.D. Wis), filed Sep. 15, 2004.
Docket Sheet for Civil Case No. 04-C-0680-C (W.D.Wis), filed Sep. 15, 2004.
Docket Sheet for Civil Case No. 3:2002cv00507-C (W.D.Wis), filed Sep. 6, 2002, closed on Apr. 14, 2003.
Docket Sheet for Civil Case No. 1:00-cv-05353 (N.D. Ill.), filed Aug. 30, 2000.
Docket Sheet for Civil Case No. 1:05-cv-00275 (DE), filed May 6, 2005.
Listing of Briefs for Appeal Case No. 2006-1209.
Opinion and Order dated Aug. 4, 2005, 04-C-680-C.
Opinion and Order dated Dec. 16, 2005, 04-C-0680-C.
Order Granting Pitt Motion to Establish Subject Matter Jurisdiction, Sep. 2, 2005, 04-C-0680-C.
Order Granting Plaintiff Enhanced Damages in the Amount of $15,870,000 with Atty Fees, Dec. 16, 2005, 04-C-0680-C.
Order on Claims Construction Hearing, Mar. 18, 2003, 02-C-507-C.
Order Ruling on Construction of Claims and Motion for Summary Judgement, 04-C-680-C-8-05-05, Aug. 5, 2005, 04-C-0680-C.
Plaintiff's Amended Response to Defendant's First Set of Interrogatories to Third Wave Technologies, Inc., Dec. 3, 2002, 02-C-0507-C.
Plaintiff's Response to Defendant's First Set of Interrogatories to Third Wave Technologies, Inc., Nov. 21, 2002, 02-C-0507-C.
Reply Brief for Defendant-Appellant Stratagene Corp., Filed Jul. 10, 2006, 04-CV-0680.

(56) References Cited

OTHER PUBLICATIONS

Third Wave Technologies' Motion to Strike Eragen's Affirmative Defenses and Counterclaim of Invalidity, Oct. 28, 2002, 02-C-0507-C.
Third Wave Technologies' Reply in Support of Its Motion to Strike Eragen's Affirmative Defenses and Counterclaim of Invalidity, Nov. 25, 2002, 02-C-0507-C.
Third Wave Technologies' Reply to Defendant Eragen's Counterclaim, Oct. 28, 2002, 02-C-0507-C.
Williams, et al, "Laser Temperature-Jump, Spectroscopic, and Thermodynamic Study of Salt Effects on Duplex Formation by dGCATGC" Biochemistry; 28:4283-429 [1989].
Wu, et al. "The Ligation Amplification Reaction (LAR)—Amplification of Specific DNA Sequences Using Sequential Rounds of Template-Dependent Ligation," Genomics 4:560-569 (1989).
Wu, et al., "Processing of branched DNA intermediates by a complex of human FEN-1 and PCNA," Nucleic Acids Research 24:2036-2043 (1996).
Xu, et al., "Biochemical and Mutational Studies of the 5'-3' Exonuclease of DNA Polymerase 1 of *Escherichia coli*," J. Mol. Biol. 268:284-302 (1997).
Youil, et al., "Screening for Mutations by Enzyme Mismatch Cleavage with T4 Endonuclease VII," Proc. Natl. Acad. Sci. USA 92:87-91 (1995).
Young, et al. (1985) in Nucleic Acid Hybridisation: A Practical Approach (Hames & Higgins, Eds.) pp. 47-71, IRL Press, Oxford.
Zarlenga, et al. "PCR as a diagnostic and quantitative technique in veterinary parasitology" Vet Parasitol. 101: 215 (2001).
Zuker "On Finding All Suboptimal Foldings of an RNA Molecule" Science, 244:48 (1989).
Zwickl, et al. "Glyceraldehyde-3-Phosphate Dehydrogenase from the Hyperthermophilic Archaebacterium *Pyrococcus woesei*: Characterization of the Enzyme, Cloning and Sequencing of the Gene, and Expression in *Escherichia coli*," J. Bact. 172:4329-4338 (1990).
Mercier, et al. "Direct PCR from whole blood, without DNA extraction" Nucl. Acids Res. 18 (19): 5908 (1990).
Mhlanga, et al. "Using molecular beacons to detect single-nucleotide polymorphisms with real-time PCR" 2001 Methods 25, 463-471.
Milligan, et al. "Synthesis of Small RNAs Using T7 RNA Polymerase," Methods Enzymol. 180:51 (1989).
Milligan, et al., "Oligoribonucleotide synthesis using T7 RNA polymerase and synthetic DNA templates," Nucl. Acids. Res. 15(21): 8783-8789 (1987).
Morris, et al. Rapid reverse transcription-PCR detection of hepatitis C virus RNA in serum by using the TaqMan fluorogenic detection system J Clin Microbiol. Dec. 1996; 34(12):2933-6.
Moss "RNA interference: It's a small RNA world" Current Biology, 2001, pp. R772-R775, vol. 11.
Moss "MicroRNAs: hidden in the genome" (2002) Curr. Biol. vol. 12, pp. R138-R140.
Mullis "The Polymerase Chain Reaction in an Anemic Mode: How to Avoid Cold Oligodeoxyribonuclear Fusion," PCR Methods Applic., 1:1-4 (1991).
Mullis, et al. "Specific Synthesis of DNA in Vitro via a Polymerase-Catalyzed Chain Reaction" Methods Enzymol; 155:335-350. (1987).
Murante, et al. "The Calf 5'- to 3'-Exonuclease Is Also an Endonuclease with Both Activities Dependent on Primers Annealed Upstream of the Point of Cleavage" J. Biol. Chem. 269:1191-1196 (1994).
Murante, et al., "Calf 5' to 3' Exo/Endonuclease Must Slide from a 5' End of the Substrate to Perform Structure-specific Cleavage," J. Biol. Chem. 270:30377-30383 (1995).
Murray, et al., "Structural and Functional Conversation of the Human Homolog of the *Schizosaccharomyces pombe* rad2 gene, Which is Required for Chromosome Segregation and Recovery from DNA Damage," Molecular and Cellular Biology 14:4878-4888 (1994).
Myers, et al., "Reverse Transcription and DNA amplification by a *Thermus thermophilus* DNA Polymerase," Biochem. 30:7661-7666 (1991).

Neri, et al. "Transferring Automation for Large-scale Development and Production of InvaderTM SNP Assays" Progress in Biomedical Optics 1:117-125 (2000).
Newlin, et al. "The Invader Assay: An Alternative to PCR-Based Testing for the Detection of Point Mutations Associated With Venous Thrombosis" Clinical Hemostasis Review, 14:10-12 (2000).
Nielsen, et al. "Sequence-selective recognition of DNA by strand displacement with a thymine-substituted polyamide" Science 254:1497-1500 (1991).
Nielsen, et al., "Peptide nucleic acids (PNAs): Potential anti-sense and anti-gene agents," Anticancer Drug Des. 8:53 63 (1993).
Nishimura, et al., "Direct polymerase chain reaction from whole blood without DNA isolation" Ann. Clin Biochem, 37:674-80[2000].
Nishimura, et al., "Various Applications of Direct PCR Using Blood Samples" Clin. Lab., 48:377-84 [2002].
Nolan, et al. "Kinetic Analysis of Human Flap Endonuclease-1 by Flow Cytometry," Biochemistry 35:11668-11677 (1996).
Notomi, et al. "Loop-mediated isothermal amplification of DNA," Nucleic Acids Research, 2000, vol. 28, No. 12, e63, pp. 1-7.
Nugent, et al. "Characterization of the Apurinic Endonuclease Activity of *Drosophila* Rrp1," Biochemistry 32:11445-11452 (1993).
Odelberg, et al. "Template-switching during DNA synthesis by *Thermus aquaticus* DNA polymerase I" Nucleic Acids Res. 23(11): 2049-57 (1995).
Ohnishi "A high-throughput SNP typing system for genome-wide association studies" J Hum Genet: 46:470-477 (2001).
Oliphant "BeadArray Technology: Enabling an Accurate, Cost-Effective Approach to High-Throughput Genotyping" Biotechniques: Suppl: 56-61 (2002).
Olivier "The Invader assay for SNP genotyping" 2005 Mutat Res 573, 103-110.
Reynaldo, et al. "The Kinetics of Oligonucleotide Replacements" J. Mol Biol; 297: 511-520 (2000).
Reagan, et al. "Characterization of a Mutant Strain of *Saccharomyces cerevisiae* with a Deletion of the RAD27 Gene, a Structural Homolog of the RAD2 Nucleotide Excision Repair Gene" J. of Bacteriology 177:364-371 (1995).
Rao, et al. "*Methanococcus jannaschii* Flap Endonuclease: Expression, Purification, and Substrate Requirements" J. of Bacteriology 180:5406-5412 (1998).
Pontius, et al. "Rapid renaturation of complementary DNA strands mediated by cationic detergents: A role for high-probability binding domains in enhancing the kinetics of molecular assembly processes," Proc. Natl. Acad. Sci. USA 88:8237-8241 (1991).
Polz, et al. "Bias in Template-to-Product Ratios in Multitemplate PCR" Applied and Environmental Microbiology, 64: 3724 (1998).
Pillai, et al. "Inhibition of translational initiation by Let-7 MicroRNA in human cells" Science 309, 1573-1576 (2005).
Orpana "Fluorescence resonance energy transfer (FRET) using ssDNA binding fluorescent dye" 2004 Biomol Eng 21, 45-50.
Ostermayer "Preparation and properties of infrared-to-visible conversion phosphors" Metall. Trans. 752, 747-755 (1971).
Ouhibi, et al. "Preimplantation Genetic Diagnosis" Curr Womens Health Rep. 1: 138 (2001).
Ozaki, et ai, "Functional SNPs in the lymphotoxin-a gene that are associated with susceptibility to myocardial infarction" Nat Genet; 32: 650-654 [2002].
Palissa, et al. "Reduktion geschützter 2'-Chlor-2'-desoxydinucleotide mit Tri-n-butylzinnhydrid" Z. Chem., 27:216 (1987).
Pasquinelli, et al. "Conservation of the sequence and temporal expression of let-7 heterochronic regulatory RNA" (2000) Nature 408:86-9.
Patel, et al. "Formation of chimeric DNA primer extension products by template switching onto an annealed downstream oligonucleotide" Proc Natl Acad Sci U S A. Apr. 2, 1996;93(7):2969-74.
Paul, et al. "Effective expression of small interfering RNA in human cells" Nature Biotechnology 20: 505-508 (2002).
Perler, et al. "Intervening sequences in an *Archaea* DNA polymerase gene" Proc. Natl. Acad. Sci. USA 89:5577-5581 (1992).

\* cited by examiner

FIGURE 2A

```
                                    (SEQ ID NO:144)
10-nt probe    3'-HEX-CATCCAACAT GAGGCGCAG         Tm of 10-nt analyte-specific portion: 34.2°C
                                    (SEQ ID NO:141)
11-nt probe    3'-HEX-CATCCAACATA GAGGCGCAG        Tm of 11-nt analyte-specific portion: 36.2°C 5'-CCAGTGCCGATGAGGTAGTAGGTTGTATAGTTCGCTGGACCGTG-3'   (SEQ ID NO:142) let-7a RT-Product
                                         Let-7a Target (SEQ ID NO:143)  3'-ATCAAGCGACCTGGCAC INVADER oligonucleotide for 11-nt probe (SEQ ID NO:145) 3'-TATCAAGCGACCTGGCAC INVADER oligonucleotide for 10-nt probe
```

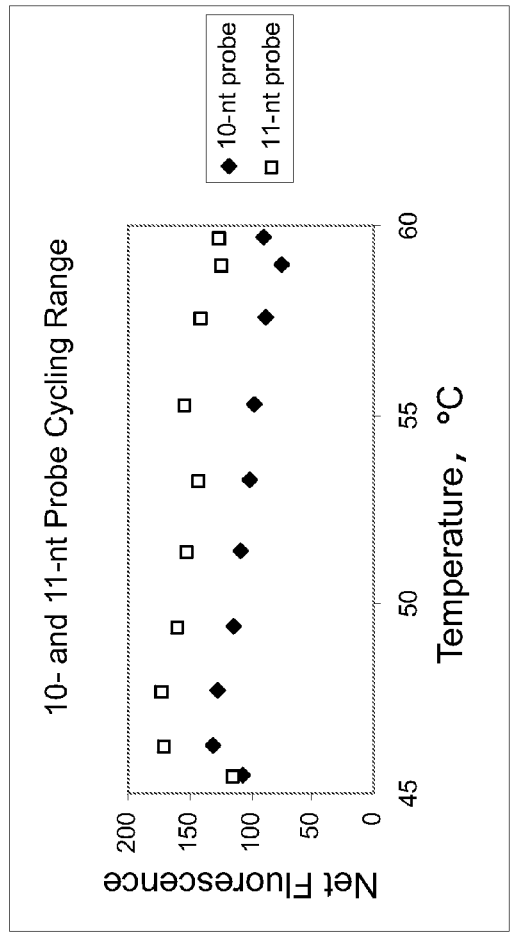

(SEQ ID NO:146)   9-nt probe

5'-GACGCGGAG TGGGCCACC-NH2-3'   Tm of 9-nt analyte-
specific portion: 45.6°C (SEQ ID NO:147)                                                    (SEQ ID NO:148)

INVADER oligonucleotide 5'-AGACARAGCGGGTCCATCCCY

Vzv Target 5'-ACGTACACGTGATACTGAGACAAAGCGGGTCCATCCCTGGCCACCTCTCGAGGCCACCGCGTCCAACACCAGCA

FIGURE 3

| TARGET | COMPLETE PROBE SEQUENCE (5' to 3'; All Probe Have 3' HEX) | SEQ ID NO: | 5'-flap name | ANALYTE-SPECIFIC REGION (5' to 3') | SEQ ID NO: | LENGTH OF ASR | Tm |
|---|---|---|---|---|---|---|---|
| microRNA | | | | | | | |
| Let-7a | GACGCGGAGTACAACCTACT | 52 | Arm 3 | TACAACCTACT | 53 | 11 | 36.8 |
| Let-7b | CCACGCGACCACAACCTACT | 54 | Arm 4 | CACAACCTACT | 55 | 11 | 40.5 |
| miR-9 | GACGCGGAGTATCTAGCTGTA | 56 | Arm 3 | TATCTAGCTGTA | 57 | 12 | 38.4 |
| miR-15a | CCACGCGACGACCATTAGTGC | 58 | Arm 4 | ACCATTAGTGC | 59 | 12 | 44.9 |
| miR-15b | GACGCGGAGACCATCATGTGC | 60 | Arm 3 | ACCATCATGTGC | 61 | 12 | 49.2 |
| miR-17-5p | CCACGCGACGCTGCACTGTAAG | 62 | Arm 4 | CTGCACTGTAAG | 63 | 12 | 45.7 |
| miR-18a | GACGCGGAGCA TACAATGCA | 64 | Arm 3 | CCATACAATGCA | 65 | 12 | 48.2 |
| miR-19b | GACGCGGAGTCATGCAAAAC | 66 | Arm 3 | TCCATGCAAAAC | 67 | 12 | 46.3 |
| miR-21 | GACGCGGAATCAGTCTGAT | 68 | Arm 3 | ATCAGTCTGAT | 69 | 11 | 37.7 |
| miR-28 | GACGCGGACAGTAGACTGTGAGC | 70 | Arm 3 | AAGACTGTGAGC | 71 | 12 | 46.3 |
| miR-92 | CCACGGACGCAGGACAAGTG | 72 | Arm 4 | CGGGACAAGTG | 73 | 11 | 48.2 |
| miR-126 | CCACGGACCATGATTGATAATG | 74 | Arm 4 | TCAGTAATAATG | 75 | 12 | 34.7 |
| miR-223 | CCACGGAGAGAGATTGACAAAC | 76 | Arm 4 | ATTTGACAAAC | 77 | 11 | 35.5 |
| miR-29a | GACGCGGAGTTTCAGATGGT | 78 | Arm 3 | TTTCAGATGGT | 79 | 11 | 39.3 |
| miR-22 | CCACGGACCAGTTGAAGAACT | 80 | Arm 4 | AGTTGAAGAACT | 81 | 12 | 41.7 |
| miR-16 | GACGCGGAGATATTTACGTGC | 82 | Arm 3 | ATATTTACGTGC | 83 | 12 | 41.2 |
| miR-20a | CCACGCGACGCACTATAAGCA | 84 | Arm 4 | GCACTATAAGCA | 85 | 12 | 44.0 |
| miR-155 | GACGCGGACAATCACCATTAGC | 7 | Arm 3 | ATCACCATTAGC | 87 | 12 | 44.3 |
| miR-342 | GACGCGGACTGCGATTCTGT | 98 | Arm 3 | TCCGATTCTGT | 89 | 12 | 47.9 |
| mRNA | | | | | | | |
| NM_001823-[670]-5 (CKB) | GACGCGGAGCCAGGAAGGTCT | 90 | Arm 3 | CCAGGAAGGTCT | 91 | 12 | 49.7 |
| NM_016139-[1005]-3 (CHCHD2) | GACGCGGAGGCCTTAATGAAGA | 92 | Arm 3 | GCCTTAATGAAGA | 93 | 12 | 43.2 |
| NM_006908-[808]-3 (RAC1) | GACGCGGAGGCAAGGCAAAAGC | 94 | Arm 3 | CAAGGCAAAAGC | 95 | 12 | 47.0 |
| NM_021791-[464]-3 (CDC42) | GACGCGGAGAGCATTATGACA | 96 | Arm 3 | AGGATTATGACA | 97 | 12 | 40.3 |
| NM_002086-[607]-6 (GRB2) | GACGCGGAGAAACGATGTGC | 98 | Arm 3 | GAAACGGATGTGC | 99 | 12 | 48.2 |
| NM_002654-[497]-4 (PKM2) | GCGCGTCCACTGCAGAGCT | 100 | Arm 7 | CACTGCAGAGCT | 101 | 12 | 51.5 |
| NM_030662-[676]-2 (MAP2K2) | GCGCGTCCCACCTGAGAT | 102 | Arm 7 | CCACCTGAGAT | 103 | 12 | 46.6 |
| NM_005594-[619]-1 (IL8) | GACGCGGAGACTCCTTGGCAA | 104 | Arm 3 | ACTCCTTGGCAA | 105 | 12 | 50.5 |
| NM_005858-[774]-4 (SOK1) | GACGCGGAGCTCCCTGGTTAC | 106 | Arm 3 | CTCCCTGGTTAC | 107 | 12 | 47.4 |
| NM_001110-[497]-11 (ADAM10) | GACGCGGAGGTCAAGGTCCTT | 108 | Arm 3 | GTCAAGGTCTT | 109 | 12 | 47.0 |
| NM_004395-[811]-6 (ODX5) | GATGCGGAGTTTGCAACAACAG | 110 | Arm 3 | GTTGCAACACAG | 111 | 12 | 43.3 |
| NM_002634-[224]-3 (PHB) | GACGCGGAGCAGAATGCAAC | 112 | Arm 3 | CAGAATGCAAC | 113 | 12 | 42.5 |
| NM_004523-[2011]-4 (BAG1) | GACGCGGAGCAAATCCTTGG | 114 | Arm 3 | GCAAATCCTTGG | 115 | 12 | 47.2 |
| NM_014730-[3548]-1 (C14orf43) | GACGCGGAGATTGCTGAAGGT | 116 | Arm 3 | ATTGCTGAAGGT | 117 | 12 | 47.1 |
| NM_002046-[1933]-7 (GAPDH) | GCGCCGAGGAGTCCATGCAT | 118 | Arm 3 | AGTCCATGCAT | 119 | 12 | 50.3 |
| NM_005030-[1833]-6 (PLK1) | GCCGCTCCCACAAGCTCAT | 120 | Arm 7 | CACCAAGCTCAT | 121 | 12 | 48.4 |
| NM_002709-[2064]-4 (PPP1CB) | GCCGCTCCATTGCACGCTG | 122 | Arm 7 | ATTGCAGGCTG | 123 | 12 | 48.4 |
| NM_015645-[2062]-7 (ZAP1B) | GACGCGGAGAAGAACTGTTGC | 124 | Arm 3 | AAGAACTGTTGC | 125 | 12 | 45.7 |
| NM_002512-[2885]-2 (NME1) | GACGCGGAGTGAAGAACACCT | 126 | Arm 3 | TGAAGAACACCT | 127 | 12 | 45.5 |
| NM_000125-[3422]-1 (ESR1) | GACGCGGAGGTCCATTATC | 128 | Arm 3 | GCCTCGATTATC | 129 | 12 | 46.7 |
| DNA | | | | | | | |
| FV (mutant) | CCACGCGACCAAGCAATACAGG | 46 | Arm 4 | AAGCAATACAGG | 131 | 12 | 42.3 |
| FV (wildtype) | CGAGCGGAGGAGAATACAGG | 28 | Arm 6 | GAGGAATACAGG | 133 | 12 | 43.4 |
| FII (wildtype) | GACGCGGAGGAGCCTCAATGC | 34 | Arm 3 | GAGCCTCAATGC | 135 | 12 | 50.6 |
| FII (mutant) | CGCCAGAGAGCCTCAATGC | 136 | Arm 1 | AAGCCTCAATGC | 137 | 12 | 49.7 |
| CT | GACGCGGAGCGTTTAAATCA | 138 | Arm 3 | CGTTTAAATCA | 139 | 12 | 38.2 |
| NG | CCACGGACGCTGTTCCGTCAG | 140 | Arm 4 | CTGTTCCGTCAG | 134 | 12 | 49.4 |

FIGURE 5
FV genotyping design

```
2749-70-03, Arm 4-Yellow (Mutant)  5'-CCACGGACG              AAGGAATACAGG-HEX-3' (SEQ ID NO:46)
2749-70-04, Arm 6-FAM (Wildtype)   5'-CGAGGGCCG              GAGGAATACAGG-HEX-3' (SEQ ID NO:28)
                                                             |||||||||||||
2749-70-07 (SEQ ID NO:48)
AGGACTACTTCTAATCTGTAAGAGC-->
||||||||||||||||||||||||||||||||||||||||||||||||x          |||||||||||||
5'-TAATAGGACTACTTCTAATCTGTAAGAGCAGATCCCTGGACAGGCGAGGAATACAGGTATTTTGTCCTGAAGTAACCTTTCAGAAATT-3'
                                 |||||||||||||||                         |||||||||||||||||||||
                                 GATCCCTGGACAGGCC                        <--CAGGAACTTCATTGGAAAGTCTT
                                 2749-70-05 (SEQ ID NO:49)               2749-70-06 (SEQ ID NO:50)
```

Arm 6 FAM FRET    =   5'-FAM-TCT-Z28-AGCCGGTTTTCCGGCTGAGACGGCCTCGCG-HEX-3'   (SEQ ID NO:6)
Arm 4 Yellow FRET =   5'-Yellow-TCT-Z28-AGCCGGTTTTCCGGCTGAGACGTCCGTGGCCT-HEX-3'   (SEQ ID NO:51)

(From Luderer, et al., Clinical Chemistry Vol. 50, No. 4, 2004:787)

Differentiation between wild-type and vaccine mutant VZV using the Invader Plus reagents [a]

| Sample type | Number tested | FAM average FOZ[b] | % CV[c] | Red average FOZ[b] | % CV[c] | FOZ[b] ration FAM/Red |
|---|---|---|---|---|---|---|
| Wild-type[d] | 29 | 0.97 | 0.16 | 1.97 | 0.44 | 0.49 |
| Vaccine mutant[d] | 18 | 3.52 | 1.22 | 1.12 | 0.10 | 3.13 |
| Negative | 3 | 0.94 | 0.21 | 1 | 0.05 | 0.94 |
| Webster (wild-type control) | 1 | 1.14 | | 2.61 | | 0.44 |
| Oka (Vaccine mutant control) | 3 | 5.22 | 0.72 | 1.01 | 1.01 | 5.2 |
| VTM (No target blank) | 1 | | | | | |

[a] The Invader Plus differentiation reaction is configured to generate Red or FAM fluorescence signal for wild-type or Oka strains of ZV, respectively.
[b] FOZ: fold over zero.
[c] CV: coefficient of variation; VTM: viral transport medium.
[d] The genotypes were determined by an allele-specific TaqMan real-time assay (Loparev et al., 2000)

(From: Y.-Wang, et at., Journal of Clinical Virology 40 (2007) 129-134)

B WT VZV sample

C Oka VZV sample

D no target control

FIGURE 9
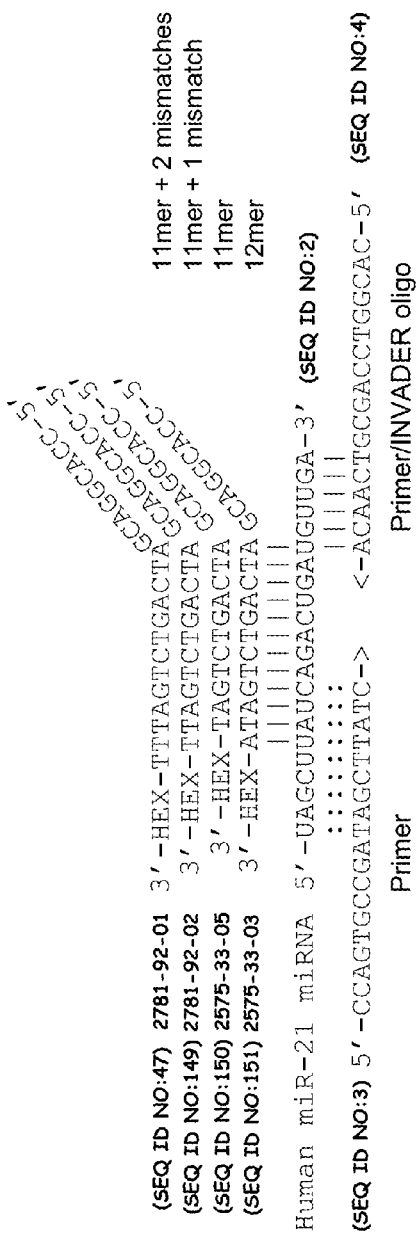
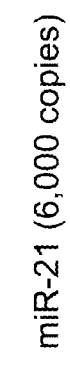
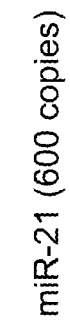
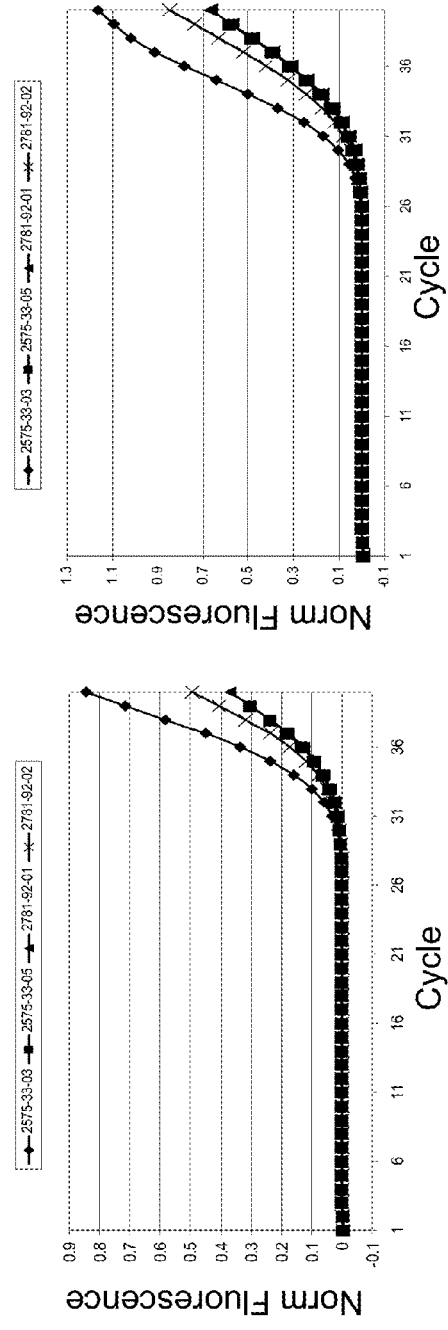

FIGURE 11 A-C

A. HUMAN miR-21 Design

```
                                      GAGGCGCAG-5'
                                     ⁄           (SEQ ID NO:1)
       3'-NH2-TAGTCTGACTA ⁄
                |||||||||||
           5'-UAGCUUAUCAGACUGAUGUUGA-3'  ← miR-21  (SEQ ID NO:2)
              |||||||||          ||||||
   5'-CCAGTGCCGATAGCTTATC        ACAACTGCGACCTGGCAC-5' (SEQ ID NO:4)
       (SEQ ID NO:3)              ||||||||||||
                                  CGCTGGACCGTG-HEX-3'
                                      (SEQ ID NO:5)
```

B. HUMAN miR-155 Design

```
                                      GAGGCGCAG-5'
                                     ⁄           (SEQ ID NO:7)
       3'-NH2-CGATTAGCACTA ⁄
                |||||||||||
           5'-UUAAUGCUAAUCGUGAUAGGGG-3'  (SEQ ID NO:8)
              |||||||||         ||||||
   5'-GTGCTCAGCCAGGTTAATGCTA    ATCCCCGCGACCTGGCAC-5' (SEQ:10)
       (SEQ ID NO:9)             ||||||||||||
                                 CGCTGGACCGTG-HEX-3'
                                      (SEQ ID NO:5)
```

C. HUMAN-miR-126 Design

```
                                      GAGGCGCAG-5'
                                     ⁄           (SEQ ID NO:11)
       3'-NH2-TGGCACTCATTA ⁄
                |||||||||||
           5'-UCGUACCGUGAGUAAUAAUGC-3'  (SEQ ID NO:12)
              |||||||||        ||||||                (SEQ ID NO:14)
   5'-CCAGTGCCGATCGTACCGT      ATTACGGCGACCTGGCAC-5'
       (SEQ ID NO:13)           ||||||||||||
                                CGCTGGACCGTG-HEX-3'
                                    (SEQ ID NO:5)
```

FRET: miR-21,155,and 126

5'-FAM-TCT-Z28-AGCCGGTTTTCCGGCTGAGACTCCGCGTCCGT-HEX-3'
(SEQ ID NO:6)

FIGURE 11 D-E
D. HUMAN U6 snRNA Design
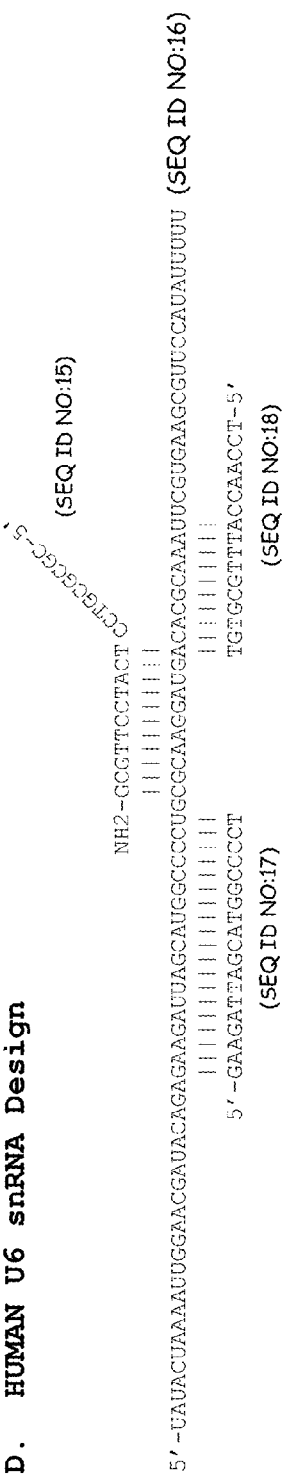
E. Human U24 snRNA Design
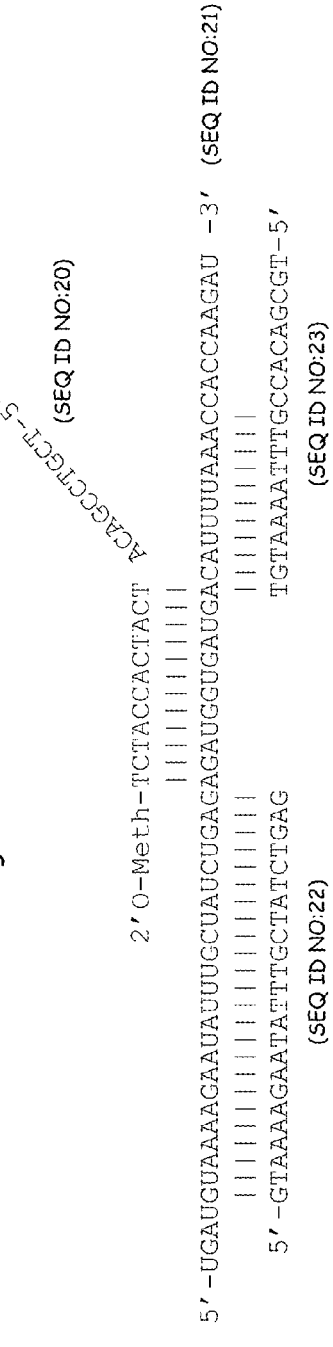

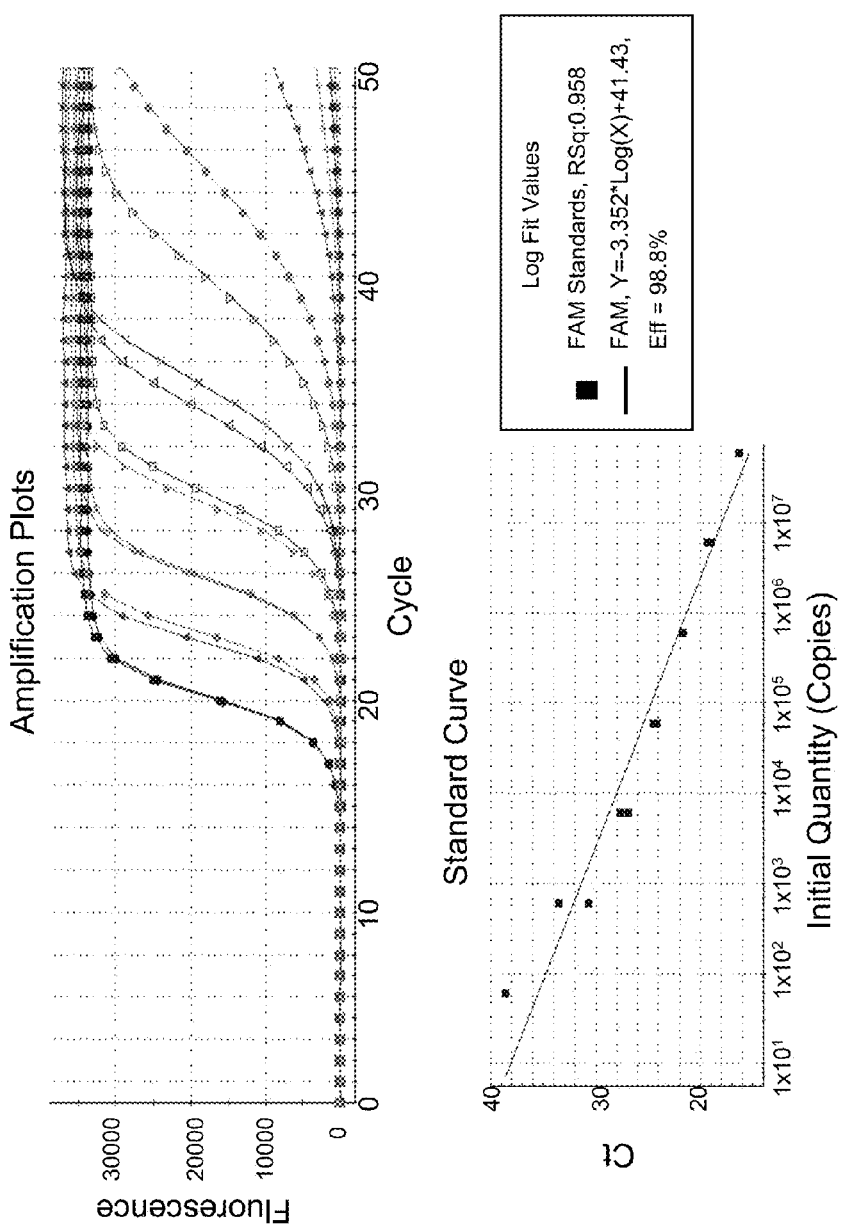

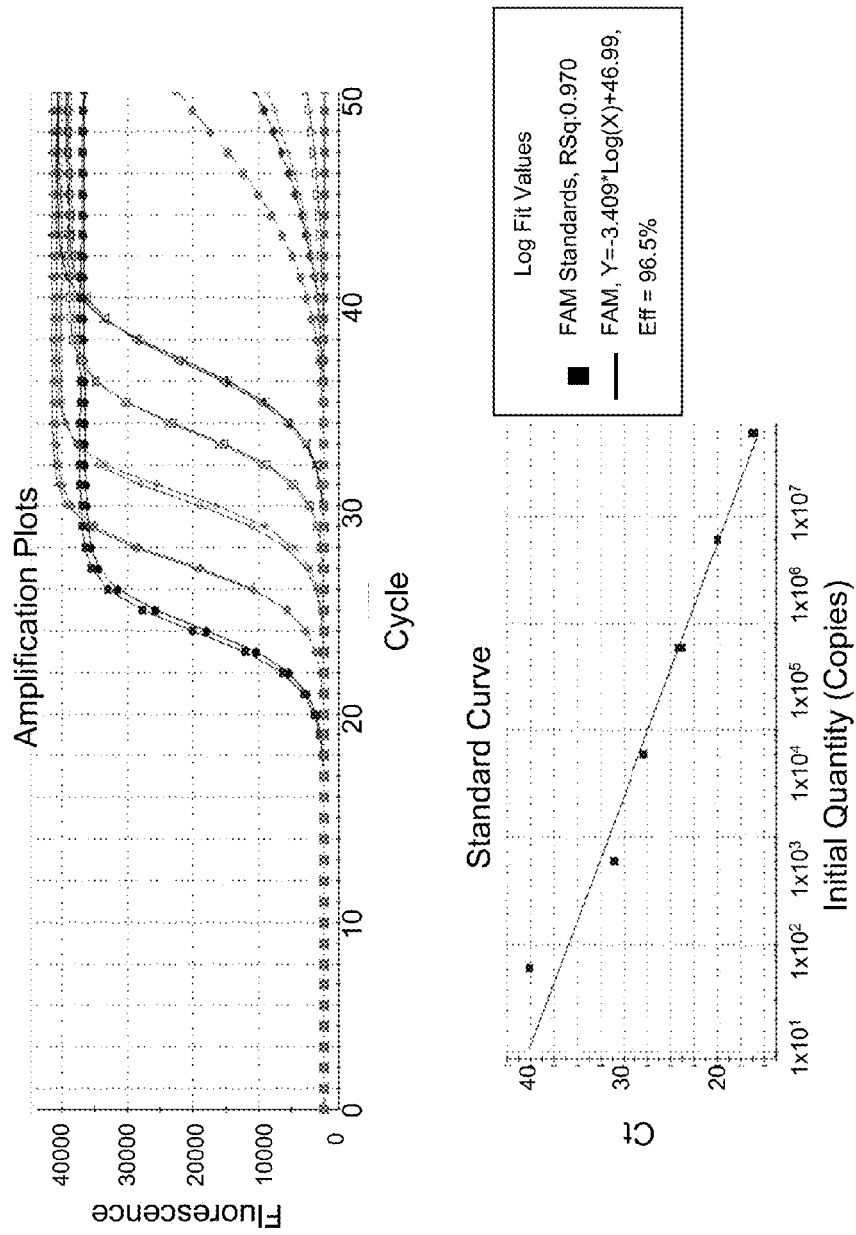

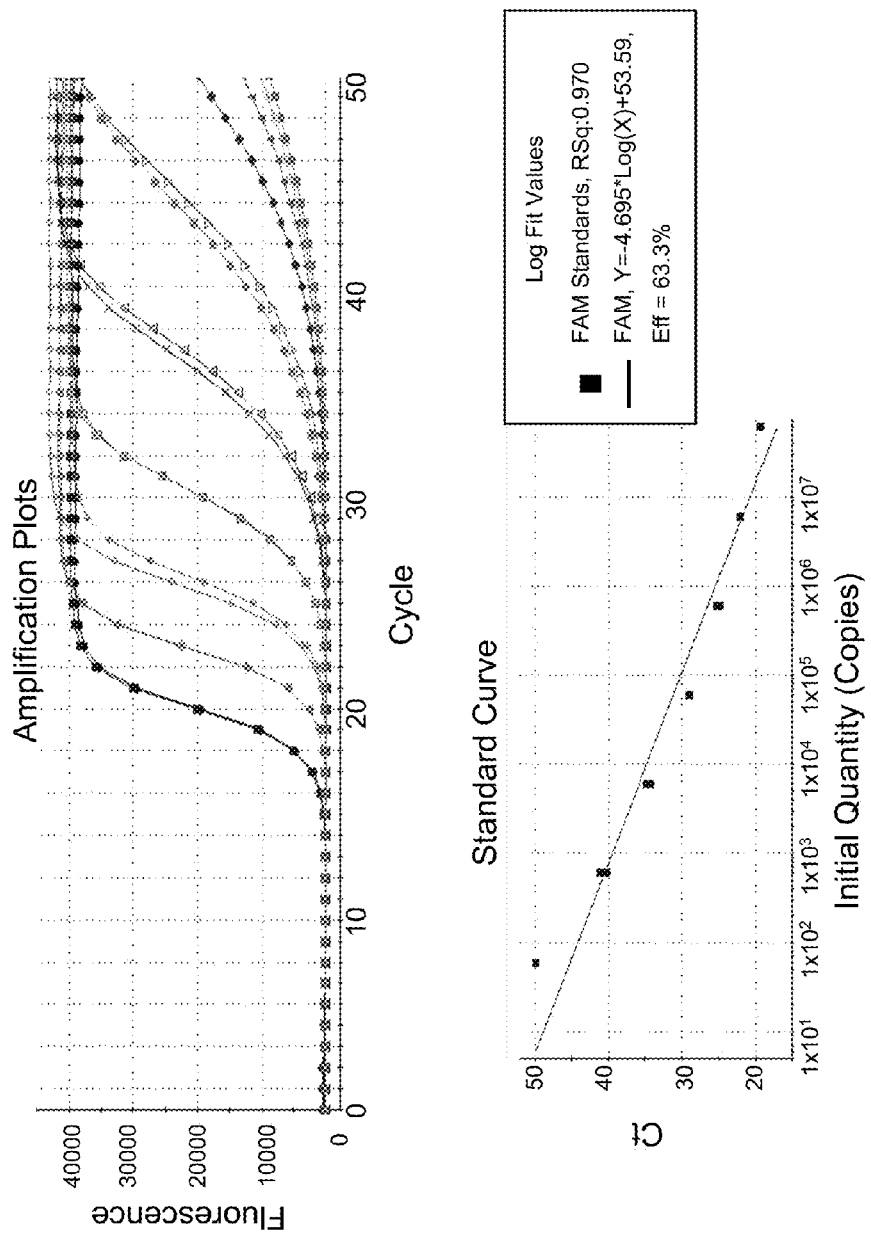

miR-U6

A. U6 DNA design

```
                              ,5'-CCTGCGCGGTCC
                              NH2-GCGTTCCTACT
                              |||||||||||||||
5'-CAGAGAACATTAGCATGGCCCCTGCCCAAGGATGACACGGAAATTCCGAAGCGTCC (SEQ ID NO:15)
   |||||||||||||||||||||||                 ||||||||||||||||
   5'-GAAGATTAGCATGGCCCCT          TGTGCGTTAAGCACTTCG-5' (SEQ ID NO:26)
          (SEQ ID NO:17)
                                    GCGTTAAGCACTTCGGA-5'
                                    (SEQ ID NO:27) Reverse Primer
```

B. Factor V DNA design

```
                                    5'-CGAGGCCG GAGGAATACAGG-HEX-3' (SEQ ID NO:28)
                                    ||||||||| |||||||||||||
AGGACTACTTCTAATCTGTAAGAGC-->                 GAGGAATACAGGCGAGGAATACAGGTATTTGTCCTGAAGTAACCTTTCAGAA-3'
|||||||||||||||||||||||||                    ||||||||||||x
5'-TAGGACTACTTCTAATCTGTAAGAGCAGATCCCTGGACAGGCGAGGAATACAGGTATTTGTCCTGAAGTAACCTTTCAGAA-3'
         (SEQ ID NO:30)
                                            GATCCCTGGACAGGCC
                                            CAGGAACTTCATTGGAAAGTCTT
                                            (SEQ ID NO:31)              (SEQ ID NO:32)
```

C. Factor II DNA design

```
                           ,5'-GAGGCCG-3'
                                         (SEQ ID NO:34)
        (SEQ ID NO:35) 3'-HEX-CGTAACTTCCGAG
                       |||||||||||||||
5'-GCCCATGAATAGCACTGG           CGTAACTTCCGAG
   ||||||||||||||||||           |||||||||||||
5'-GCTGCCCATGAATAGCACTGGGAGCACTGGGAGCATTGAGGGCTCGCTGAGAGTCACTTTTATTGGAACCATAGTTTAGAAACACAAAAT-3'
                                            ||||||||||||||||| |||||||||||||||||||||||||||||||||||
                                         3'-TCGACTCTCAGTGAAAATAAC CTTGGTATCAAAATCTTTGTGTTTTTA-5'
         (SEQ ID NO:36)                              (SEQ ID NO:37)              (SEQ ID NO:38)
```

---

U6 design FRET = 5'-RED-TCT-Z28-TCGGCCTTTTGGCCGAGAGAGGACGCGCGGA-HEX-3' (SEQ ID NO:19)

Factor V design FRET = 5'-RED-TCT-Z28-AGCCGGTTTTCCGGCTGAGACGGCCTGCGG-HEX-3' (SEQ ID NO:33)

Factor II design FRET = 5'-FAM-TCT-Z28-AGCCGGTTTTCCGGCTGAGACTCCGCGTCCGT-HEX-3' (SEQ ID NO:6)

FIGURE 13 D-E

D. GA-21-R DNA design

```
                                        (SEQ ID NO:39)                    (SEQ ID NO:40)
                              TACGACTGACGAACC-5    GAACCCGAAGTTTCTTC-5'
                              x|||||||||||||||||   |||||||||||||||||
5'-CGGACGACGAGCTCCTCCCCCCCTCCGCCGTTGCTGACTGCTGTTGGGCTTCAAAGAAG-3' (SEQ ID NO:44)
  |||||||||||||||||
5'-CGGACGACGAGCT->        3'-NH2-ggaggcggca GAGGCGGCAG (Probe 10) (SEQ ID NO:42)
   (SEQ ID NO:41)         3'-NH2-gggaggcggca GAGGCGGCAG (Probe 11) (SEQ ID NO:43)

FRET = 5'-FAM-TCT-Z28-AGCCGGTTTTCCGGCTGAGACTCCGCGTCCGT-HEX-3' (SEQ ID NO:6)
```

E. U6 RNA design

```
                                              CCUGCGCGC-5'
                                              |||||||||
                                        NH2-GCGTTCCTACT
                                            |||||||||||
5'-CAGAGAAGAUUAGCAUGGCCCCUGCGCAAGGAUGACACGCAAAUUCGTGAAGCGUUCC (SEQ ID NO:45)
   ||||||||||||||||||||||||||                |||||||||||||||||
5'-GAAGATTAGCATGGCCCCT                       TGTGCGTTTAAGCACTTCG-5' (SEQ ID NO:26)
   (SEQ ID NO:17)
                                              GCGTTTAAGCACTTCGGA-5'
                                              (SEQ ID NO:27) Reverse Primer

FRET = 5'-RED-TCT-Z28-TCGGCCTTTTGGCCGAGAGGACGCGCGGA-HEX-3' (SEQ ID NO:19)
```

FIGURE 14 A-B
+ Invasive Oligo / + Afu FEN-1
A.
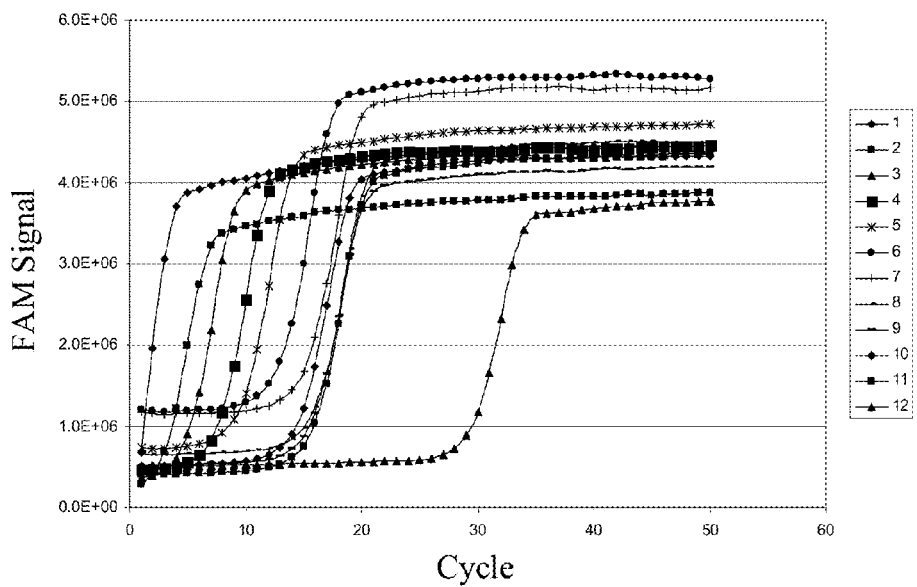
B.
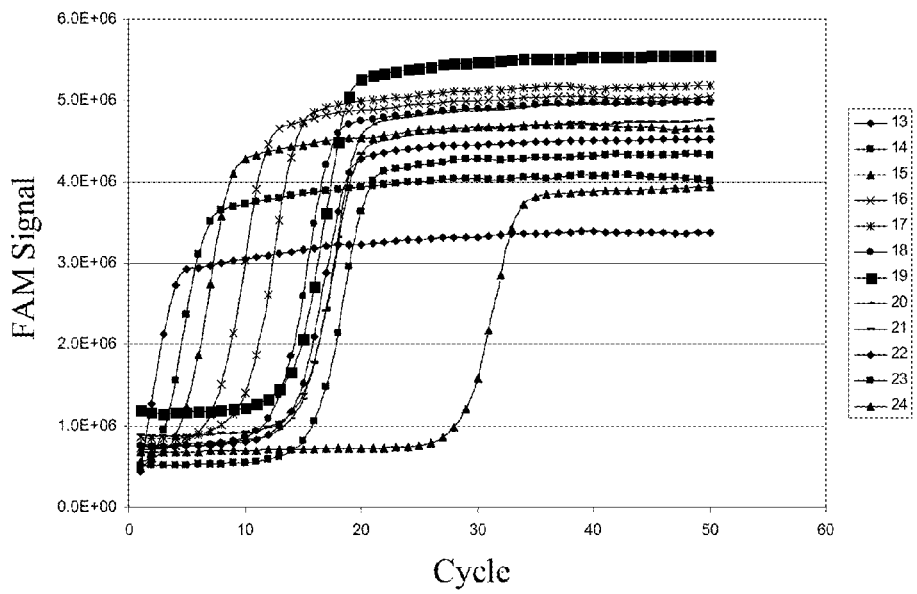

FIGURE 14 C-D
- Invasive Oligo / - Afu FEN-1
C.
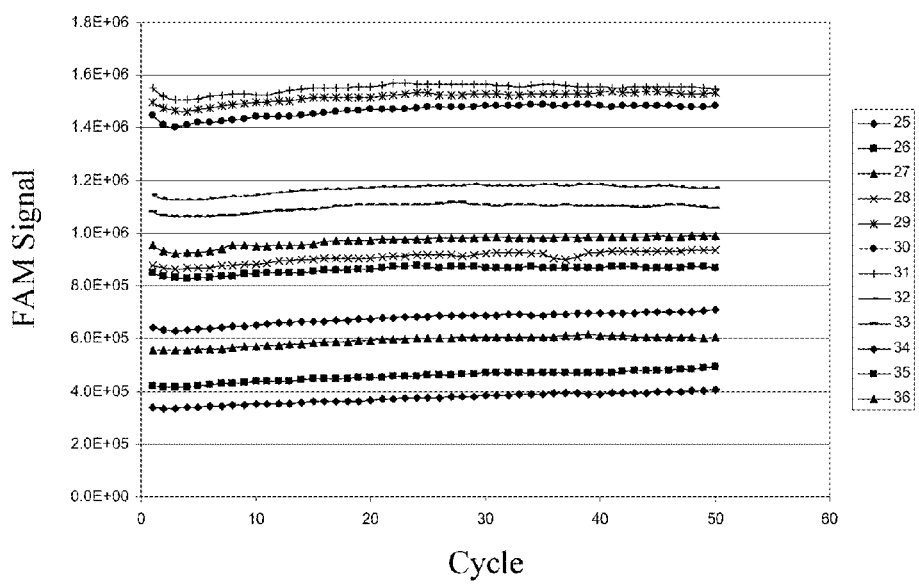
D.
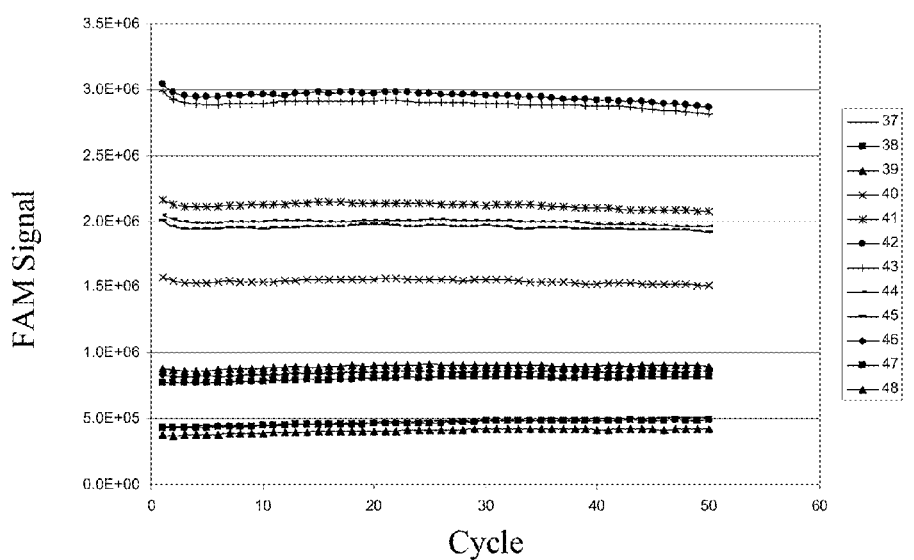

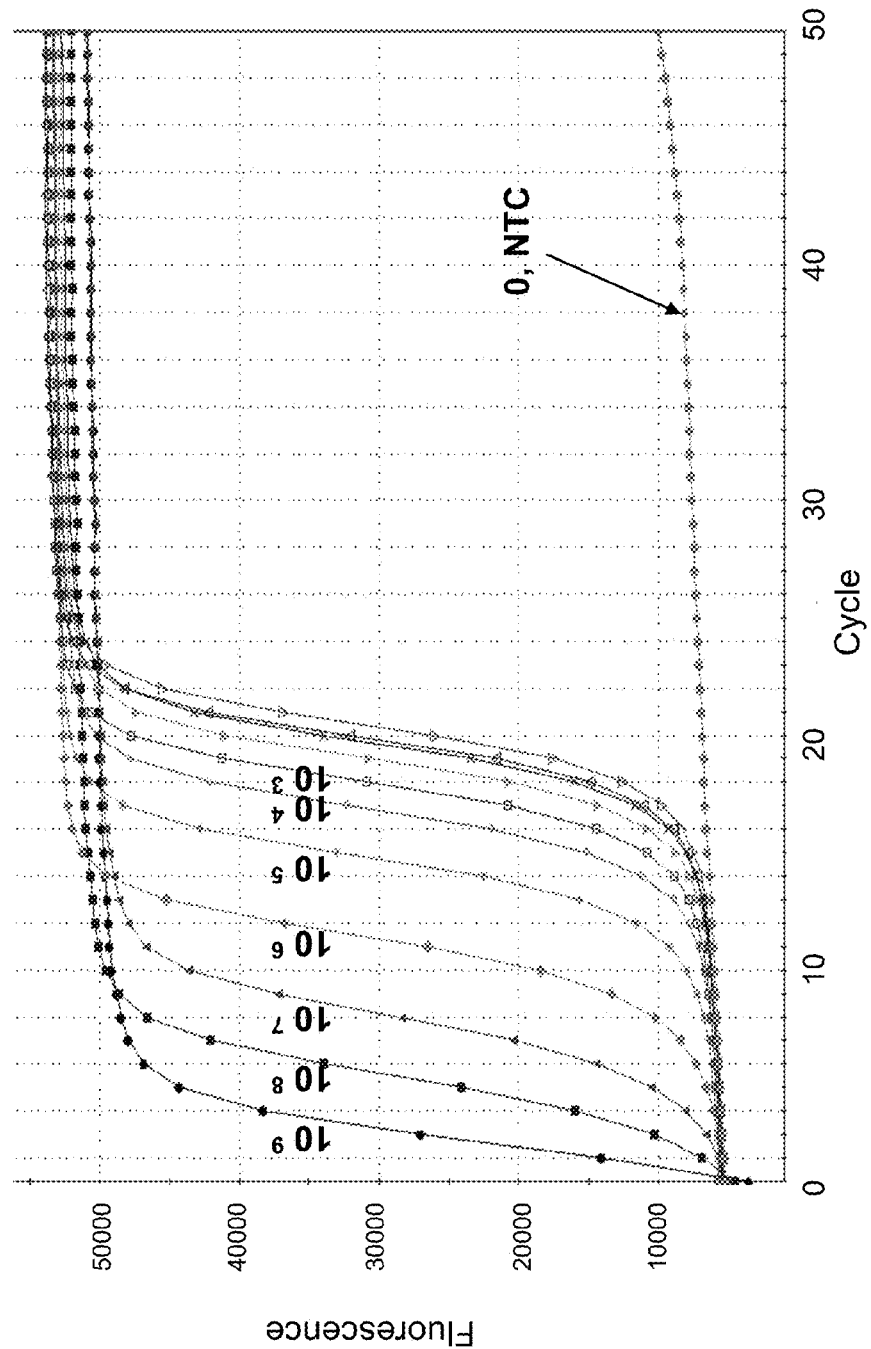

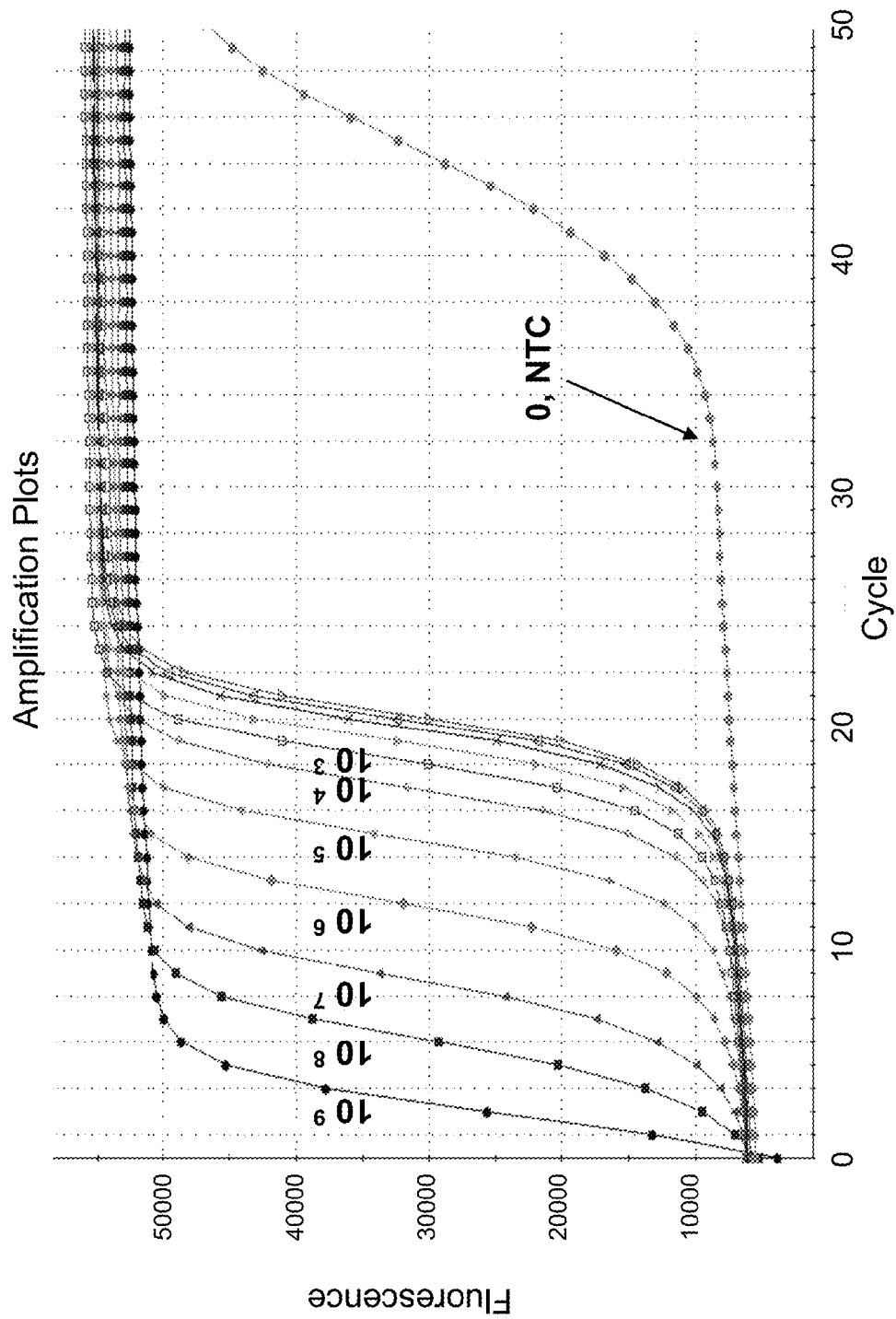

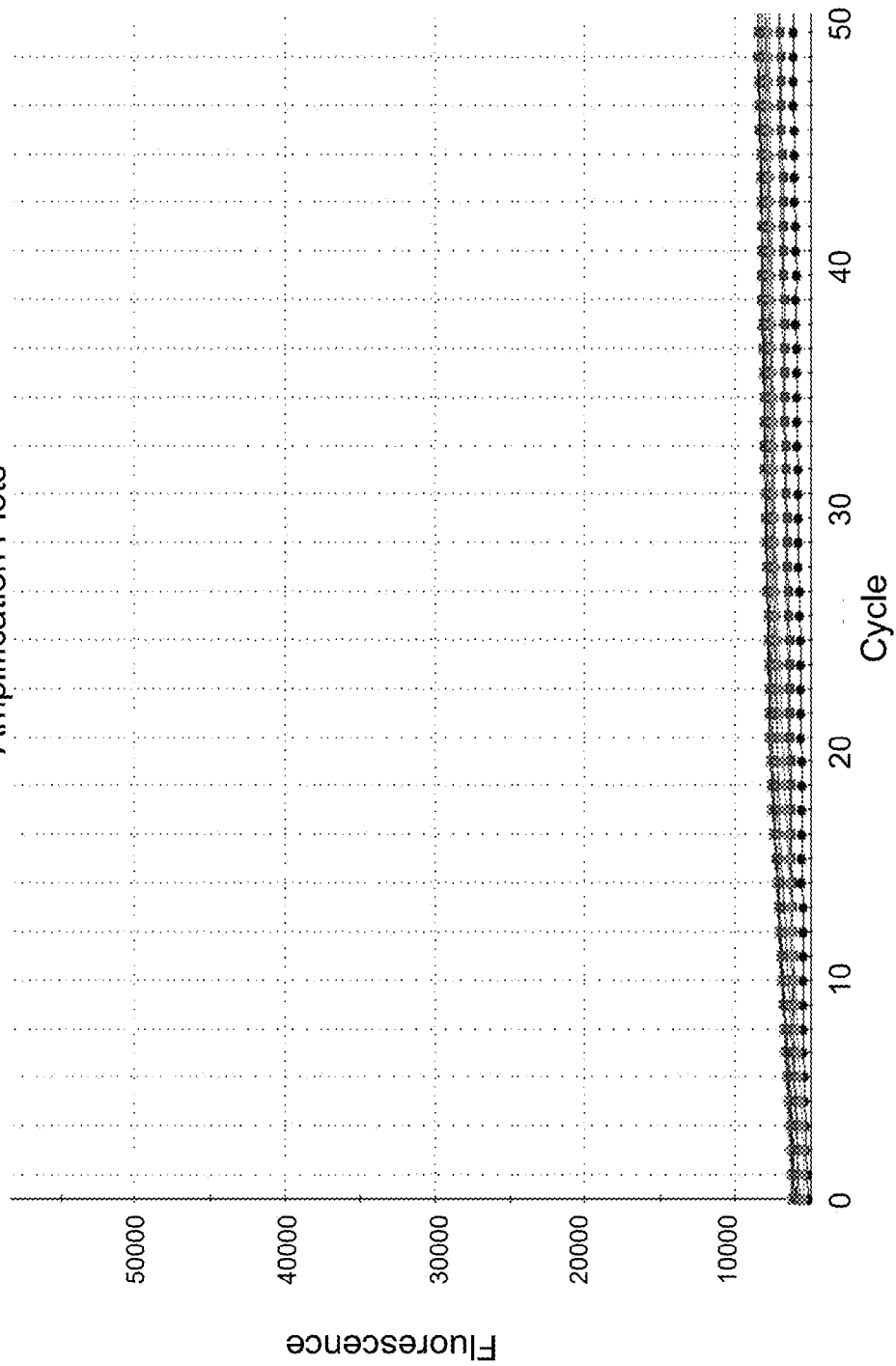

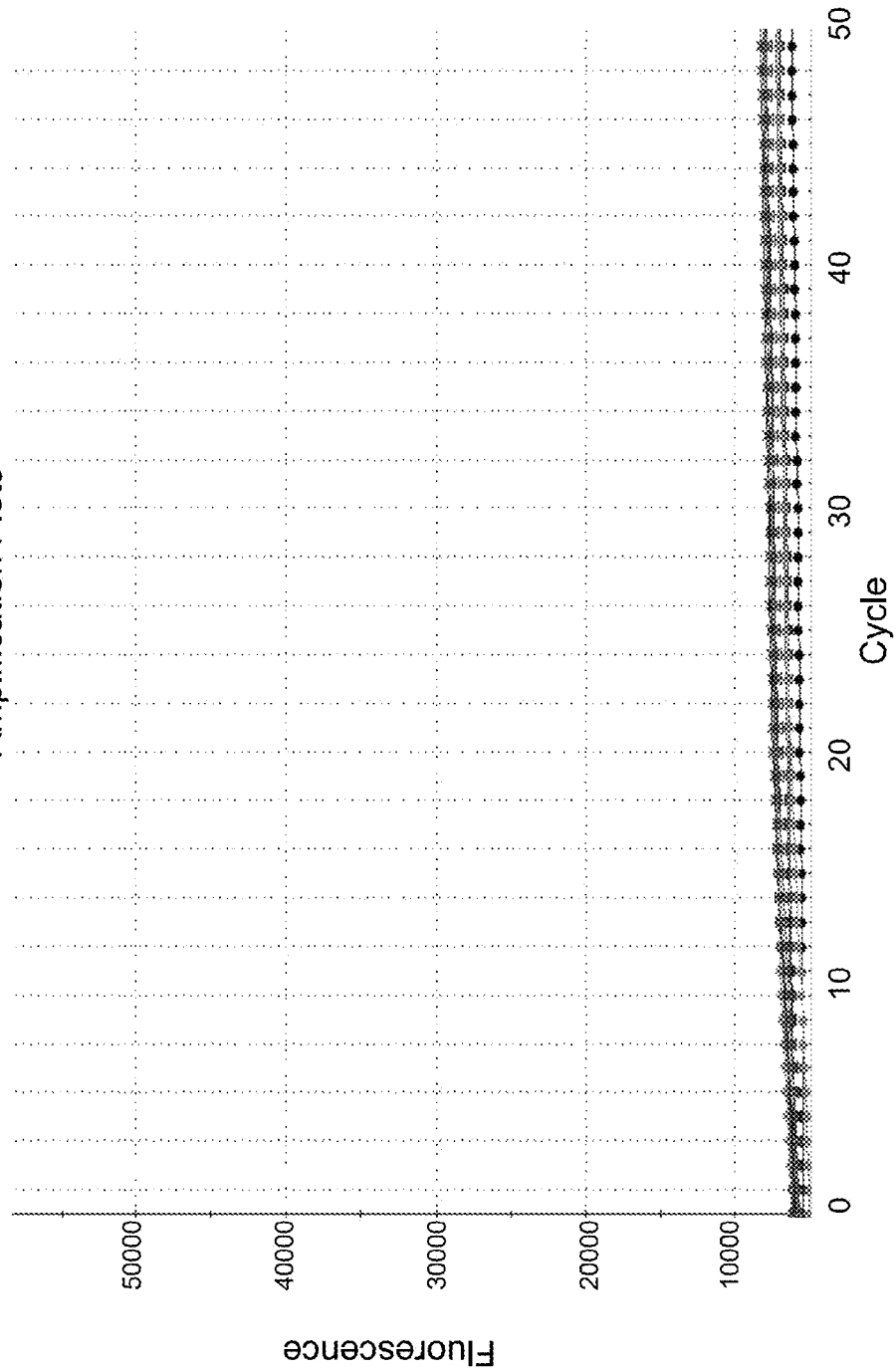

Amplification Plots

FIGURE 16 A-B
+ Invasive Oligo / + Afu FEN-1
A. 10-mer Probe; 56 degrees Celsius
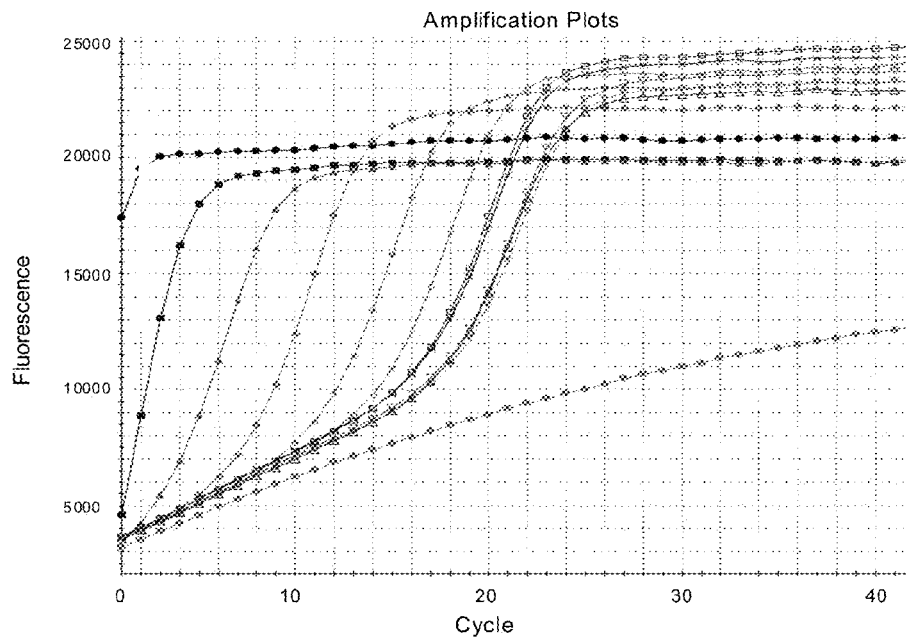
B. 11-mer Probe; 56 degrees Celsius
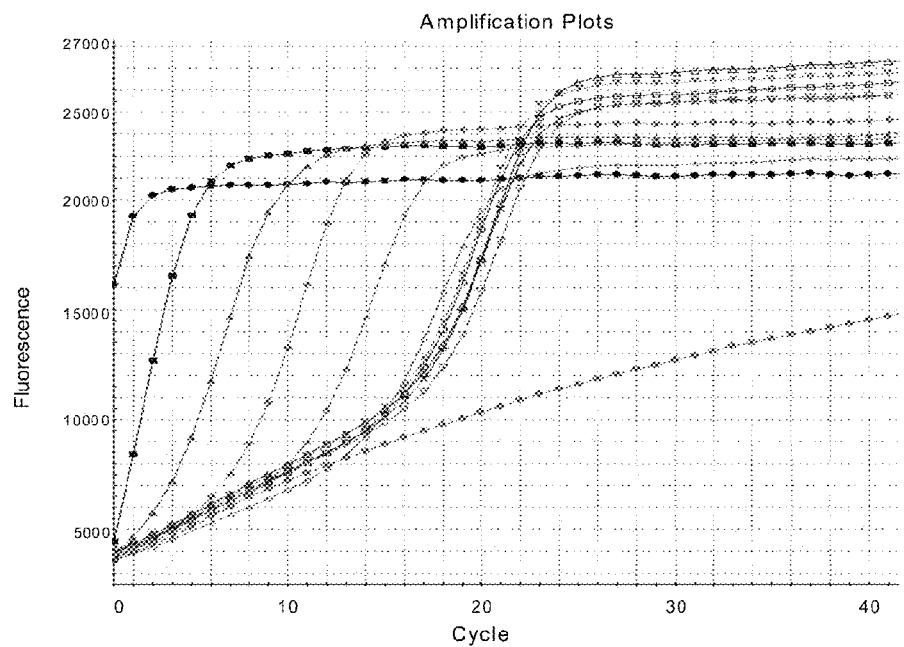

FIGURE 16 C-D
- Invasive Oligo / - Afu FEN-1
C. 10-mer Probe; 56 degrees Celsius
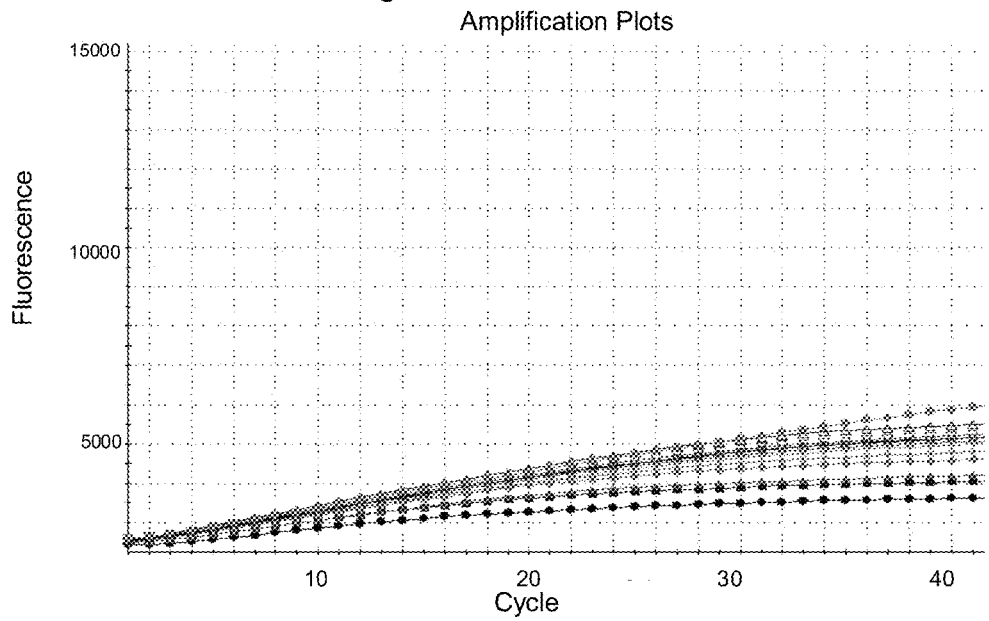
D. 11-mer Probe; 56 degrees Celsius
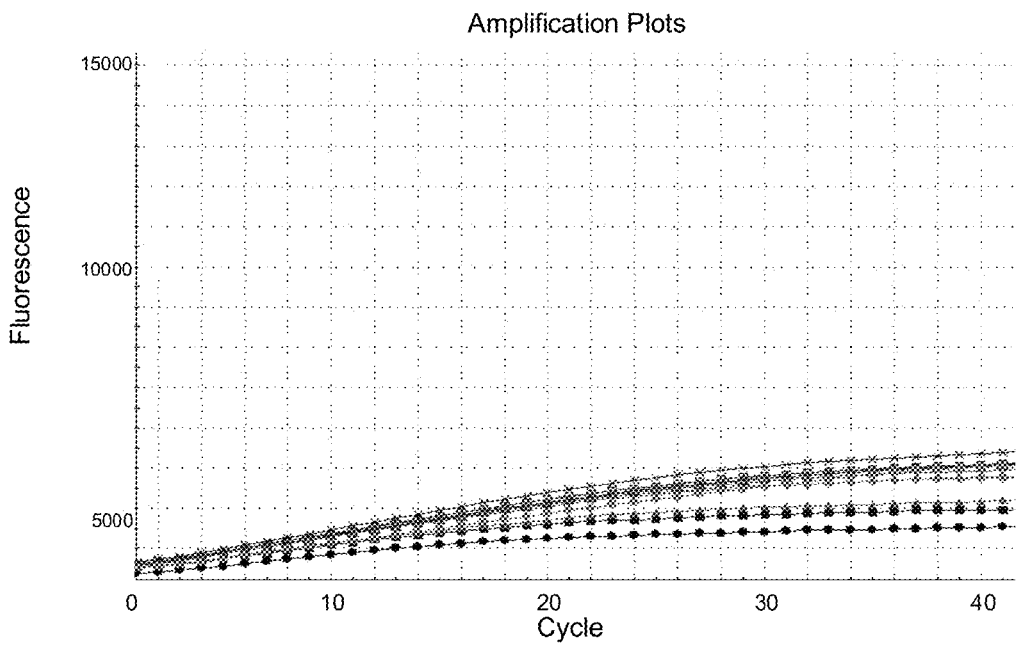

FIGURE 17 A-B
+ Invasive Oligo / + Afu FEN-1
A.
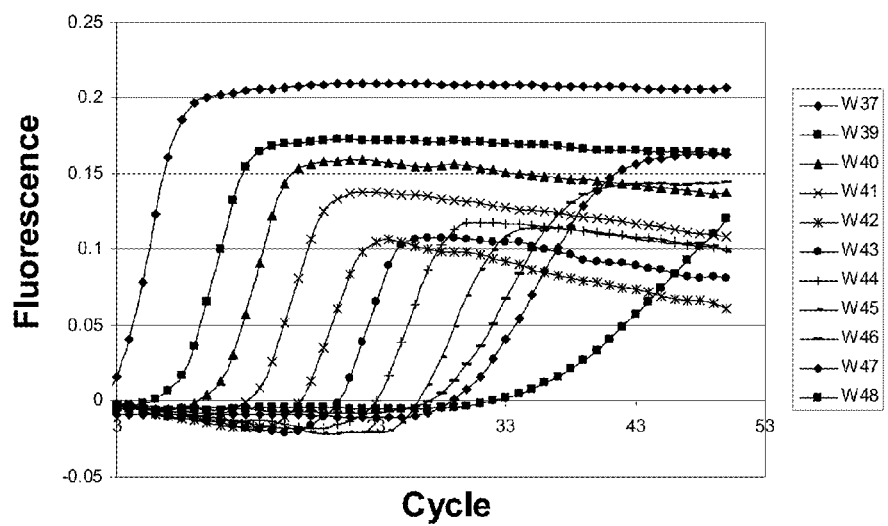
B.
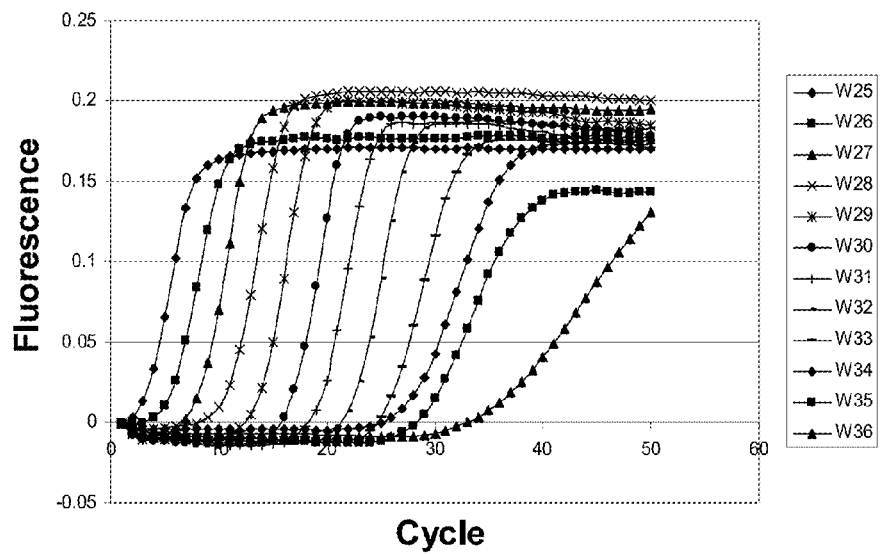

FIGURE 17 C-D
- Invasive Oligo / - Afu FEN-1
C.
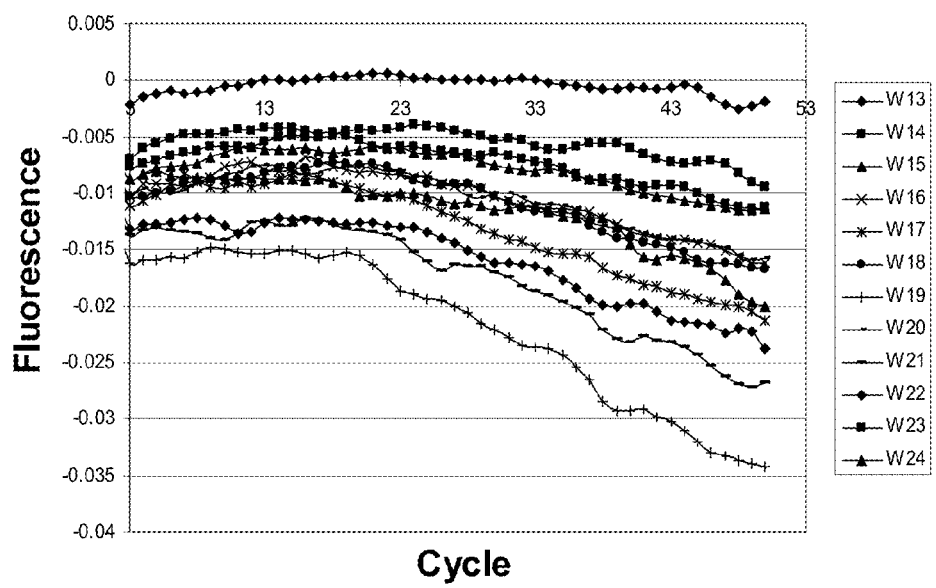
D.
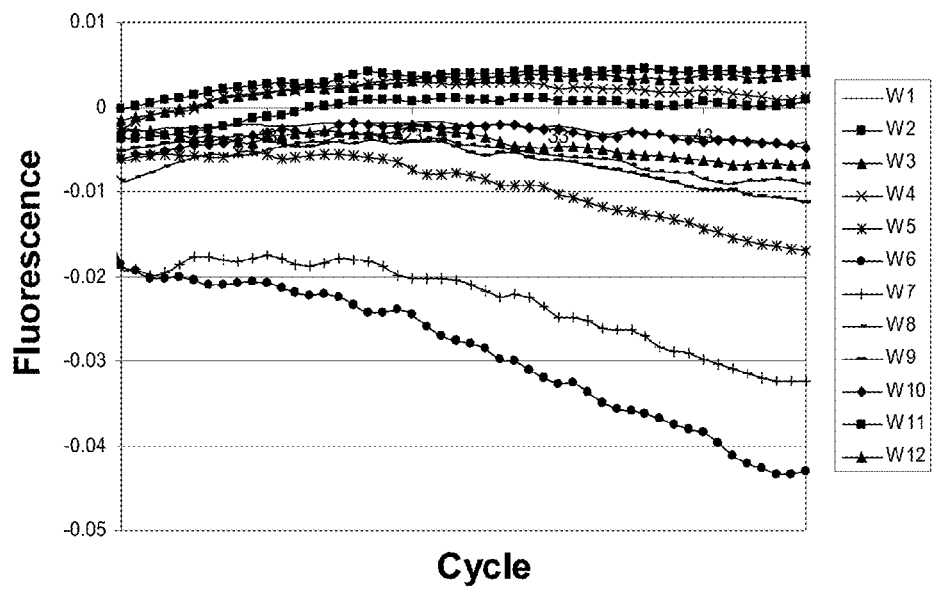

SEQUENCE LISTING

<160> NUMBER OF SEQ ID NOS: 155

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
gacgcggaga tcagtctgat                                                     20

<210> SEQ ID NO 2
<211> LENGTH: 22
<212> TYPE: RNA
<213> ORGANISM: Artificial Sequence
<220> FEATURE:
<223> OTHER INFORMATION: Synthetic

<400> SEQUENCE: 2
uagcuuauca gacugauguu ga                                                  22

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
ccagtgccga tagcttatc                                                      19

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
cacggtccag cgtcaaca                                                       18

<210> SEQ ID NO 5
<211> LENGTH: 12
<212> TYPE: DNA
<213> ORGANISM: Artificial Sequence
<220> FEATURE:
<223> OTHER INFORMATION: Synthetic

<400> SEQUENCE: 5
cgctggaccg tg                                                             12

<210> SEQ ID NO 6
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: This residue is linked to an Eclipse Quencher.

<400> SEQUENCE: 6
tctagccggt tttccggctg agactccgcg tccgt                                    35

```
<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
gacgcggaga tcacgattag c                                              21

<210> SEQ ID NO 8
<211> LENGTH: 22
<212> TYPE: RNA
<213> ORGANISM: Artificial Sequence
<220> FEATURE:
<223> OTHER INFORMATION: Synthetic

<400> SEQUENCE: 8
uuaaugcuaa ucgugauagg gg                                             22

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
gtgctcagcc aggttaatgc ta                                             22

<210> SEQ ID NO 10
<211> LENGTH: 18
<212> TYPE: DNA
<213> ORGANISM: Artificial Sequence
<220> FEATURE:
<223> OTHER INFORMATION: Synthetic

<400> SEQUENCE: 10
cacggtccag cgccccta                                                  18

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
gacgcggaga ttactcacgg t                                              21

<210> SEQ ID NO 12
<211> LENGTH: 21
<212> TYPE: RNA
<213> ORGANISM: Artificial Sequence
<220> FEATURE:
<223> OTHER INFORMATION: Synthetic

<400> SEQUENCE: 12
ucguaccgug aguaauaaug c                                              21

<210> SEQ ID NO 13
<211> LENGTH: 19
<212> TYPE: DNA
<213> ORGANISM: Artificial Sequence
<220> FEATURE:
<223> OTHER INFORMATION: Synthetic
```

```
<400> SEQUENCE: 13
ccagtgccga tcgtaccgt                                                    19

<210> SEQ ID NO 14
<211> LENGTH: 18
<212> TYPE: DNA
<213> ORGANISM: Artificial Sequence
<220> FEATURE:
<223> OTHER INFORMATION: Synthetic

<400> SEQUENCE: 14
cacggtccag cggcatta                                                     18

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
cgcgcgtcct catccttgcg                                                   20

<210> SEQ ID NO 16
<211> LENGTH: 87
<212> TYPE: RNA
<213> ORGANISM: Artificial Sequence
<220> FEATURE:
<223> OTHER INFORMATION: Synthetic

<400> SEQUENCE: 16
uauacuaaaa uuggaacgau acagagaaga uuagcauggc cccugcgcaa ggaugacacg       60
caaauucgug aagcguucca uauuuuu                                           87

<210> SEQ ID NO 17
<211> LENGTH: 19
<212> TYPE: DNA
<213> ORGANISM: Artificial Sequence
<220> FEATURE:
<223> OTHER INFORMATION: Synthetic

<400> SEQUENCE: 17
gaagattagc atggcccct                                                    19

<210> SEQ ID NO 18
<211> LENGTH: 17
<212> TYPE: DNA
<213> ORGANISM: Artificial Sequence
<220> FEATURE:
<223> OTHER INFORMATION: Synthetic

<400> SEQUENCE: 18
tccaaccatt tgcgtgt                                                      17

<210> SEQ ID NO 19
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: This residue is linked to an Eclipse Quencher.

<400> SEQUENCE: 19
```

```
tcttcggcct tttggccgag agaggacgcg cgga                               34

<210> SEQ ID NO 20
<211> LENGTH: 22
<212> TYPE: DNA
<213> ORGANISM: Artificial Sequence
<220> FEATURE:
<223> OTHER INFORMATION: Synthetic

<400> SEQUENCE: 20
tcgtccgaca tcatcaccat ct                                            22

<210> SEQ ID NO 21
<211> LENGTH: 59
<212> TYPE: RNA
<213> ORGANISM: Artificial Sequence
<220> FEATURE:
<223> OTHER INFORMATION: Synthetic

<400> SEQUENCE: 21
ugauguaaaa gaauauuugc uaucugagag auggugauga cauuuuaaac caccaagau    59

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
gtaaaagaat atttgctatc tgag                                          24

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
tgcgacaccg tttaaaatgt                                               20

<210> SEQ ID NO 24
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: This residue is linked to an Eclipse Quencher.

<400> SEQUENCE: 24
tcttcggcct tttggccgag agatgtcgga cgagct                             36

<210> SEQ ID NO 25
<211> LENGTH: 58
<212> TYPE: DNA
<213> ORGANISM: Artificial Sequence
<220> FEATURE:
<223> OTHER INFORMATION: Synthetic

<400> SEQUENCE: 25
cagagaagat tagcatggcc cctgcgcaag gatgacacgc aaattcgtga agcgttcc     58
```

```
<210> SEQ ID NO 26
<211> LENGTH: 19
<212> TYPE: DNA
<213> ORGANISM: Artificial Sequence
<220> FEATURE:
<223> OTHER INFORMATION: Synthetic

<400> SEQUENCE: 26
gcttcacgaa tttgcgtgt                                                  19

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
aggcttcacg aatttgcg                                                   18

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
cgaggccgga ggaatacagg                                                 20

<210> SEQ ID NO 29
<211> LENGTH: 83
<212> TYPE: DNA
<213> ORGANISM: Artificial Sequence
<220> FEATURE:
<223> OTHER INFORMATION: Synthetic

<400> SEQUENCE: 29
taggactact tctaatctgt aagagcagat ccctggacag gcgaggaata caggtatttt     60
gtccttgaag taacctttca gaa                                             83

<210> SEQ ID NO 30
<211> LENGTH: 25
<212> TYPE: DNA
<213> ORGANISM: Artificial Sequence
<220> FEATURE:
<223> OTHER INFORMATION: Synthetic

<400> SEQUENCE: 30
aggactactt ctaatctgta agagc                                           25

<210> SEQ ID NO 31
<211> LENGTH: 16
<212> TYPE: DNA
<213> ORGANISM: Artificial Sequence
<220> FEATURE:
<223> OTHER INFORMATION: Synthetic

<400> SEQUENCE: 31
gatccctgga caggcc                                                     16

<210> SEQ ID NO 32
<211> LENGTH: 23
<212> TYPE: DNA
<213> ORGANISM: Artificial Sequence
```

<220> FEATURE:
<223> OTHER INFORMATION: Synthetic

<400> SEQUENCE: 32
ttctgaaagg ttacttcaag gac                                          23

<210> SEQ ID NO 33
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: This residue is linked to an Eclipse Quencher.

<400> SEQUENCE: 33
tctagccggt tttccggctg agacggcctc gcg                               33

<210> SEQ ID NO 34
<211> LENGTH: 21
<212> TYPE: DNA
<213> ORGANISM: Artificial Sequence
<220> FEATURE:
<223> OTHER INFORMATION: Synthetic

<400> SEQUENCE: 34
gacgcggagg agcctcaatg c                                            21

<210> SEQ ID NO 35
<211> LENGTH: 18
<212> TYPE: DNA
<213> ORGANISM: Artificial Sequence
<220> FEATURE:
<223> OTHER INFORMATION: Synthetic

<400> SEQUENCE: 35
gcccatgaat agcactgg                                                18

<210> SEQ ID NO 36
<211> LENGTH: 83
<212> TYPE: DNA
<213> ORGANISM: Artificial Sequence
<220> FEATURE:
<223> OTHER INFORMATION: Synthetic

<400> SEQUENCE: 36
gctgcccatg aatagcactg ggagcattga ggctcgctga gagtcacttt tattgggaac    60
catagtttta gaaacacaaa aat                                          83

<210> SEQ ID NO 37
<211> LENGTH: 21
<212> TYPE: DNA
<213> ORGANISM: Artificial Sequence
<220> FEATURE:
<223> OTHER INFORMATION: Synthetic

<400> SEQUENCE: 37
caataaaagt gactctcagc t                                            21

<210> SEQ ID NO 38
<211> LENGTH: 27
<212> TYPE: DNA
<213> ORGANISM: Artificial Sequence
<220> FEATURE:

<223> OTHER INFORMATION: Synthetic

<400> SEQUENCE: 38
atttttgtgt ttctaaaact atggttc                                              27

<210> SEQ ID NO 39
<211> LENGTH: 15
<212> TYPE: DNA
<213> ORGANISM: Artificial Sequence
<220> FEATURE:
<223> OTHER INFORMATION: Synthetic

<400> SEQUENCE: 39
ccaagcagtc agcat                                                           15

<210> SEQ ID NO 40
<211> LENGTH: 17
<212> TYPE: DNA
<213> ORGANISM: Artificial Sequence
<220> FEATURE:
<223> OTHER INFORMATION: Synthetic

<400> SEQUENCE: 40
cttctttgaa gcccaag                                                         17

<210> SEQ ID NO 41
<211> LENGTH: 13
<212> TYPE: DNA
<213> ORGANISM: Artificial Sequence
<220> FEATURE:
<223> OTHER INFORMATION: Synthetic

<400> SEQUENCE: 41
cggacgacga gct                                                             13

<210> SEQ ID NO 42
<211> LENGTH: 19
<212> TYPE: DNA
<213> ORGANISM: Artificial Sequence
<220> FEATURE:
<223> OTHER INFORMATION: Synthetic

<400> SEQUENCE: 42
gacgcggaga cggcggagg                                                       19

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
gacgcggaga cggcggaggg                                                      20

<210> SEQ ID NO 44
<211> LENGTH: 70
<212> TYPE: DNA
<213> ORGANISM: Artificial Sequence
<220> FEATURE:
<223> OTHER INFORMATION: Synthetic

<400> SEQUENCE: 44
cggacgacga gctcctcccc cctcccctc cgccgttgct gactgcttgg tgtcttgggc           60
ttcaaagaag                                                                 70

<210> SEQ ID NO 45
<211> LENGTH: 58
<212> TYPE: DNA
<213> ORGANISM: Artificial Sequence
<220> FEATURE:
<223> OTHER INFORMATION: Synthetic

<400> SEQUENCE: 45
cagagaagau uagcauggcc ccugcgcaag gaugacacgc aaauucgtga agcguucc    58

<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46
ccacggacga aggaatacag g                                            21

<210> SEQ ID NO 47
<211> LENGTH: 22
<212> TYPE: DNA
<213> ORGANISM: Artificial Sequence
<220> FEATURE:
<223> OTHER INFORMATION: Synthetic

<400> SEQUENCE: 47
ccacggacga tcagtctgat tt                                           22

<210> SEQ ID NO 48
<211> LENGTH: 25
<212> TYPE: DNA
<213> ORGANISM: Artificial Sequence
<220> FEATURE:
<223> OTHER INFORMATION: Synthetic

<400> SEQUENCE: 48
aggactactt ctaatctgta agagc                                        25

<210> SEQ ID NO 49
<211> LENGTH: 16
<212> TYPE: DNA
<213> ORGANISM: Artificial Sequence
<220> FEATURE:
<223> OTHER INFORMATION: Synthetic

<400> SEQUENCE: 49
gatccctgga caggcc                                                  16

<210> SEQ ID NO 50
<211> LENGTH: 23
<212> TYPE: DNA
<213> ORGANISM: Artificial Sequence
<220> FEATURE:
<223> OTHER INFORMATION: Synthetic

<400> SEQUENCE: 50
ttctgaaagg ttacttcaag gac                                          23

<210> SEQ ID NO 51
<211> LENGTH: 35
<212> TYPE: DNA
<213> ORGANISM: Artificial Sequence
<220> FEATURE:

```
<223> OTHER INFORMATION: Synthetic
<220> FEATURE:
<221> NAME/KEY: misc_feature
<222> LOCATION: (3)..(3)
<223> OTHER INFORMATION: This residue is linked to an Eclipse Quencher.

<400> SEQUENCE: 51
tctagccggt tttccggctg agacgtccgt ggcct                              35

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
gacgcggagt acaacctact                                               20

<210> SEQ ID NO 53
<211> LENGTH: 11
<212> TYPE: DNA
<213> ORGANISM: Artificial Sequence
<220> FEATURE:
<223> OTHER INFORMATION: Synthetic

<400> SEQUENCE: 53
tacaacctac t                                                        11

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
ccacggacgc acaacctact                                               20

<210> SEQ ID NO 55
<211> LENGTH: 11
<212> TYPE: DNA
<213> ORGANISM: Artificial Sequence
<220> FEATURE:
<223> OTHER INFORMATION: Synthetic

<400> SEQUENCE: 55
cacaacctac t                                                        11

<210> SEQ ID NO 56
<211> LENGTH: 21
<212> TYPE: DNA
<213> ORGANISM: Artificial Sequence
<220> FEATURE:
<223> OTHER INFORMATION: Synthetic

<400> SEQUENCE: 56
gacgcggagt atctagctgt a                                             21

<210> SEQ ID NO 57
<211> LENGTH: 12
<212> TYPE: DNA
<213> ORGANISM: Artificial Sequence
<220> FEATURE:
<223> OTHER INFORMATION: Synthetic

<400> SEQUENCE: 57
```

```
tatctagctg ta                                              12

<210> SEQ ID NO 58
<211> LENGTH: 21
<212> TYPE: DNA
<213> ORGANISM: Artificial Sequence
<220> FEATURE:
<223> OTHER INFORMATION: Synthetic

<400> SEQUENCE: 58
ccacggacga ccattatgtg c                                    21

<210> SEQ ID NO 59
<211> LENGTH: 12
<212> TYPE: DNA
<213> ORGANISM: Artificial Sequence
<220> FEATURE:
<223> OTHER INFORMATION: Synthetic

<400> SEQUENCE: 59
accattatgt gc                                              12

<210> SEQ ID NO 60
<211> LENGTH: 21
<212> TYPE: DNA
<213> ORGANISM: Artificial Sequence
<220> FEATURE:
<223> OTHER INFORMATION: Synthetic

<400> SEQUENCE: 60
gacgcggaga ccatgatgtg c                                    21

<210> SEQ ID NO 61
<211> LENGTH: 12
<212> TYPE: DNA
<213> ORGANISM: Artificial Sequence
<220> FEATURE:
<223> OTHER INFORMATION: Synthetic

<400> SEQUENCE: 61
accatgatgt gc                                              12

<210> SEQ ID NO 62
<211> LENGTH: 21
<212> TYPE: DNA
<213> ORGANISM: Artificial Sequence
<220> FEATURE:
<223> OTHER INFORMATION: Synthetic

<400> SEQUENCE: 62
ccacggacgc tgcactgtaa g                                    21

<210> SEQ ID NO 63
<211> LENGTH: 12
<212> TYPE: DNA
<213> ORGANISM: Artificial Sequence
<220> FEATURE:
<223> OTHER INFORMATION: Synthetic

<400> SEQUENCE: 63
ctgcactgta ag                                              12

<210> SEQ ID NO 64
<211> LENGTH: 21
<212> TYPE: DNA
```

```
<213> ORGANISM: Artificial Sequence
<220> FEATURE:
<223> OTHER INFORMATION: Synthetic

<400> SEQUENCE: 64
gacgcggagg cactagatgc a                                              21

<210> SEQ ID NO 65
<211> LENGTH: 12
<212> TYPE: DNA
<213> ORGANISM: Artificial Sequence
<220> FEATURE:
<223> OTHER INFORMATION: Synthetic

<400> SEQUENCE: 65
gcactagatg ca                                                        12

<210> SEQ ID NO 66
<211> LENGTH: 21
<212> TYPE: DNA
<213> ORGANISM: Artificial Sequence
<220> FEATURE:
<223> OTHER INFORMATION: Synthetic

<400> SEQUENCE: 66
gacgcggagt ccatgcaaaa c                                              21

<210> SEQ ID NO 67
<211> LENGTH: 12
<212> TYPE: DNA
<213> ORGANISM: Artificial Sequence
<220> FEATURE:
<223> OTHER INFORMATION: Synthetic

<400> SEQUENCE: 67
tccatgcaaa ac                                                        12

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
gacgcggaga tcagtctgat                                                20

<210> SEQ ID NO 69
<211> LENGTH: 11
<212> TYPE: DNA
<213> ORGANISM: Artificial Sequence
<220> FEATURE:
<223> OTHER INFORMATION: Synthetic

<400> SEQUENCE: 69
atcagtctga t                                                         11

<210> SEQ ID NO 70
<211> LENGTH: 21
<212> TYPE: DNA
<213> ORGANISM: Artificial Sequence
<220> FEATURE:
<223> OTHER INFORMATION: Synthetic

<400> SEQUENCE: 70
gacgcggagt agactgtgag c                                              21
```

```
<210> SEQ ID NO 71
<211> LENGTH: 12
<212> TYPE: DNA
<213> ORGANISM: Artificial Sequence
<220> FEATURE:
<223> OTHER INFORMATION: Synthetic

<400> SEQUENCE: 71
tagactgtga gc                                                            12

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
ccacggacgc gggacaagtg                                                    20

<210> SEQ ID NO 73
<211> LENGTH: 11
<212> TYPE: DNA
<213> ORGANISM: Artificial Sequence
<220> FEATURE:
<223> OTHER INFORMATION: Synthetic

<400> SEQUENCE: 73
cgggacaagt g                                                             11

<210> SEQ ID NO 74
<211> LENGTH: 21
<212> TYPE: DNA
<213> ORGANISM: Artificial Sequence
<220> FEATURE:
<223> OTHER INFORMATION: Synthetic

<400> SEQUENCE: 74
ccacggacgt gagtaataat g                                                  21

<210> SEQ ID NO 75
<211> LENGTH: 12
<212> TYPE: DNA
<213> ORGANISM: Artificial Sequence
<220> FEATURE:
<223> OTHER INFORMATION: Synthetic

<400> SEQUENCE: 75
tgagtaataa tg                                                            12

<210> SEQ ID NO 76
<211> LENGTH: 20
<212> TYPE: DNA
<213> ORGANISM: Artificial Sequence
<220> FEATURE:
<223> OTHER INFORMATION: Synthetic

<400> SEQUENCE: 76
ccacggacga tttgacaaac                                                    20

<210> SEQ ID NO 77
<211> LENGTH: 11
<212> TYPE: DNA
<213> ORGANISM: Artificial Sequence
<220> FEATURE:
```

<223> OTHER INFORMATION: Synthetic

<400> SEQUENCE: 77
atttgacaaa c                                                           11

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
gacgcggagt ttcagatggt                                                  20

<210> SEQ ID NO 79
<211> LENGTH: 11
<212> TYPE: DNA
<213> ORGANISM: Artificial Sequence
<220> FEATURE:
<223> OTHER INFORMATION: Synthetic

<400> SEQUENCE: 79
tttcagatgg t                                                           11

<210> SEQ ID NO 80
<211> LENGTH: 21
<212> TYPE: DNA
<213> ORGANISM: Artificial Sequence
<220> FEATURE:
<223> OTHER INFORMATION: Synthetic

<400> SEQUENCE: 80
ccacggacga gttgaagaac t                                                21

<210> SEQ ID NO 81
<211> LENGTH: 12
<212> TYPE: DNA
<213> ORGANISM: Artificial Sequence
<220> FEATURE:
<223> OTHER INFORMATION: Synthetic

<400> SEQUENCE: 81
agttgaagaa ct                                                          12

<210> SEQ ID NO 82
<211> LENGTH: 21
<212> TYPE: DNA
<213> ORGANISM: Artificial Sequence
<220> FEATURE:
<223> OTHER INFORMATION: Synthetic

<400> SEQUENCE: 82
gacgcggaga tatttacgtg c                                                21

<210> SEQ ID NO 83
<211> LENGTH: 12
<212> TYPE: DNA
<213> ORGANISM: Artificial Sequence
<220> FEATURE:
<223> OTHER INFORMATION: Synthetic

<400> SEQUENCE: 83
atatttacgt gc                                                          12

<210> SEQ ID NO 84
<211> LENGTH: 21
<212> TYPE: DNA
<213> ORGANISM: Artificial Sequence
<220> FEATURE:
<223> OTHER INFORMATION: Synthetic

<400> SEQUENCE: 84
ccacggacgg cactataagc a                                              21

<210> SEQ ID NO 85
<211> LENGTH: 12
<212> TYPE: DNA
<213> ORGANISM: Artificial Sequence
<220> FEATURE:
<223> OTHER INFORMATION: Synthetic

<400> SEQUENCE: 85
gcactataag ca                                                        12

<210> SEQ ID NO 86
<211> LENGTH: 89
<212> TYPE: DNA
<213> ORGANISM: Artificial Sequence
<220> FEATURE:
<223> OTHER INFORMATION: Synthetic

<400> SEQUENCE: 86
taataggact acttctaatc tgtaagagca gatccctgga caggcgagga atacaggtat    60
tttgtccttg aagtaacctt tcagaaatt                                      89

<210> SEQ ID NO 87
<211> LENGTH: 12
<212> TYPE: DNA
<213> ORGANISM: Artificial Sequence
<220> FEATURE:
<223> OTHER INFORMATION: Synthetic

<400> SEQUENCE: 87
atcacgatta gc                                                        12

<210> SEQ ID NO 88
<211> LENGTH: 21
<212> TYPE: DNA
<213> ORGANISM: Artificial Sequence
<220> FEATURE:
<223> OTHER INFORMATION: Synthetic

<400> SEQUENCE: 88
gacgcggagt gcgatttctg t                                              21

<210> SEQ ID NO 89
<211> LENGTH: 12
<212> TYPE: DNA
<213> ORGANISM: Artificial Sequence
<220> FEATURE:
<223> OTHER INFORMATION: Synthetic

<400> SEQUENCE: 89
tgcgatttct gt                                                        12

<210> SEQ ID NO 90
<211> LENGTH: 21
<212> TYPE: DNA
<213> ORGANISM: Artificial Sequence
<220> FEATURE:

<223> OTHER INFORMATION: Synthetic

<400> SEQUENCE: 90
gacgcggagc caggaaggtc t                                                21

<210> SEQ ID NO 91
<211> LENGTH: 12
<212> TYPE: DNA
<213> ORGANISM: Artificial Sequence
<220> FEATURE:
<223> OTHER INFORMATION: Synthetic

<400> SEQUENCE: 91
ccaggaaggt ct                                                          12

<210> SEQ ID NO 92
<211> LENGTH: 21
<212> TYPE: DNA
<213> ORGANISM: Artificial Sequence
<220> FEATURE:
<223> OTHER INFORMATION: Synthetic

<400> SEQUENCE: 92
gacgcggagg cctaatgaag a                                                21

<210> SEQ ID NO 93
<211> LENGTH: 12
<212> TYPE: DNA
<213> ORGANISM: Artificial Sequence
<220> FEATURE:
<223> OTHER INFORMATION: Synthetic

<400> SEQUENCE: 93
gcctaatgaa ga                                                          12

<210> SEQ ID NO 94
<211> LENGTH: 21
<212> TYPE: DNA
<213> ORGANISM: Artificial Sequence
<220> FEATURE:
<223> OTHER INFORMATION: Synthetic

<400> SEQUENCE: 94
gacgcggagc aagggaaaag c                                                21

<210> SEQ ID NO 95
<211> LENGTH: 12
<212> TYPE: DNA
<213> ORGANISM: Artificial Sequence
<220> FEATURE:
<223> OTHER INFORMATION: Synthetic

<400> SEQUENCE: 95
caagggaaaa gc                                                          12

<210> SEQ ID NO 96
<211> LENGTH: 21
<212> TYPE: DNA
<213> ORGANISM: Artificial Sequence
<220> FEATURE:
<223> OTHER INFORMATION: Synthetic

<400> SEQUENCE: 96
gacgcggaga ggattatgac a                                                21

```
<210> SEQ ID NO 97
<211> LENGTH: 12
<212> TYPE: DNA
<213> ORGANISM: Artificial Sequence
<220> FEATURE:
<223> OTHER INFORMATION: Synthetic

<400> SEQUENCE: 97
aggattatga ca                                                          12

<210> SEQ ID NO 98
<211> LENGTH: 21
<212> TYPE: DNA
<213> ORGANISM: Artificial Sequence
<220> FEATURE:
<223> OTHER INFORMATION: Synthetic

<400> SEQUENCE: 98
gacgcggagg aaacgatgtg c                                                21

<210> SEQ ID NO 99
<211> LENGTH: 12
<212> TYPE: DNA
<213> ORGANISM: Artificial Sequence
<220> FEATURE:
<223> OTHER INFORMATION: Synthetic

<400> SEQUENCE: 99
gaaacgatgt gc                                                          12

<210> SEQ ID NO 100
<211> LENGTH: 20
<212> TYPE: DNA
<213> ORGANISM: Artificial Sequence
<220> FEATURE:
<223> OTHER INFORMATION: Synthetic

<400> SEQUENCE: 100
gcgcgtccca ctgcagaggt                                                  20

<210> SEQ ID NO 101
<211> LENGTH: 12
<212> TYPE: DNA
<213> ORGANISM: Artificial Sequence
<220> FEATURE:
<223> OTHER INFORMATION: Synthetic

<400> SEQUENCE: 101
cactgcagag gt                                                          12

<210> SEQ ID NO 102
<211> LENGTH: 20
<212> TYPE: DNA
<213> ORGANISM: Artificial Sequence
<220> FEATURE:
<223> OTHER INFORMATION: Synthetic

<400> SEQUENCE: 102
gcgcgtcccc accttgagat                                                  20

<210> SEQ ID NO 103
<211> LENGTH: 12
<212> TYPE: DNA
<213> ORGANISM: Artificial Sequence
<220> FEATURE:
<223> OTHER INFORMATION: Synthetic
```

```
<400> SEQUENCE: 103
ccaccttgag at                                                          12

<210> SEQ ID NO 104
<211> LENGTH: 21
<212> TYPE: DNA
<213> ORGANISM: Artificial Sequence
<220> FEATURE:
<223> OTHER INFORMATION: Synthetic

<400> SEQUENCE: 104
gacgcggaga ctccttggca a                                                21

<210> SEQ ID NO 105
<211> LENGTH: 12
<212> TYPE: DNA
<213> ORGANISM: Artificial Sequence
<220> FEATURE:
<223> OTHER INFORMATION: Synthetic

<400> SEQUENCE: 105
actccttggc aa                                                          12

<210> SEQ ID NO 106
<211> LENGTH: 21
<212> TYPE: DNA
<213> ORGANISM: Artificial Sequence
<220> FEATURE:
<223> OTHER INFORMATION: Synthetic

<400> SEQUENCE: 106
gacgcggagc tccctggtta c                                                21

<210> SEQ ID NO 107
<211> LENGTH: 12
<212> TYPE: DNA
<213> ORGANISM: Artificial Sequence
<220> FEATURE:
<223> OTHER INFORMATION: Synthetic

<400> SEQUENCE: 107
ctccctggtt ac                                                          12

<210> SEQ ID NO 108
<211> LENGTH: 21
<212> TYPE: DNA
<213> ORGANISM: Artificial Sequence
<220> FEATURE:
<223> OTHER INFORMATION: Synthetic

<400> SEQUENCE: 108
gacgcggagg tcaaggtcct t                                                21

<210> SEQ ID NO 109
<211> LENGTH: 12
<212> TYPE: DNA
<213> ORGANISM: Artificial Sequence
<220> FEATURE:
<223> OTHER INFORMATION: Synthetic

<400> SEQUENCE: 109
gtcaaggtcc tt                                                          12

<210> SEQ ID NO 110
<211> LENGTH: 21
```

```
<212> TYPE: DNA
<213> ORGANISM: Artificial Sequence
<220> FEATURE:
<223> OTHER INFORMATION: Synthetic

<400> SEQUENCE: 110
gacgcggagg ttgcaataca g                                              21

<210> SEQ ID NO 111
<211> LENGTH: 12
<212> TYPE: DNA
<213> ORGANISM: Artificial Sequence
<220> FEATURE:
<223> OTHER INFORMATION: Synthetic

<400> SEQUENCE: 111
gttgcaatac ag                                                        12

<210> SEQ ID NO 112
<211> LENGTH: 21
<212> TYPE: DNA
<213> ORGANISM: Artificial Sequence
<220> FEATURE:
<223> OTHER INFORMATION: Synthetic

<400> SEQUENCE: 112
gacgcggagc agaatgtcaa c                                              21

<210> SEQ ID NO 113
<211> LENGTH: 12
<212> TYPE: DNA
<213> ORGANISM: Artificial Sequence
<220> FEATURE:
<223> OTHER INFORMATION: Synthetic

<400> SEQUENCE: 113
cagaatgtca ac                                                        12

<210> SEQ ID NO 114
<211> LENGTH: 21
<212> TYPE: DNA
<213> ORGANISM: Artificial Sequence
<220> FEATURE:
<223> OTHER INFORMATION: Synthetic

<400> SEQUENCE: 114
gacgcggagg caaatccttg g                                              21

<210> SEQ ID NO 115
<211> LENGTH: 12
<212> TYPE: DNA
<213> ORGANISM: Artificial Sequence
<220> FEATURE:
<223> OTHER INFORMATION: Synthetic

<400> SEQUENCE: 115
gcaaatcctt gg                                                        12

<210> SEQ ID NO 116
<211> LENGTH: 21
<212> TYPE: DNA
<213> ORGANISM: Artificial Sequence
<220> FEATURE:
<223> OTHER INFORMATION: Synthetic

<400> SEQUENCE: 116
```

```
gacgcggaga ttgctgatgg t                                              21
```

<210> SEQ ID NO 117
<211> LENGTH: 12
<212> TYPE: DNA
<213> ORGANISM: Artificial Sequence
<220> FEATURE:
<223> OTHER INFORMATION: Synthetic

<400> SEQUENCE: 117

```
attgctgatg gt                                                        12
```

<210> SEQ ID NO 118
<211> LENGTH: 20
<212> TYPE: DNA
<213> ORGANISM: Artificial Sequence
<220> FEATURE:
<223> OTHER INFORMATION: Synthetic

<400> SEQUENCE: 118

```
cgccgaggag tccatgccat                                                20
```

<210> SEQ ID NO 119
<211> LENGTH: 12
<212> TYPE: DNA
<213> ORGANISM: Artificial Sequence
<220> FEATURE:
<223> OTHER INFORMATION: Synthetic

<400> SEQUENCE: 119

```
agtccatgcc at                                                        12
```

<210> SEQ ID NO 120
<211> LENGTH: 20
<212> TYPE: DNA
<213> ORGANISM: Artificial Sequence
<220> FEATURE:
<223> OTHER INFORMATION: Synthetic

<400> SEQUENCE: 120

```
gcgcgtccca ccaagctcat                                                20
```

<210> SEQ ID NO 121
<211> LENGTH: 12
<212> TYPE: DNA
<213> ORGANISM: Artificial Sequence
<220> FEATURE:
<223> OTHER INFORMATION: Synthetic

<400> SEQUENCE: 121

```
caccaagctc at                                                        12
```

<210> SEQ ID NO 122
<211> LENGTH: 20
<212> TYPE: DNA
<213> ORGANISM: Artificial Sequence
<220> FEATURE:
<223> OTHER INFORMATION: Synthetic

<400> SEQUENCE: 122

```
gcgcgtccat tgcaggtctg                                                20
```

<210> SEQ ID NO 123
<211> LENGTH: 12
<212> TYPE: DNA
<213> ORGANISM: Artificial Sequence -continued
<220> FEATURE:
<223> OTHER INFORMATION: Synthetic

<400> SEQUENCE: 123
attgcaggtc tg                                                        12

<210> SEQ ID NO 124
<211> LENGTH: 21
<212> TYPE: DNA
<213> ORGANISM: Artificial Sequence
<220> FEATURE:
<223> OTHER INFORMATION: Synthetic

<400> SEQUENCE: 124
gacgcggaga agaactgttg c                                              21

<210> SEQ ID NO 125
<211> LENGTH: 12
<212> TYPE: DNA
<213> ORGANISM: Artificial Sequence
<220> FEATURE:
<223> OTHER INFORMATION: Synthetic

<400> SEQUENCE: 125
aagaactgtt gc                                                        12

<210> SEQ ID NO 126
<211> LENGTH: 21
<212> TYPE: DNA
<213> ORGANISM: Artificial Sequence
<220> FEATURE:
<223> OTHER INFORMATION: Synthetic

<400> SEQUENCE: 126
gacgcggagt gaagaacacc t                                              21

<210> SEQ ID NO 127
<211> LENGTH: 12
<212> TYPE: DNA
<213> ORGANISM: Artificial Sequence
<220> FEATURE:
<223> OTHER INFORMATION: Synthetic

<400> SEQUENCE: 127
tgaagaacac ct                                                        12

<210> SEQ ID NO 128
<211> LENGTH: 21
<212> TYPE: DNA
<213> ORGANISM: Artificial Sequence
<220> FEATURE:
<223> OTHER INFORMATION: Synthetic

<400> SEQUENCE: 128
gacgcggagg cgtcgattat c                                              21

<210> SEQ ID NO 129
<211> LENGTH: 12
<212> TYPE: DNA
<213> ORGANISM: Artificial Sequence
<220> FEATURE:
<223> OTHER INFORMATION: Synthetic

<400> SEQUENCE: 129
gcgtcgatta tc                                                        12

<210> SEQ ID NO 130
<211> LENGTH: 18
<212> TYPE: DNA
<213> ORGANISM: Artificial Sequence
<220> FEATURE:
<223> OTHER INFORMATION: Synthetic

<400> SEQUENCE: 130
cacggtccag cgacaagt                                                 18

<210> SEQ ID NO 131
<211> LENGTH: 12
<212> TYPE: DNA
<213> ORGANISM: Artificial Sequence
<220> FEATURE:
<223> OTHER INFORMATION: Synthetic

<400> SEQUENCE: 131
aaggaataca gg                                                       12

<210> SEQ ID NO 132
<211> LENGTH: 19
<212> TYPE: DNA
<213> ORGANISM: Artificial Sequence
<220> FEATURE:
<223> OTHER INFORMATION: Synthetic

<400> SEQUENCE: 132
ccagtgccga actgcagtg                                                19

<210> SEQ ID NO 133
<211> LENGTH: 12
<212> TYPE: DNA
<213> ORGANISM: Artificial Sequence
<220> FEATURE:
<223> OTHER INFORMATION: Synthetic

<400> SEQUENCE: 133
gaggaataca gg                                                       12

<210> SEQ ID NO 134
<211> LENGTH: 12
<212> TYPE: DNA
<213> ORGANISM: Artificial Sequence
<220> FEATURE:
<223> OTHER INFORMATION: Synthetic

<400> SEQUENCE: 134
ctgttccgtc ag                                                       12

<210> SEQ ID NO 135
<211> LENGTH: 12
<212> TYPE: DNA
<213> ORGANISM: Artificial Sequence
<220> FEATURE:
<223> OTHER INFORMATION: Synthetic

<400> SEQUENCE: 135
gagcctcaat gc                                                       12

<210> SEQ ID NO 136
<211> LENGTH: 20
<212> TYPE: DNA
<213> ORGANISM: Artificial Sequence
<220> FEATURE:
<223> OTHER INFORMATION: Synthetic

```
<400> SEQUENCE: 136
cgccgaggaa gcctcaatgc                                                   20

<210> SEQ ID NO 137
<211> LENGTH: 12
<212> TYPE: DNA
<213> ORGANISM: Artificial Sequence
<220> FEATURE:
<223> OTHER INFORMATION: Synthetic

<400> SEQUENCE: 137
aagcctcaat gc                                                           12

<210> SEQ ID NO 138
<211> LENGTH: 21
<212> TYPE: DNA
<213> ORGANISM: Artificial Sequence
<220> FEATURE:
<223> OTHER INFORMATION: Synthetic

<400> SEQUENCE: 138
gacgcggagc gttttaaatc a                                                 21

<210> SEQ ID NO 139
<211> LENGTH: 12
<212> TYPE: DNA
<213> ORGANISM: Artificial Sequence
<220> FEATURE:
<223> OTHER INFORMATION: Synthetic

<400> SEQUENCE: 139
cgttttaaat ca                                                           12

<210> SEQ ID NO 140
<211> LENGTH: 21
<212> TYPE: DNA
<213> ORGANISM: Artificial Sequence
<220> FEATURE:
<223> OTHER INFORMATION: Synthetic

<400> SEQUENCE: 140
ccacggacgc tgttccgtca g                                                 21

<210> SEQ ID NO 141
<211> LENGTH: 20
<212> TYPE: DNA
<213> ORGANISM: Artificial Sequence
<220> FEATURE:
<223> OTHER INFORMATION: Synthetic

<400> SEQUENCE: 141
gacgcggaga tacaacctac                                                   20

<210> SEQ ID NO 142
<211> LENGTH: 44
<212> TYPE: DNA
<213> ORGANISM: Artificial Sequence
<220> FEATURE:
<223> OTHER INFORMATION: Synthetic

<400> SEQUENCE: 142
ccagtgccga tgaggtagta ggttgtatag ttcgctggac cgtg                        44

<210> SEQ ID NO 143
```

-continued

```
<211> LENGTH: 17
<212> TYPE: DNA
<213> ORGANISM: Artificial Sequence
<220> FEATURE:
<223> OTHER INFORMATION: Synthetic

<400> SEQUENCE: 143
cacggtccag cgaacta                                                        17

<210> SEQ ID NO 144
<211> LENGTH: 19
<212> TYPE: DNA
<213> ORGANISM: Artificial Sequence
<220> FEATURE:
<223> OTHER INFORMATION: Synthetic

<400> SEQUENCE: 144
gacgcggagt acaacctac                                                      19

<210> SEQ ID NO 145
<211> LENGTH: 18
<212> TYPE: DNA
<213> ORGANISM: Artificial Sequence
<220> FEATURE:
<223> OTHER INFORMATION: Synthetic

<400> SEQUENCE: 145
cacggtccag cgaactat                                                       18

<210> SEQ ID NO 146
<211> LENGTH: 18
<212> TYPE: DNA
<213> ORGANISM: Artificial Sequence
<220> FEATURE:
<223> OTHER INFORMATION: Synthetic

<400> SEQUENCE: 146
gacgcggagt gggccacc                                                       18

<210> SEQ ID NO 147
<211> LENGTH: 21
<212> TYPE: DNA
<213> ORGANISM: Artificial Sequence
<220> FEATURE:
<223> OTHER INFORMATION: Synthetic

<400> SEQUENCE: 147
agacaragcg ggtccatccc y                                                   21

<210> SEQ ID NO 148
<211> LENGTH: 76
<212> TYPE: DNA
<213> ORGANISM: Artificial Sequence
<220> FEATURE:
<223> OTHER INFORMATION: Synthetic

<400> SEQUENCE: 148
acgtacacgt gatactgaga caaagcgggt ccatccctgg gccacctctc gagggccacc         60
gcgtccaaca ccagca                                                         76

<210> SEQ ID NO 149
<211> LENGTH: 21
<212> TYPE: DNA
<213> ORGANISM: Artificial Sequence
<220> FEATURE:
<223> OTHER INFORMATION: Synthetic
```

```
<400> SEQUENCE: 149
ccacggacga tcagtctgat t                                              21

<210> SEQ ID NO 150
<211> LENGTH: 20
<212> TYPE: DNA
<213> ORGANISM: Artificial Sequence
<220> FEATURE:
<223> OTHER INFORMATION: Synthetic

<400> SEQUENCE: 150
ccacggacga tcagtctgat                                                20

<210> SEQ ID NO 151
<211> LENGTH: 21
<212> TYPE: DNA
<213> ORGANISM: Artificial Sequence
<220> FEATURE:
<223> OTHER INFORMATION: Synthetic

<400> SEQUENCE: 151
ccacggacga tcagtctgat a                                              21

<210> SEQ ID NO 152
<211> LENGTH: 20
<212> TYPE: DNA
<213> ORGANISM: Artificial Sequence
<220> FEATURE:
<223> OTHER INFORMATION: Synthetic

<400> SEQUENCE: 152
ccacggacgg aaggcactttt                                               20

<210> SEQ ID NO 153
<211> LENGTH: 19
<212> TYPE: DNA
<213> ORGANISM: Artificial Sequence
<220> FEATURE:
<223> OTHER INFORMATION: Synthetic

<400> SEQUENCE: 153
ccacggacgg aaggcactt                                                 19

<210> SEQ ID NO 154
<211> LENGTH: 20
<212> TYPE: DNA
<213> ORGANISM: Artificial Sequence
<220> FEATURE:
<223> OTHER INFORMATION: Synthetic

<400> SEQUENCE: 154
ccacggacgg aaggcacttg                                                20

<210> SEQ ID NO 155
<211> LENGTH: 20
<212> TYPE: RNA
<213> ORGANISM: Artificial Sequence
<220> FEATURE:
<223> OTHER INFORMATION: Synthetic

<400> SEQUENCE: 155
acugcaguga aggcacuugu                                                20
```

METHODS FOR ANALYSIS OF NUCLEIC ACID MOLECULES DURING AMPLIFICATION REACTIONS

The present application is a divisional of U.S. application Ser. No. 12/404,240, filed Mar. 13, 2009, which claims priority to U.S. Provisional Application Ser. No. 61/036,953, filed Mar. 15, 2008, each of which is incorporated herein by reference.

FIELD OF THE INVENTION

The present invention provides systems, methods and kits for performing amplification reactions in combination with a detection assay (e.g., cleavage assay), where the detection assay employs probes with relatively short (e.g., 6-12 bases) analyte-specific regions ("ASRs") to provide a minimum amount of recognizable duplex for a nucleic acid modifying enzyme (e.g., a FEN-1 endonuclease). In some embodiments, such assays are used for target quantification, and in other embodiments, such assays are used for genotyping. In certain embodiments, the use of such short probes allows for assays with increased dynamic range.

BACKGROUND

The quantification of nucleic acids plays an important role in the fields of biology and medicine. For example, quantification of nucleic acid is important in cancer diagnosis and prognosis and viral diagnosis and judgments of therapeutic effects (e.g., for HCV and HIV). HCV RNA quantification is important for patients taking IFN. The effect of IFN therapy can be directly found by monitoring the amount of virus during IFN therapy. This enables more effective IFN therapy that is tailored to clinical conditions of each patient. Quantification of target nucleic acid is important for diagnosis of diseases in the future. For example, earlier diagnosis can be effected by examining the expression level of mRNA that responds to exogenous stimuli in the case of a disease that results from exogenous stimuli.

The polymerase chain reaction can be employed for nucleic acid quantification. However, when PCR is employed, the absolute amount of the amplified nucleic acids does not accurately reflect the amount of the target nucleic acid that had existed when amplification was initiated. At first, the amount of the product amplified by PCR generally exponentially increases every cycle, however, the rate of increase slows down and then stops when the amount of the amplified product exceeds a certain level. Thus, the final amount of the amplified product is constant regardless of the amount of the target nucleic acid when the reaction was initiated. This phenomenon is referred to as the plateau effect, which should be taken into consideration when quantifying the product amplified by PCR.

A technique known as "real time" PCR is widely employed for target sequence quantification (see, e.g., Bustin, Journal of Molecular Endocrinology (2000) 25, 169-193; Bustin and Nolan, Journal of Biomolecular Techniques 15:155-166; ABI "Essentials of Real Time PCR" Part Number 4371089 Revision A; ABI Primer Express Software 3.0 "Getting Started Guide" Part Number 4362460 Rev. B, January 2005). In this technique, a calibration curve for each amplification target is first prepared. A serial dilution of the target nucleic acid is prepared, each sample is subjected to PCR, and the accumulation of product is detected in real time, i.e., during the course of the amplification, generally by the detection of a signal (e.g., fluorescence) that accumulates in proportion to the amount of amplified material. The threshold cycle (the Ct value), the cycle at which the signal specific to the amplified product is first detected above background fluorescence or the "baseline" is determined. The Ct values for the different dilutions in the series is plotted on a vertical axis, and the initial copy number of the target nucleic acids in each dilution is plotted on a horizontal axis to produce the calibration curve for that target material. An unknown sample of interest (e.g., a sample suspected of containing the same target material in an unknown amount) is subjected to PCR under the same conditions and the Ct value for the unknown is determined. The calibration curve for that target is then used to determine the initial copy number for the unknown sample.

There are two types of homogeneous fluorescent reporting methods generally used. "Nonspecific" detection indicates the accumulation of amplified product but is not specific for a correct or intended amplicon, while "specific" detection methods verify the accumulation of a particular intended product. Nonspecific detection can use intercalating dyes, such as ethidium bromide or SYBR Green, which bind to any double-stranded DNA generated during the PCR reaction and emit enhanced fluorescence. Such dyes are added to the PCR reagents prior to thermocycling. Although intrinsically non-specific, DNA melt curves can used to check the identity of the amplification products The advantages of using dye intercalation methods include that 1) the dyes an be used to monitor the amplification of any double-stranded DNA sequence, and 2) no probe is required, which reduces assay setup and running costs.

The primary disadvantage of using intercalating dyes as the reaction reporting method is that they dyes may generate false positive signals; i.e., because the dye binds to any double-stranded DNA without sequence selectivity, they give signal in the presence of nonspecific double-stranded DNA. Non-specific DNA may include contaminating DNA, "primer dimer" artifact DNA, or any DNA other than the intended target that was able to amplify using the primers provided in the reaction.

In addition to the non-specificity, intercalating dyes can make quantification of even correct target more complex because the amount of signal is dependent on the mass of double-stranded DNA produced in the reaction amplification, not the number of copies of the product. A longer amplified product has greater mass and can bind more dye molecules and thus can generate more signal than the same number of copies of a shorter product. In contrast, when a fluorogenic probe is used, a single fluorophore is released from quenching for each copy of the amplified molecule, regardless of the length of the amplicon.

Template or target-specific analysis generally requires the design and synthesis of one or more custom-made fluorescent probes for each PCR assay. Because the primer sequences are incorporated into correct and incorrect amplification product alike, probes are generally designed to hybridize to a region of the target sequence that is between the primers, such that successful probe hybridization confirms that the intended target sequence was amplified. Most reporting systems utilize fluorescent resonance energy transfer (FRET) or similar interactions between donor and quencher molecules as the basis of detection. Generally, a fluorescent signal is only generated if the amplicon-specific probe hybridizes to its complementary target. In common embodiments such as the TAQMAN and other 5' nuclease detection assays, the 5' nuclease cleaves the hybridized probe to separate the fluorophore from the quencher molecule. In some reaction designs, though, the probes are not cleaved, but change conformation in the presence of the correct target. Such a change in probe conformation separates the fluorophore from the quencher molecule, providing the increased fluorescence that is indicative of successful amplification of the specific target.

Specific chemistries are advantageous in that nonspecific amplification, e.g., due to mispriming or primer-dimer artifacts, does not generate a signal and is ignored by the fluorescence detector. This obviates the need for post-PCR Southern blotting, sequence analysis, or melt curves to confirm the identity of the amplicon. Another advantage over intercalating dyes is that the probes can be labeled with different, distinguishable reporter dyes that allow the detection of amplification products from several distinct sequences in a single PCR reaction (multiplex). One primary disadvantage of probe-based specific detection chemistries are that synthesis of different probes is required for each different sequence to be detected. (ABI "Essentials of Real Time PCR" Part Number 4371089 Revision A). The need to use different custom probes labeled with expensive dye, and quencher moieties, and optional with minor groove binders as well, adds a significant level of additional expense to probe based, amplicon-specific real time PCR analysis. Another disadvantage is the difficulty in distinguishing closely related sequences. Allele discrimination using PCR and hydrolysis probes generally involves the use of either a primer that has a mismatched 3' end when hybridized to the 'wrong' target (e.g. a primer intended to amplify one allele, when hybridized to an allele that it is not intended to amplify) such that amplification of the allele is impeded, or hydrolysis probes designed to anneal poorly to the unintended allele. Both approaches offer imperfect discrimination, as both primer extension and probe cleavage can occur even when such mismatches are present.

In light of the above, what is needed are relatively simple and inexpensive homogeneous methods for quantitating nucleic acids in a target-specific fashion, in real time.

SUMMARY OF THE INVENTION

In some embodiments, the present invention provides detection technologies for analyzing a target nucleic acid of interest. As described herein, the detection technologies include real time detection capability that, if desired, can be quantitative or semi-quantitative. Systems, compositions (e.g., kits, reaction mixtures, and the like), and methods are provided. The systems, compositions, and methods may be used in combination with other known or future developed technologies. In some embodiments, the present invention provides detection systems comprising the use of footprint probes, wherein the footprint probe provides, e.g., a minimum structure (e.g., duplex) needed for detection using a detection enzyme.

In some embodiments, the invention provides a method of analyzing a target nucleic acid, comprising selecting a 5' nuclease, wherein the 5' nuclease recognizes a structure comprising a nucleic acid duplex, determining a footprint duplex length for the 5' nuclease, amplifying a target nucleic acid in the presence of a synthetic footprint probe and the 5' nuclease under conditions such that the synthetic footprint probe is cleaved during a target amplification reaction to generate cleaved fragments, wherein the synthetic footprint probe comprises an analyte-specific portion and a non-target portion, wherein the non-target potion is substantially non-complementary to said target nucleic acid and wherein the analyte-specific portion forms a probe-target duplex with said target nucleic acid that is no longer than the footprint duplex length for the 5' nuclease enzyme. In preferred embodiments, the method further comprises detecting the cleaved fragments during the amplification reaction. In particularly preferred embodiments, the target amplification reaction is a polymerase chain reaction. In preferred embodiments, the 5' nuclease is selected from the group consisting of a natural FEN-1 endonuclease, a modified FEN-1 endonuclease, and a chimerical protein comprising at least a portion of at least one FEN-1 endonuclease.

In some embodiments, the present invention provides a method of analyzing a target nucleic acid, comprising: a) amplifying a target nucleic acid in the presence of a synthetic probe and a FEN-1 endonuclease under conditions such that the synthetic probe is cleaved during an amplification reaction to generate cleaved fragments; wherein the synthetic probe is a footprint probe for the FEN-1 endonuclease, the footprint probe comprising an analyte-specific portion and a non-target portion, wherein the non-target potion is substantially non-complementary to said target nucleic acid and wherein, if the amplification reaction is an isothermal reaction, the analyte-specific portion of the footprint probe has a calculated $T_m$ with the target that is at least 5° C. below, more preferably 8° degrees below, and still more preferably 10° C. below the temperature at which said isothermal reaction is conducted, or in embodiments in which the amplification reaction is a thermal cycling reaction, the analyte-specific portion of the footprint probe has a calculated $T_m$ with said target that is at least 5° C. below, more preferably 8° degrees below, and still more preferably 10° C. below the lowest temperature used in said thermal cycling, and wherein the footprint probe does not comprise a minor groove binder moiety. In preferred embodiments, the method further comprises detecting the cleaved fragments during said amplification reaction.

In particularly preferred embodiments, the invention provides methods comprising the use of a nucleic acid amplification assay and a detection assay, wherein at least one of the amplification assay or the detection assay comprises the use of a footprint probe having an analyte-specific region of 12 or fewer nucleotides, and further comprises the use of a 5' nuclease (e.g., a FEN-1 nuclease of an archaeon or eukaryote, or 5' nuclease of virus or of a eubacterial DNA polymerase). In some embodiments, the ASR of the footprint probe contains 12 nucleotides that are completely complementary to a target nucleic acid, while in some embodiments, the ASR of the probe contains 12 nucleotides, one or more of which is not complementary to a corresponding nucleotide in a target nucleic acid strand.

In some embodiments, the present invention provides methods of analyzing a target nucleic acid, comprising: a) amplifying a target nucleic acid in the presence of a probe and an endonuclease under conditions such that the probe is cleaved during an amplification reaction to generate cleaved fragments; wherein the probe comprises an analyte-specific portion, i.e., a target binding region, and a non-target portion, wherein the non-target potion is substantially non-complementary to the target nucleic acid and wherein the target binding portion contains no more than 12 nucleotides that are complementary to the target nucleic acid; and b) detecting the cleaved fragments during said amplification reaction. In some embodiments, the probe is a synthetic probe. In some embodiments, the endonuclease is a FEN-1 endonuclease (e.g., a thermostable FEN-1 endonuclease, including, but not limited to FEN-1 endonucleases from an archaeal species).

The methods are not limited by the nature of the analysis that is conducted. In some embodiments, the analyzing comprises detecting the presence of the target nucleic acid by detecting the cleaved fragments during the amplification reaction. In some embodiments, the analyzing comprises identifying the presence of a polymorphism (e.g., a single-nucleotide polymorphism, a deletion, an insertion, a repeat sequence, and the like) in the target nucleic acid. In some embodiments, the analyzing comprises determining an identity of an organism from which the target nucleic acid is derived. For example, in some embodiments the organism is identified at the level of the kingdom, phylum, class, order, family, genus, species, sub-species, or individual levels. In some embodiments, the analyzing comprises detecting the amount of the target nucleic acid. In some embodiments, the detected amount is the amount of the target nucleic acid initially present in a sample.

The present invention is not limited by the source of or nature of the target nucleic acid. In some embodiments, the target nucleic acid is isolated from a sample. The present invention is not limited by the nature of the sample. Samples include, but are not limited to, cell samples (e.g., from an organism, cultured cells, stem cells, tumor cells, pathogens, single-celled organisms), tissue samples, fluid samples (e.g., blood, serum, plasma, urine, saliva, and the like), a culture sample, and an environmental sample. Target nucleic acids may be derived from an organism, including, but not limited to, an animal (e.g., a mammal such as a human), a plant, a bacteria, a virus, and a fungi. The target nucleic may comprise DNA or RNA or combinations thereof. The target nucleic acid may comprise natural nucleic acid molecules or synthetic nucleic acid molecules, or combinations thereof. In some embodiments, where the target nucleic is or comprises RNA, the RNA is converted to DNA, for example, by reverse transcription with a reverse transcriptase enzyme. The target nucleic acid may include covalent or non-covalent modifications to one or more nucleotides or other parts of its structure. For example, in some embodiments, the nucleic acid is methylated at one or more nucleotides and the analysis includes determining the existence of, degree of, or location or methylated nucleotides in the target nucleic acid.

In some embodiments, the amplification reaction employed by the methods is a polymerase chain reaction, although other temperature cycling or isothermal amplification technologies may be employed. Many of the amplification technologies employ a polymerase. In some embodiments, the polymerase is a thermostable polymerase. In some embodiments, the polymerase lacks 5' to 3' exonuclease activity. Many of the amplification technologies employ one or more primers. Accordingly, in some embodiments, the methods utilize first and second primer oligonucleotides. Additional primer oligonucleotides may also be used, as needed or desired.

In some embodiments, the probe cleavage is achieved by forming cleavage structure and cleaving the cleavage structure. In some embodiments, a cleavage structure is formed before the probe is cleaved, wherein the cleavage structure is formed by association of the target nucleic acid with: a) the probe at a first region of the target nucleic acid; and b) a second oligonucleotide that associates with a second region of the target nucleic, wherein the second region is 3' of the first region along the length of the target nucleic acid. In some embodiments, the first and second regions of the target nucleic acid are contiguous with one another. In some embodiments, at least one nucleotide at the 3' end of the second oligonucleotide, in the cleavage structure, overlaps with a region of hybridization between the probe and the target nucleic acid. In some embodiments, the 3' terminal nucleotide of the second oligonucleotide is not complementary to the target nucleic acid, in the cleavage structure. In some embodiments, the second oligonucleotide is also a primer used in the amplifying step.

In some embodiments, the cleavage structure is a structure or employs reagents or approaches described in one or more of: U.S. Pat. Nos. 7,312,033, 7,306,917, 7,297,780, 7,273,696, 7,256,020, 7,195,871, 7,150,982, 7,101,672, 7,087,381, 7,067,643, 7,060,436, 7,045,289, 7,011,944, 6,932,943, 6,913,881, 6,875,572, 6,872,816, 6,780,982, 6,780,585, 6,759,226, 6,709,819, 6,709,815, 6,706,471, 6,692,917, 6,673,616, 6,635,463, 6,562,611, 6,555,357, 6,458,535, 6,372,424, 6,358,691, 6,355,437, 6,348,314, 6,214,545, 6,194,149, 6,090,606, 6,090,543, 6,001,567, 5,994,069, 5,985,557, 5,888,780, 5,846,717, 5,843,669, 5,843,654, 5,837,450, 5,719,028, 5,614,402, and 5,541,311 and U.S. Publ. Nos.: 20080015349, 20080014124, 20070292856, 20070207455, 20070202517, 20070111200, 20070087345, 20070049745, 20060252032, 20060246475, 20060240452, 20060199202, 20060183207, 20060160074, 20060147955, 20060147938, 20050277138, 20050196750, 20050186588, 20050181435, 20050164177, 20050158716, 20050130179, 20050106596, 20050074788, 20050048527, 20040219576, 20040203035, 20040096874, 20040014067, 20030219784, 20030143535, 20030134349, 20030124526, 20030113237, 20030113236, 20030104470, 20030104378, 20030092039, 20030082544, 20030072689, 20020156255, 20020142454, and 20020128465, each of which is herein incorporated by reference in its entirety. These patents and published applications also describe enzymes, design, manufacture, and detection systems, and other components useful in the methods, compositions, and systems of the invention.

In some embodiments, the target binding portion of the probe contains no more than 11 (e.g., 10, 9, 8, 7, 6, etc.) nucleotides that are complementary to said target nucleic acid. In some embodiments, the probe is labeled. In other embodiments, the probe is unlabeled. In some embodiments, the probe does not contain non-natural nucleotides. In some embodiments, the probe consists of naturally occurring nucleotides. In some embodiments, the probe has a moiety at its 3' end that prevents extension of the probe by a polymerase. The non-target portion of the probe may be any desired length. In some embodiments, it is a single nucleotide. In other embodiments, it is two or more (e.g., 3, 4, 5, 6, 7, 8, 9, 10, 11, 12, 13, 14, 15, 16, 17, 18, 19, 20, 21, 22, 23, 24, 25, 26, 27, 28, 29, 30, ..., 40, ... 50, ..., etc.) nucleotides in length.

In some embodiments, the detecting step utilizes a detection oligonucleotide. For example, in some embodiments, the detecting of the cleaved fragments comprises associating one or more of said cleaved fragments with a synthetic detection oligonucleotide. In some embodiments, the synthetic detection oligonucleotide has a region of self-complementarity that forms a hairpin structure. In some embodiments, the synthetic detection oligonucleotide comprises a label (e.g., a fluorescent label). In some embodiments, the synthetic detection oligonucleotide further comprises a fluorescent quencher moiety. In some embodiments, the cleaved flaps are detected by extension of the cleaved flaps, using the detection oligonucleotide as a template. In some embodiments, the cleaved flaps are detected by ligation of the cleaved flaps to another molecule, using the detection oligonucleotide as a template. In some embodiments, the cleaved fragments, when associated with the synthetic detection oligonucleotide, form a cleavage structure that is cleavable by the FEN-1 endonuclease. In some embodiments, the detecting comprises cleaving the cleavage structure (that comprises the synthetic detection oligonucleotide) to generate a detectable signal.

In some embodiments, an unknown target nucleic acid is analyzed in combination with a known synthetic control target nucleic acid, to, for example, determine an amount of the unknown target nucleic acid.

The present invention also provides compositions and systems containing one or more components useful, necessary, or sufficient for conducting any of the methods described herein. For example, in some embodiments, a composition comprises: a) a target nucleic acid; b) amplification primers; c) a polymerase; d) a FEN-1 endonuclease; and e) an unlabeled synthetic probe comprising an analyte-specific portion and a non-target portion, wherein the non-target potion is substantially non-complementary to the target nucleic acid and wherein the target binding portion contains no more than 12 nucleotides that are complementary to the target nucleic acid. In some embodiments, the composition is a reaction mixture. In some embodiments, the composition is a kit (e.g., containing one or more containers, each housing one or more of the components). In some embodiments, a system of the invention comprises the composition and one or more additional components such as sample purification or processing reagents or equipment, detection equipment, control software, and data analysis systems.

In some embodiments, the composition comprises: a) a target nucleic acid; b) amplification primers; c) a polymerase; d) a FEN-1 endonuclease; and e) an unlabeled synthetic probe comprising an analyte-specific portion and a non-target portion, wherein the non-target potion is substantially non-complementary to the target nucleic acid. The present invention also provides methods of analyzing a target nucleic acid comprising: providing such a composition, forming a cleavage structure between the probe and the target nucleic acid during an amplification reaction, cleaving the probe with the FEN-1 endonuclease to generate a cleavage product containing the non-target portion of the probe, and detecting the cleavage product.

DESCRIPTION OF THE DRAWINGS

FIG. 2A provides a diagram showing use in an assay according to FIG. 1 of footprint probes having ASRs of 10 and 11 nucleotides (calculated Tms of 34.2 and 36.2° C., respectively, calculated using the nearest-neighbor model and published parameters for DNA duplex formation, Allawi and SantaLucia, Biochemistry, 36:10581 (1997), and SantaLucia, Proc Natl Acad Sci USA., 95(4):1460 (1998)) in assays according to FIG. 1. For the assays shown in FIGS. 2A and 2B, target nucleic acid was amplified by PCR in a separate reaction. The polymerase enzyme was heat killed and an aliquot of the PCR was used in INVADER assay reactions lacking FRET cassettes and using the diagrammed invasive cleavage structures. The reactions were run using Pfu FEN-1 endonuclease at the indicated temperatures (in a gradient thermal cycler). Appropriate FRET cassettes were then added to the reactions and the amounts of probe cleaved in the initial INVADER assay reactions were determined by measuring cleavage of the FRET cassettes. These data show that probes comprising ASRs of 10 or 11 nucleotides have similar broad curves of performance over a range of reaction temperatures, and similar performance independence from reaction temperature.

FIG. 3 shows a Table of footprint probes showing variations in calculated $T_m$ of analyte-specific regions. None of these probes contained duplex stabilizing moieties such as MGBs. The indicated Tms were calculated according to the methods described in the description of FIG. 2A. Each of the probes shown in FIG. 3 performed in invasive cleavage reactions at 50° C. (tests at 52° C. showed the same results), demonstrating that footprint probes comprising ASRs of about 12 or few nucleotides can be designed and used without the need to match the Tms to the reaction temperature(s).

FIG. 5 shows oligonucleotide sequences for amplifying and genotyping a SNP in a Factor V target sequence using PCR+invasive cleavage with footprint probes.

FIGS. 6A-C show the PCR+invasive cleavage results (performed as described in Example 3), with FIG. 6A showing a detection plot for the mutant Factor V target sequence; FIG. 6B showing a detection plot for the wild-type Factor V target sequence; and FIG. 6C showing a detection plot for heterogeneous Factor V target sequences. FIGS. 6D-F show the TAQMAN assay results, with FIG. 6D showing an amplification plot for the mutant Factor V target sequence; FIG. 6E showing an amplification plot for the wild-type Factor V target sequence; and FIG. 6F showing an amplification plot for heterogeneous Factor V target sequences.

FIGS. 8A-8D compare the results of detecting single base variations using the "INVADER Plus" assay combining PCR amplification with post-amplification detection using the INVADER assay (panel 8A) with detection of wild type or Oka mutation of VZV using real time PCR+invasive cleavage using footprint probes (panels B and C, with D providing a no target control).

FIGS. 9A-C show results achieved (using conditions as described in Example 3) in the detection of Human miR-21 microRNA with a footprint probe comprising 12 complementary nucleotides in the ASR compared with a footprint probe comprising 12 nucleotides, in which 1 nucleotide is mismatched to the target, and a footprint probe having only 11 nucleotides in the ASR. A probe having 11 complementary nucleotides plus 2 mismatched nucleotides (for a total of 13 nucleotides in the ASR) was also tested. Panel A shows a schematic diagram of the test molecules, and panel B shows data from samples having 600 or 6000 copies of miR-21 RNA.

FIGS. 11A-E show oligonucleotide sequences for amplifying and detecting several human miRNA and snRNA targets. FIG. 11A shows oligonucleotide sequences for amplifying and detecting the human miR-21 target; FIG. 11B shows oligonucleotide sequences for amplifying and detecting the human miR-155 target; FIG. 11C shows oligonucleotide sequences for amplifying and detecting the human miR-126 target; FIG. 11D shows oligonucleotide sequences for amplifying and detecting the human U6 snRNA target; and FIG. 11E shows oligonucleotide sequences for amplifying and detecting the human U24 snRNA target.

FIGS. 12A-12E show the results of the combined PCR-invasive cleavage assay using the assay designs shown in FIG. 11, which includes the use of footprint probes. The data for each target was plotted as fluorescence versus cycle number. For each target, a threshold was assigned that gave the most linear fit of copy number versus target level (see bottom panel in each figure). The results for each target are shown in the following figures: miR-155 (FIG. 12A); miR-21 (FIG. 112B); miR-126 (FIG. 12C); U6 (FIG. 12D); and U24 (FIG. 12E).

FIGS. 13A-13E show oligonucleotide sequences for amplifying and detecting several DNA and RNA targets. FIG. 13A shows the oligonucleotide sequences for amplifying and detecting the U6 DNA target; FIG. 13B shows the oligonucleotide sequences for amplifying and detecting the factor V DNA target; FIG. 13C shows the oligonucleotide sequences for amplifying and detecting the factor II DNA target; FIG. 13D shows the oligonucleotide sequences for amplifying and detecting the GA-21-R DNA target; and FIG. 13E shows the oligonucleotide sequences for amplifying and detecting the human U6 RNA target.

FIGS. 14A-D show the results of detecting Factor II with the combination of PCR and an invasive cleavage assay and footprint probes from Example 2. FIGS. 14A-B show the results of Example 2 with both the invasive oligonucleotide and the Afu FEN-1 enzyme present, while FIGS. 14C-D shows the results with the invasive oligonucleotide and Afu FEN-1 enzyme not present.

FIGS. 15A-F show the results of detecting Factor V with the combination of PCR and an invasive cleavage assay using a footprint probe from Example 2. FIGS. 15A-B show the results of Example 2 with all the reactions components present. FIGS. 15C-D show the results with the invasive oligonucleotide and Afu FEN-1 enzyme not present. FIGS. 15E-F show the same results as FIGS. 15C-D, except the y-axis maximum is 10,000 rather than 60,000.

FIGS. 16A-D show the results of detecting GA-21-R with the combination of PCR and an invasive cleavage assay using a footprint probe from Example 2. FIGS. 16A-B show the results of this Example with both the invasive oligonucleotide and the Afu FEN-1 enzyme present, while FIGS. 16C-D show the results with the invasive oligonucleotide and Afu FEN-1 enzyme not present.

FIGS. 17A-D show the results of detecting U6 RNA with the combination of PCR and an invasive cleavage assay using a footprint probes from Example 2. FIGS. 17A-B show the results of Example 2 with both the invasive oligonucleotide and the Afu FEN-1 enzyme present, while FIGS. 17-C-D show the results with the invasive oligonucleotide and Afu FEN-1 enzyme not present.

DEFINITIONS

Figure 1:
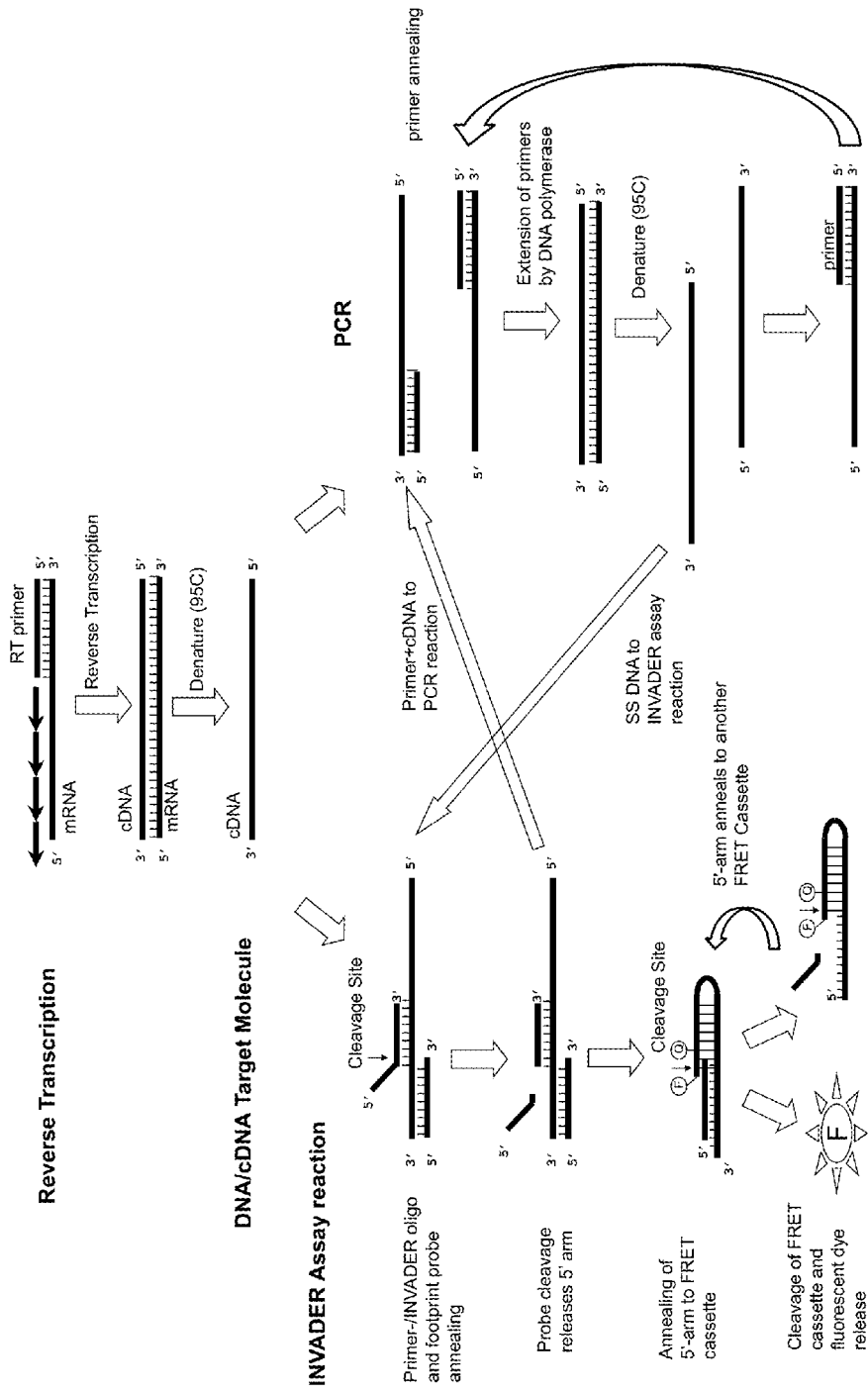
FIG. 1 provides a schematic diagram of an embodiment of the present invention comprising a combined PCR and invasive cleavage reaction using footprint probes for invasive cleavage.
Figure 2B:
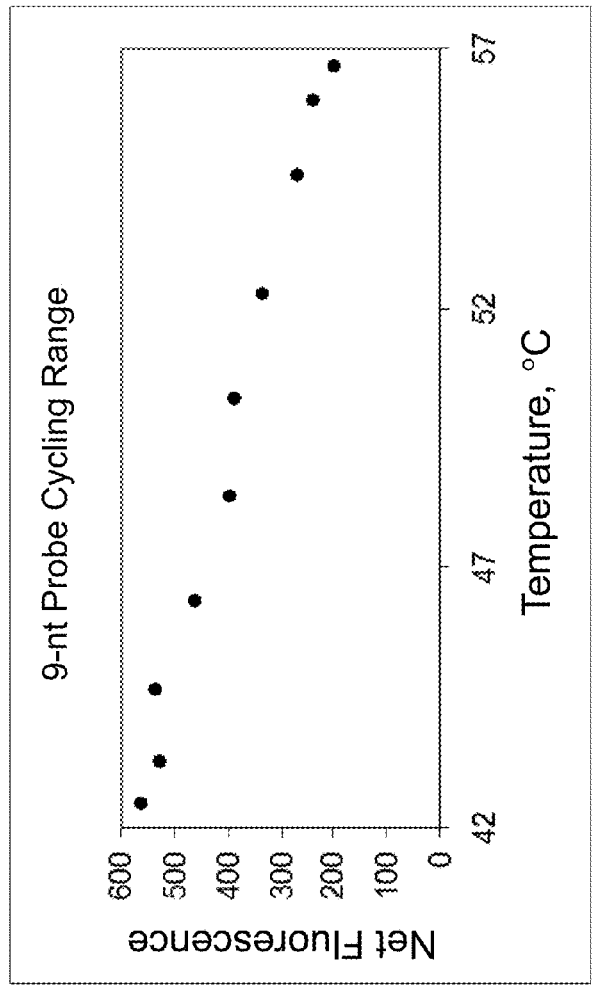
FIG. 2B shows the performance of a footprint probe having an ASR of 9 nucleotides ($T_m$ of 45.6° C. calculated according to the methods described in the description of FIG. 2A) in assays according to FIG. 1. These data show that a probe comprising an ASR of 9 nucleotides also performs over a range of reaction temperatures, and that performance decreases modestly as the reaction temperature is increased. While not limiting the present invention to any particular mechanism of action, the observations that this probe has a higher $T_m$ than the 10 and 11 ASR probes, yet shows a decrease in performance as temperature is increased suggests that the decrease in performance is linked to the enzyme's decreased ability to stabilize the probe as the ASR of the probe

To facilitate an understanding of the present invention, a number of terms and phrases are defined below:

The term "enzyme footprint probe" or "footprint probe" as used herein in reference to nucleic acid probes configured to form a structure, e.g., a duplex, with, for example, a target nucleic acid, refers to probes selected to form a minimal structure necessary for a selected level of enzyme response to the structure. In some embodiments, a footprint probe is selected to provide the minimal structure necessary for optimal performance (e.g., recognition, binding, cleavage, etc.), while in some embodiments, a footprint probe is selected to provide less than the minimal structure necessary for optimal performance, such that the performance is, for example, restricted, reduced, or otherwise made more stringent in its application.

By way of example and not limiting the invention to any particular nucleic acid modifying enzyme, a particular 5' nuclease, e.g., a FEN-1 endonuclease, may have been determined to favor a duplex of at least about 12 base pairs between a probe and target strand for optimal recognition and cleavage of the probe annealed to the target nucleic acid. Generally, a longer probe-target duplex, while not necessarily reducing the activities of the enzyme, does not provide any further increase in activity (e.g., in binding or cleavage activity of the FEN-1 endonuclease). A probe that provides additional duplex length without an increase in the activity of interest of the enzyme (e.g., probe cleavage by the FEN-1 enzyme) would generally fall outside the definition of a footprint probe for this enzyme. For example, for a FEN-1 endonuclease having maximum activity when the probe-target duplex is at least 12 base pairs long, a probe providing more base pairs, e.g., 15 or 16, or more base pairs of probe/target duplex, would not generally be considered a footprint probe for this particular enzyme. If a different FEN-1 endonuclease were to have maximum activity only when the probe-target duplex is at least 15 base pairs long (e.g., a FEN from a different organism, or modified to have a larger footprint, or used in conditions in which the footprint is determined to be enlarged from a smaller footprint), a footprint probe for the second FEN-1 would be a probe having an ASR of 15 or fewer nucleotides.

The term "footprint duplex length" as used herein refers to the minimum length of duplex at which a duplex-recognizing, nucleic acid modifying enzyme, e.g., a FEN-1 endonuclease, demonstrates full activity in the conditions of a reaction. For example, for a FEN-1 endonuclease having maximum activity when the probe-target duplex is at least 12 base pairs long, as discussed above, the footprint duplex length of the FEN-1 enzyme is 12 base pairs. A footprint probe generally provides an ASR that has a length up to but not exceeding the footprint duplex length of the enzyme with which the probe is to be used.

As used herein, the term "dynamic range" refers to the quantitative range of usefulness in a detection assay (e.g., a nucleic acid detection assay). For example, the dynamic range of a viral detection assay is the range between the smallest number of viral particles (e.g., copy number) and the largest number of viral particles that the assay can distinguish between.

As used herein, the terms "subject" and "patient" refer to any organisms including plants, microorganisms and animals (e.g., mammals such as dogs, cats, livestock, and humans).

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically. In some embodiments, an oligonucleotide primer is used with a template nucleic acid, extension of the primer is template dependent, such that a complement of the template is formed.

The term "cleavage structure" as used herein, refers to a structure that is formed by the interaction of at least one probe oligonucleotide and a target nucleic acid, forming a structure comprising a duplex, the resulting structure being cleavable by a cleavage means, including but not limited to an enzyme. The cleavage structure is a substrate for specific cleavage by the cleavage agent, in contrast to a nucleic acid molecule that is a substrate for non-specific cleavage by agents such as phosphodiesterases, which cleave nucleic acid molecules without regard to secondary structure (i.e., no formation of a duplexed structure is required).

The term "invasive cleavage structure" as used herein refers to a cleavage structure comprising i) a target nucleic acid, ii) an upstream nucleic acid (e.g., an INVADER oligonucleotide), and iii) a downstream nucleic acid (e.g., a probe), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain).

The term "cleavage means" or "cleavage agent" as used herein refers to any means that is capable of cleaving a cleavage structure, including but not limited to enzymes. "Structure-specific nucleases" or "structure-specific enzymes" are enzymes that recognize specific secondary structures in a nucleic molecule and cleave these structures. The cleavage agent of the invention cleaves a nucleic acid molecule in response to the presence of a cleavage structure; it is not necessary that the cleavage agent cleave the cleavage structure at any particular location within the cleavage structure.

The cleavage agent may include nuclease activity provided from a variety of sources including the CLEAVASE enzymes from Third Wave Technologies, Inc. (Madison, Wis.), the FEN-1 endonucleases (including RAD2 and XPG proteins, and natural or modified FEN-1 enzymes or chimerical enzymes comprising at least a portion of one or more FEN-1 enzymes), and enzymes comprising a 5' nuclease activity, such as eubacterial PolA polymerases including but not limited to Taq DNA polymerase, Tth DNA polymerase and E. coli DNA polymerase I. The cleavage agent may also include modified DNA polymerases having 5' nuclease activity but lacking synthetic activity. Examples of cleavage agents suitable for use in the method and kits of the present invention are provided in U.S. Pat. Nos. 5,614,402; 5,795,763; 5,843,669; 7,122,364, 7,150,982, and PCT Appln. Nos WO 98/23774; WO 02/070755A2; and WO0190337A2, each of which is herein incorporated by reference it its entirety.

The term "thermostable" when used in reference to an enzyme, such as a 5' nuclease, indicates that the enzyme is functional or active (i.e., can perform catalysis) at an elevated temperature, i.e., at about 55° C. or higher. In some embodiments the enzyme is functional or active at an elevated temperature of 65° C. or higher (e.g., 75° C., 85° C., 95° C., etc.).

The term "cleavage products" as used herein, refers to products generated by the reaction of a cleavage agent with a cleavage structure (i.e., the treatment of a cleavage structure with a cleavage agent).

As used herein, the term "specifically hybridizes" means that under given hybridization conditions a probe or primer detectably hybridizes to substantially only the target sequence in a sample comprising the target sequence (i.e., there is little or no detectable hybridization to non-target sequences). In an amplification method that comprises cycles of denaturation and annealing of nucleic acid, e.g., targets and primers or probes, given hybridization conditions include the conditions for the annealing step in the amplification method, i.e., an annealing temperature selected on the basis of predicted $T_m$, and salt conditions suitable for the polymerase enzyme of choice.

The term "amplified" as used herein refers to an increase in the abundance of molecule, moiety or effect. A target nucleic acid may be amplified, e.g., by in vitro replication such as by PCR. A signal, e.g., a detectable event or product that indicates the presence of a target nucleic acid As used herein, the term "amplification method" as used in reference to nucleic acid amplification means a process of specifically amplifying the abundance of a nucleic acid of interest. Some amplification methods (e.g., polymerase chain reaction, or PCR) comprise iterative cycles of thermal denaturation, oligonucleotide primer annealing to template molecules, and nucleic acid polymerase extension of the annealed primers. Conditions and times necessary for each of these steps are well known in the art. Some amplification methods are conducted at a single temperature and are deemed "isothermal." Accumulation of the products of amplification may be exponential or linear. Some amplification methods ("target amplification" methods) amplify the abundance of a target sequence, e.g., by copying it many times (e.g., PCR, NASBA, TMA, strand displacement amplification, ligase chain reaction, LAMP, ICAN, RPA, SPIA, HAD, etc.), while some amplification methods amplify the abundance of a nucleic acid species that may or may not contain the target sequence, but the amplification of which indicates the presence of a particular target sequence in the reaction (e.g., rolling circle amplification, RAM amplification). The latter methods are sometimes referred to as "signal amplification" methods. Some signal amplification methods may increase the abundance of a species of nucleic acid by converting a starting nucleic acid, e.g., by cleaving the starting nucleic acid to form cleavage products, or by extending it by, e.g., polymerization or ligation. A target amplification method may be applied to a signal molecule (e.g., PCR may be used to produce more copies of the product of a ligation, cleavage, or non-target copying reaction), or vice versa.

As used herein, the terms "polymerase chain reaction" and "PCR" refer to an enzymatic reaction in which a segment of DNA is replicated from a target nucleic acid in vitro. The reaction generally involves extension of a primer on each strand of a target nucleic acid with a template dependent DNA polymerase to produce a complementary copy of a portion of that strand. The chain reaction comprises iterative cycles of denaturation of the DNA strands, e.g., by heating, followed by cooling to allow primer annealing and extension, resulting in an exponential accumulation of copies of the region of the target nucleic acid that is flanked by and that includes the primer binding sites. When an RNA target nucleic acid is amplified by PCR, it is generally first reverse transcribed to produce a DNA copy strand.

As used herein, the term "primer annealing" refers to conditions that permit oligonucleotide primers to hybridize to template nucleic acid strands. Conditions for primer annealing vary with the length and sequence of the primer and are generally based upon the $T_m$ that is determined or calculated for the primer. For example, an annealing step in an amplification method that involves thermocycling involves reducing the temperature after a heat denaturation step to a temperature based on the $T_m$ of the primer sequence, for a time sufficient to permit such annealing.

As used herein, the term "amplifiable nucleic acid" is used in reference to nucleic acids that may be amplified by any amplification method. It is contemplated that "amplifiable nucleic acid" will usually comprise "sample template."

The term "real time" as used herein in reference to detection of nucleic acid amplification or signal amplification refers to the detection or measurement of the accumulation of products or signal in the reaction while the reaction is in progress, e.g., during incubation or thermal cycling. Such detection or measurement may occur continuously, or it may occur at a plurality of discrete points during the progress of the amplification reaction, or it may be a combination. For example, in a polymerase chain reaction, detection (e.g., of fluorescence) may occur continuously during all or part of thermal cycling, or it may occur transiently, at one or more points during one or more cycles. In some embodiments, real time detection of PCR is accomplished by determining a level of fluorescence at the same point (e.g., a time point in the cycle, or temperature step in the cycle) in each of a plurality of cycles, or in every cycle. Real time detection of amplification may also be referred to as detection "during" the amplification reaction.

As used herein, the terms "reverse transcription" and "reverse transcribe" refer to the use of a template-dependent polymerase to produce a DNA strand complementary to an RNA template.

As used herein, the term "abundance of nucleic acid" refers to the amount of a particular target nucleic acid sequence present in a sample or aliquot. The amount is generally referred to in terms of mass (e.g., μgs), mass per unit of volume (e.g., μgs per μl); copy number (e.g., 1000 copies, 1 attomole), or copy number per unit of volume (e.g., 1000 copies per ml, 1 attomole per μl). Abundance of a nucleic acid can also be expressed as an amount relative to the amount of a standard of known concentration or copy number. Measurement of abundance of a nucleic acid may be on any basis understood by those of skill in the art as being a suitable quantitative representation of nucleic acid abundance, including physical density or the sample, optical density, refractive property, staining properties, or on the basis of the intensity of a detectable label, e.g. a fluorescent label.

The term "amplicon" or "amplified product" refers to a segment of nucleic acid, generally DNA, generated by an amplification process such as the PCR process. The terms are also used in reference to RNA segments produced by amplification methods that employ RNA polymerases, such as NASBA, TMA, etc.

The term "amplification plot" as used in reference to a thermal cycling amplification reaction refers to the plot of signal that is indicative of amplification, e.g., fluorescence signal, versus cycle number. When used in reference to a non-thermal cycling amplification method, an amplification plot generally refers to a plot of the accumulation of signal as a function of time.

The term "baseline" as used in reference to an amplification plot refers to the detected signal coming from assembled amplification reactions at prior to incubation or, in the case of PCR, in the initial cycles, in which there is little change in signal.

The term "Ct" or "threshold cycle" as used herein in reference to real time detection during an amplification reaction that is thermal cycled refers to the fractional cycle number at which the detected signal (e.g., fluorescence) passes the fixed threshold.

The term "no template control" and "no target control" (or "NTC") as used herein in reference to a control reaction refers to a reaction or sample that does not contain template or target nucleic acid. It is used to verify amplification quality.

The term "passive reference" as used in reference to a detection reaction refers to a reference material, such as a dye, that provides an internal reference to which a reporter signal (e.g., another dye) can be normalized during data analysis. Normalization is generally necessary to correct for fluctuations caused by changes in concentration or volume.

"Rn" or "normalized reporter" refers to the fluorescence emission intensity of the reporter dye divided by the fluorescence emission intensity of the passive reference dye.

"Rn+" refers to the Rn value of a reaction containing all components, including the template or target.

Rn− refers to the Rn value of an un-reacted sample. The Rn-value can be obtained from the early cycles of a real time reaction, e.g., a real time PCR run (those cycles prior to a detectable increase in fluorescence), or from a reaction that does not contain any template.

"ΔRn" or "delta Rn" refers to the magnitude of the signal generated by the given set of amplification conditions, e.g., PCR conditions. The ΔRn value is determined by the following formula: (Rn+)−(Rn−) Standard A sample of known concentration used to construct a standard curve. By running standards of varying concentrations, one creates a standard curve from which one can extrapolate the quantity of an unknown sample.

The term "threshold" as used in reference to real time detection of an amplification reaction refers to the average standard deviation of Rn for the early PCR cycles, multiplied by an adjustable factor. The threshold should be set in the region associated with an exponential growth of PCR product.

The term "unknown" as used in reference to a quantitative assay refers to a sample containing an unknown quantity of template, generally a sample whose quantity one wants to determine, e.g., by performance of a quantitative assay such as a real time PCR and/or INVADER assay reaction.

As used herein, the term "sample template" refers to nucleic acid originating from a sample that is analyzed for the presence of "target." In contrast, "background template" is used in reference to nucleic acid other than sample template that may or may not be present in a sample. The presence of background template is most often inadvertent. It may be the result of carryover, or it may be due to the presence of nucleic acid contaminants sought to be purified away from the sample. For example, nucleic acids from organisms other than those to be detected may be present as background in a test sample.

The terms "analyte-specific region" or "ASR" and "analyte-specific portion" as used in reference to an oligonucleotide, such as a primer, a probe oligonucleotide, or an INVADER oligonucleotide, are used interchangeably and refer to a region/portion of an oligonucleotide selected to specifically hybridize to a particular nucleic acid sequence in a target nucleic acid or set of target nucleic acids. In some embodiments, an analyte-specific region of an oligonucleotide may be completely complementary to the segment of a target nucleic acid to which it hybridizes, while in other embodiments, an analyte-specific region may comprise one or more mismatches to the segment of a target nucleic acid to which it hybridizes. In yet other embodiments, an analyte-specific region may comprise one or more base analogs, e.g., compounds that have altered hydrogen bonding, or that do not hydrogen bond, to the bases in the target strand. In some embodiments, the entire sequence of an oligonucleotide is an analyte-specific region, while in other embodiments an oligonucleotide comprises an analyte-specific region and one or more regions not complementary the target sequence (e.g., non-complementary flap regions).

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "liberating" as used herein refers to the release of a nucleic acid fragment from a larger nucleic acid fragment, such as an oligonucleotide, by the action of, for example, a 5' nuclease such that the released fragment is no longer covalently attached to the remainder of the oligonucleotide.

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species.

The terms "archaea," "archaeal species," "archaean" and "archaebacteria" are used interchangeably refer to any organisms classified as a member of the Archaea domain or kingdom of life.

The term "virus" refers to obligate, ultramicroscopic, intracellular parasites incapable of autonomous replication (i.e., replication requires the use of the host cell's machinery).

The term "multi-drug resistant" or multiple-drug resistant" refers to a microorganism that is resistant to more than one of the antibiotics or antimicrobial agents used in the treatment of said microorganism.

The term "source of target nucleic acid" refers to any sample that contains nucleic acids (RNA or DNA). Particularly preferred sources of target nucleic acids are biological samples including, but not limited to blood, saliva, cerebral spinal fluid, pleural fluid, milk, lymph, sputum and semen.

A sample "suspected of containing" a first and a second target nucleic acid may contain either, both or neither target nucleic acid molecule.

The term "reactant" is used herein in its broadest sense. The reactant can comprise, for example, an enzymatic reactant, a chemical reactant or light (e.g., ultraviolet light, particularly short wavelength ultraviolet light is known to break oligonucleotide chains). Any agent capable of reacting with an oligonucleotide to either shorten (i.e., cleave) or elongate the oligonucleotide is encompassed within the term "reactant."

As used herein the term "portion" when in reference to a protein (as in "a portion of a given protein") refers to a fragment of that protein or a sequence of amino acids that is less than the complete chain of amino acids of the polypeptide. Similarly, when in reference to a nucleic acid (as in "a portion of a given nucleic acid or oligonucleotide"), the term refers to a fragment of a nucleic acid, or it refers to a sequence of nucleotides that is less than the complete chain of nucleotides of the nucleic acid or oligonucleotide. A portion may range in size from 1 amino acid or nucleotide residues, to the entire amino acid or nucleotide sequence.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

As used herein, the term "sample" is used in its broadest sense. For example, in some embodiments, it is meant to include a specimen or culture (e.g., microbiological culture), whereas in other embodiments, it is meant to include both biological and environmental samples (e.g., suspected of comprising a target sequence, gene or template). In some embodiments, a sample may include a specimen of synthetic origin. Samples may be unpurified or may be partially or completely purified or otherwise processed.

The present invention is not limited by the type of biological sample used or analyzed. The present invention is useful with a variety of biological samples including, but are not limited to, tissue (e.g., organ (e.g., heart, liver, brain, lung, stomach, intestine, spleen, kidney, pancreas, and reproductive (e.g., ovaries) organs), glandular, skin, and muscle tissue), cell (e.g., blood cell (e.g., lymphocyte or erythrocyte), muscle cell, tumor cell, and skin cell), gas, bodily fluid (e.g., blood or portion thereof, serum, plasma, urine, semen, saliva, etc), or solid (e.g., stool) samples obtained from a human (e.g., adult, infant, or embryo) or animal (e.g., cattle, poultry, mouse, rat, dog, pig, cat, horse, and the like). In some embodiments, biological samples may be solid food and/or feed products and/or ingredients such as dairy items, vegetables, meat and meat by-products, and waste. Biological samples may be obtained from all of the various families of domestic animals, as well as feral or wild animals, including, but not limited to, such animals as ungulates, bear, fish, lagomorphs, rodents, etc.

Biological samples also include biopsies and tissue sections (e.g., biopsy or section of tumor, growth, rash, infection, or paraffin-embedded sections), medical or hospital samples (e.g., including, but not limited to, blood samples, saliva, buccal swab, cerebrospinal fluid, pleural fluid, milk, colostrum, lymph, sputum, vomitus, bile, semen, oocytes, cervical cells, amniotic fluid, urine, stool, hair and sweat), laboratory samples (e.g., subcellular fractions), and forensic samples (e.g., blood or tissue (e.g., spatter or residue), hair and skin cells containing nucleic acids), and archeological samples (e.g., fossilized organisms, tissue, or cells).

Environmental samples include, but are not limited to, environmental material such as surface matter, soil, water (e.g., freshwater or seawater), algae, lichens, geological samples, air containing materials containing nucleic acids, crystals, and industrial samples, as well as samples obtained from food and dairy processing instruments, apparatus, equipment, utensils, disposable and non-disposable items.

Other types of biological samples include bacteria (e.g., Actinobacteria (e.g., *Actinomyces, Arthrobacter, Corynebacterium* (e.g., *C. diphtheriae*)), *Mycobacterium* (e.g., *M. tuberculosis* and *M. leprae*), *Propionibacterium* (e.g., *P. acnes*), *Streptomyces, hlamydiae* (e.g., *C. trachomatis* and *C. pneumoniae*), Cyanobacteria, *Deinococcus* (e.g., *Thermus* (e.g., *T. aquaticus*)), Firmicutes (e.g., *Bacilli* (e.g., *B. anthracis, B. cereus, B. thuringiensis*, and *B. subtilis*)), *Listeria* (e.g., *L. monocytogenes*), *Staphylococcus* (e.g., *S. aureus, S. epidermidis*, and *S. haemolyticus*), Fusobacteria, Proteobacteria (e.g., *Rickettsiales, Sphingomonadales, Bordtella* (e.g., *B. pertussis*), *Neisserisales* (e.g., *N. gonorrhoeae* and *N. meningitidis*), Enterobacteriales (e.g., *Escherichia* (e.g., *E. coli*), *Klebsiella, Plesiomonas, Proteus, Salmonella, Shigella*, and *Yersinia*), Legionellales, Pasteurellales (e.g., *Haemophilus influenzae*), *Pseudomonas, Vibrio* (e.g., *V. cholerae* and *V. vulnificus*), Campylobacterales (e.g., *Campylobacteria* (e.g., *C. jejuni*), and *Helicobacter* (e.g., *H. pylori*)), and Spirochaetes (e.g., *Leptospira, B. bergdorferi*, and *T. pallidum*)); Archaea (e.g., *Halobacteria* and *Methanobacteria*); Eucarya (e.g., Animalia (e.g., Annelidia, Arthropoda (e.g., Chelicerata, Myriapoda, Insecta, and Crustacea), Mollusca, Nematoda, (e.g., *C. elegans*, and *T. spiralis*) and Chordata (e.g., Actinopterygii, Amphibia, Ayes, Chondrichthyes, Reptilia, and Mammalia (e.g., Primates, Rodentia, Lagomorpha, and Carnivora)))); Fungi (e.g., *Dermatophytes, Fusarium, Penicillum*, and *Saccharomyces*); Plantae (e.g., Magnoliophyta (e.g., Magnoliopsida and Liliopsida)), and Protista (e.g., Apicomplexa (e.g., *Cryptosporidium, Plasmodium* (e.g., *P. falciparum*, and *Toxoplasma*), and Metamonada (e.g., *G. lambia*))); and Viruses (e.g., dsDNA viruses (e.g., Bacteriophage, Adenoviridae, Herpesviridae, Papillomaviridae, Polyomaviridae, and Poxyiridae), ssDNA virues (e.g., Parvoviridae), dsRNA viruses (including Reoviridae), (+)ssRNA viruses (e.g., Coronaviridae, Astroviridae, Bromoviridae, Comoviridae, Flaviviridae, Picornaviridae, and Togaviridae), (−) ssRNA viruses (e.g., Bornaviridae, Filoviridae, Paramyxoviridae, Rhabdoviridae, Bunyaviridae, and Orthomyxoviridiae), ssRNA-reverse transcribing viruses (e.g., Retroviridae), and dsDNA-reverse transcribing viruses (e.g., Hepadnaviridae and Caulomoviridae)).

Sample may be prepared by any desired or suitable method. In some embodiments, nucleic acids are analyzed directly from bodily fluids or other samples using the methods described in U.S. Pat. Pub. Serial No. 20050186588, herein incorporated by reference in its entirety.

The above described examples are not, however, to be construed as limiting the sample (e.g., suspected of comprising a target sequence, gene or template (e.g., the presence or absence of which can be determined using the compositions and methods of the present invention)) types applicable to the present invention.

The term "nucleotide analog", "non-natural", or "non-naturally occurring" as used herein refers to nucleotides other than the natural nucleotides and bases. Such analogs and non-natural bases and nucleotides include modified natural nucleotides and non-naturally occurring nucleotides, including but not limited to analogs that have altered stacking interactions such as 7-deaza purines (i.e., 7-deaza-dATP and 7-deaza-dGTP); base analogs with alternative hydrogen bonding configurations (e.g., such as iso-C and iso-G and other non-standard base pairs described in U.S. Pat. No. 6,001,983 to S. Benner, and the selectively binding base analogs described in U.S. Pat. No. 5,912,340 to Igor V. Kutyavin, et al.); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include modified forms of deoxyribonucleotides as well as ribonucleotides. "Non-natural" and "non-naturally occurring" bases and nucleotides are specifically not limited to such bases as are never found in nature. Natural processes such as nucleic acid damage can give rise to "natural" occurrence of bases that are nonetheless not generally considered to be part of the set of "natural" nucleotides as defined herein. For example, iso-G can be found in oxidatively damaged DNA. Such non-natural bases and their behaviors in replication and other nucleic acid syntheses have been extensively studied in contexts such as DNA damage studies, although the compounds are sometimes described using different nomenclature. For example, the ribonucleoside comprising the isoguanosine base has been referred to in the literature variously as: iG; isoG; iso-G; isoguanosine; 2-hydroxyadenine; 2-oxoadenine; 2-hydroxy A; and 2-OH-A. The deoxyribonucleoside comprising the isoguanosine base has been referred to variously as: iG; isoG; iso dG; deoxyiso-G; deoxyisoguanosine; 2-hydroxydeoxyadenosine; 2-hydroxy dA; and 2-OH-Ade.

Still other nucleotide analogs include modified forms of deoxyribonucleotides as well as ribonucleotides. Various oligonucleotides of the present invention (e.g., a primary probe or INVADER oligo) may contain nucleotide analogs.

The terms "nucleic acid sequence" and "nucleic acid molecule" as used herein refer to an oligonucleotide, nucleotide or polynucleotide, and fragments or portions thereof. The terms encompasses sequences that include analogs of DNA and RNA nucleotides, including those listed above, and also including, but not limited to, 4-acetylcytosine, 8-hydroxy-N-6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, 2,6-diaminopurine, and pyrazolo[3,4-d]pyrimidines such as guanine analogue 6 amino 1H-pyrazolo[3,4d]pyrimidin 4(5H) one (ppG or PPG, also Super G) and the adenine analogue 4 amino 1H-pyrazolo[3,4d]pyrimidine (ppA or PPA). The xanthine analogue 1H-pyrazolo[5,4d]pyrimidin 4(5H)-6(7H)-dione (ppX) can also be used. These base analogues, when present in an oligonucleotide, strengthen hybridization and improve mismatch discrimination. All tautomeric forms of naturally-occurring bases, modified bases and base analogues may be included in the oligonucleotide conjugates of the invention. Other modified bases useful in the present invention include 6-amino-3-prop-1-ynyl-5-hydropyrazolo[3,4-d]pyrimidine-4-one, PPPG; 6-amino-3-(3-hydroxyprop-1-yny)l-5-hydropyrazolo[3,4-d]pyrimidine-4-one, HOPPPG; 6-amino-3-(3-aminoprop-1-ynyl)-5-hydropyrazolo[3,4-d]pyrimidine-4-one, NH2PPPG; 4-amino-3-(prop-1-ynyl)pyrazolo[3,4-d]pyrimidine, PPPA; 4-amino-3-(3-hydroxyprop-1-ynyl)pyrazolo[3,4-d]pyrimidine, HOPPPA; 4-amino-3-(3-aminoprop-1-ynyl)pyrazolo[3,4-d]pyrimidine, $NH_2$ PPPA; 3-prop-1-ynylpyrazolo[3,4-d]pyrimidine-4,6-diamino, $(NH_2)_2$ PPPA; 2-(4,6-diaminopyrazolo[3,4-d]pyrimidin-3-yl)ethyn-1-ol, $(NH_2)_2$ PPPAOH; 3-(2-aminoethynyl)pyrazolo[3,4-d]pyrimidine-4,6-diamine, $(NH_2)_2$ PPPANH$_2$; 5-prop-1-ynyl-1,3-dihydropyrimidine-2,4-dione, PU; 5-(3-hydroxyprop-1-ynyl)-1,3-dihydropyrimidine-2,4-dione, HOPU; 6-amino-5-prop-1-ynyl-3-dihydropyrimidine-2-one, PC; 6-amino-5-(3-hydroxyprop-1-yny)-1,3-dihydropyrimidine-2-one, HOPC; and 6-amino-5-(3-aminoprop-1-yny)-1,3-dihydropyrimidine-2-one, $NH_2$PC; 5-[4-amino-3-(3-methoxyprop-1-ynyl)pyrazol[3,4-d]pyrimidinyl]-2-(hydroxym-ethyl)oxolan-3-ol, $CH_3$ OPPPA; 6-amino-1-[4-hydroxy-5-(hydroxymethyl)oxolan-2-yl]-3-(3-methoxyprop-1-yny-1)-5-hydropyrazolo[3,4-d]pyrimidin-4-one, $CH_3$ OPPPG; 4,(4,6-Diamino-1H-pyrazolo[3,4-d]pyrimidin-3-yl)-but-3-yn-1-ol, Super A; 6-Amino-3-(4-hydroxy-but-1-ynyl)-1,5-dihydro-pyrazolo[3,4-d]pyrimidin-4-o-ne; 5-(4-hydroxy-but-1-ynyl)-1H-pyrimidine-2,4-dione, Super T; 3-iodo-1H-pyrazolo[3,4-d]pyrimidine-4,6-diamine (($NH_2$)$_2$PPAI); 3-bromo-1H-pyrazolo[3,4-d]pyrimidine-4,6-diamine (($NH_2$)$_2$ PPABr); 3-chloro-1H-pyrazolo[3,4-d]pyrimidine-4,6-diamine (($NH_2$)$_2$PPACl); 3-Iodo-1H-pyrazolo[3,4-d]pyrimidin-4-ylamine (PPAI); 3-Bromo-1H-pyrazolo[3,4-d]pyrimidin-4-ylamine (PPABr); and 3-chloro-1H-pyrazolo[3,4-d]pyrimidin-4-ylamine (PPACl).

In addition to the modified bases noted above, oligonucleotides of the invention can have a backbone of sugar or glycosidic moieties, preferably 2-deoxyribofuranosides wherein all internucleotide linkages are the naturally occurring phosphodiester linkages. In alternative embodiments however, the 2-deoxy-β-D-ribofuranose groups are replaced with other sugars, for example, β-D-ribofuranose. In addition, β-D-ribofuranose may be present wherein the 2-OH of the ribose moiety is alkylated with a $C_{1-6}$ alkyl group (2-(O—$C_{1-6}$ alkyl) ribose) or with a $C_{2-6}$ alkenyl group (2-(O—$C_{2-6}$ alkenyl) ribose), or is replaced by a fluoro group (2-fluororibose). Related oligomer-forming sugars useful in the present invention are those that are "locked", i.e., contain a methylene bridge between C-4' and an oxygen atom at C-2'. Other sugar moieties compatible with hybridization of the oligonucleotide can also be used, and are known to those of skill in the art, including, but not limited to, α-D-arabinofuranosides, α-2'-deoxyribofuranosides or 2',3'-dideoxy-3'-aminoribofuranosides. Oligonucleotides containing α-D-arabinofuranosides can be prepared as described in U.S. Pat. No. 5,177, 196. Oligonucleotides containing 2',3'-dideoxy-3'-aminoribofuranosides are described in Chen et al. Nucleic Acids Res. 23:2661-2668 (1995). Synthetic procedures for locked nucleic acids (Singh et al, Chem. Comm., 455-456 (1998); Wengel J., Acc. Chem. Res., 32:301-310 (1998)) and oligonucleotides containing 2'-halogen-2'-deoxyribofuranosides (Palissa et al., Z. Chem., 27:216 (1987)) have also been described. The phosphate backbone of the modified oligonucleotides described herein can also be modified so that the oligonucleotides contain phosphorothioate linkages and/or methylphosphonates and/or phosphoroamidates (Chen et al., Nucl. Acids Res., 23:2662-2668 (1995)). Combinations of oligonucleotide linkages are also within the scope of the present invention. Still other backbone modifications are known to those of skill in the art.

In some embodiments, the modified bases described herein are incorporated into PNA and DNA/PNA chimeras to balance $T_m$s and provide modified oligonucleotides having improved mismatch discrimination. Various modified forms of DNA and DNA analogues have been used in attempts to overcome some of the disadvantages of the use of DNA molecules as probes and primers. Among these are peptide nucleic acids (PNAs, also known as polyamide nucleic acids). Nielsen et al. Science 254:1497-1500 (1991). PNAs contain heterocyclic base units, as found in DNA and RNA, that are linked by a polyamide backbone, instead of the sugar-phosphate backbone characteristic of DNA and RNA. PNAs are capable of hybridization to complementary DNA and RNA target sequences and, in fact, hybridize more strongly than a corresponding nucleic acid probe. The synthesis of PNA oligomers and reactive monomers used in the synthesis of PNA oligomers have been described in U.S. Pat. Nos. 5,539,082; 5,714,331; 5,773,571; 5,736,336 and 5,766,855. Alternate approaches to PNA and DNA/PNA chimera synthesis and monomers for PNA synthesis have been summarized. Uhlmann et al. Angew. Chem. Int. Ed. 37:2796-2823 (1998). Accordingly, the use of any combination of normal bases, unsubstituted pyrazolo[3,4-d]pyrimidine bases (e.g., PPG and PPA), 3-substituted pyrazolo[3,4-d]pyrimidines, modified purine, modified pyrimidine, 5-substituted pyrimidines, universal bases, sugar modification, backbone modification or a minor groove binder to balance the $T_m$ of a DNA, PNA or DNA/PNA chimera is in the scope of this invention. The synthetic methods necessary for the synthesis of modified base monomeric units required for nucleic acid, PNA and PNA/DNA chimeras synthesis are available in the art, see methods in this application and Uhlmann et al. Angew. Chem. Int. Ed. 37:2796-2823 (1998).

A nucleic acid sequence or molecule may be DNA or RNA, of either genomic or synthetic origin, that may be single or double stranded, and represent the sense or antisense strand. Thus, nucleic acid sequence may be dsDNA, ssDNA, mixed ssDNA, mixed dsDNA, dsDNA made into ssDNA (e.g., through melting, denaturing, helicases, etc.), A-, B-, or Z-DNA, triple-stranded DNA, RNA, ssRNA, dsRNA, mixed ss and dsRNA, dsRNA made into ssRNA (e.g., via melting, denaturing, helicases, etc.), messenger RNA (mRNA), ribosomal RNA (rRNA), transfer RNA (tRNA), catalytic RNA, snRNA, microRNA, or protein nucleic acid (PNA).

The present invention is not limited by the type or source of nucleic acid (e.g., sequence or molecule (e.g. target sequence and/or oligonucleotide)) utilized. For example, the nucleic acid sequence may be amplified or created sequence (e.g., amplification or creation of nucleic acid sequence via synthesis (e.g., polymerization (e.g., primer extension (e.g., RNA-DNA hybrid primer technology)) and reverse transcription (e.g., of RNA into DNA)) and/or amplification (e.g., polymerase chain reaction (PCR), rolling circle amplification (RCA), nucleic acid sequence based amplification (NASBA), transcription mediated amplification (TMA), ligase chain reaction (LCR), cycling probe technology, Q-beta replicase, strand displacement amplification (SDA), branched-DNA signal amplification (bDNA), hybrid capture, and helicase dependent amplification).

The terms "nucleotide" and "base" are used interchangeably when used in reference to a nucleic acid sequence, unless indicated otherwise herein.

The term "oligonucleotide" as used herein is defined as a molecule comprising two or more nucleotides (e.g., deoxyribonucleotides or ribonucleotides), preferably at least 5 nucleotides, more preferably at least about 10-15 nucleotides and more preferably at least about 15 to 30 nucleotides, or longer (e.g., oligonucleotides are typically less than 200 residues long (e.g., between 15 and 100 nucleotides), however, as used herein, the term is also intended to encompass longer polynucleotide chains). The exact size will depend on many factors, which in turn depend on the ultimate function or use of the oligonucleotide. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes. Oligonucleotides may be generated in any manner, including chemical synthesis, DNA replication, reverse transcription, PCR, or a combination thereof. In some embodiments, oligonucleotides that form invasive cleavage structures are generated in a reaction (e.g., by extension of a primer in an enzymatic extension reaction).

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

As used herein, the terms "complementary" or "complementarity" are used in reference to polynucleotides (e.g., a sequence of two or more nucleotides (e.g., an oligonucleotide or a target nucleic acid)) related by the base-pairing rules. For example, the sequence "5'-A-G-T-3'," is complementary to the sequence "3'-T-C-A-5'." Complementarity may be "partial," in which only some of the nucleic acid bases are matched according to the base pairing rules. Or, there may be "complete" or "total" complementarity between the nucleic acid bases. The degree of complementarity between nucleic acid strands has significant effects on the efficiency and strength of hybridization between nucleic acid strands. This is of particular importance in amplification reactions, as well as detection methods that depend upon the association of two or more nucleic acid strands. Either term may also be used in reference to individual nucleotides, especially within the context of polynucleotides. For example, a particular nucleotide within an oligonucleotide may be noted for its complementarity, or lack thereof, to a nucleotide within another nucleic acid sequence (e.g., a target sequence), in contrast or comparison to the complementarity between the rest of the oligonucleotide and the nucleic acid sequence.

The complement of a nucleic acid sequence as used herein refers to an oligonucleotide which, when aligned with the nucleic acid sequence such that the 5' end of one sequence is paired with the 3' end of the other, is in "antiparallel association." Nucleotide analogs, as discussed above, may be included in the nucleic acids of the present invention and include. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

The term "homology" refers to a degree of complementarity. There may be partial homology or complete homology (i.e., identity). A partially homologous sequence is one that is less than 100% identical to another sequence. A partially complementary sequence that is "substantially homologous" is a nucleic acid molecule that at least partially inhibits a completely complementary nucleic acid molecule from hybridizing to a target nucleic acid. The inhibition of hybridization of the completely complementary sequence to the target sequence may be examined using a hybridization assay (e.g., Southern or Northern blot, solution hybridization and the like) under conditions of low stringency. A substantially homologous sequence or probe will compete for and inhibit the binding (e.g., the hybridization) of a completely homologous nucleic acid molecule to a target under conditions of low stringency. This is not to say that conditions of low stringency are such that non-specific binding is permitted (e.g., the low stringency conditions may be such that the binding of two sequences to one another be a specific (e.g., selective) interaction). The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (e.g., is complementary to) the single-stranded nucleic acid sequence under conditions of low stringency as described above.

The terms "target nucleic acid" and "target sequence," refers to a nucleic acid of to be detected or analyzed. Thus, the "target" is sought to be distinguished from other nucleic acids or nucleic acid sequences. For example, when used in reference to an amplification reaction, these terms may refer to the nucleic acid or portion of nucleic acid that will be amplified by the reaction, while when used in reference to a polymorphism, they may refer to the portion of an containing a suspected polymorphism. When used in reference to an invasive cleavage reaction, these terms refer to a nucleic acid molecule containing a sequence that has at least partial complementarity with at least a first nucleic acid molecule (e.g. probe oligonucleotide) and may also have at least partial complementarity with a second nucleic acid molecule (e.g. INVADER oligonucleotide). Generally, the target nucleic acid (e.g., present within, isolated from, enriched from, or amplified from or within a sample (e.g., a biological or environmental sample)) is located within a target region and is identifiable via the successful formation of an invasive cleavage structure in combination with a first and second nucleic acid molecule (e.g., probe oligonucleotide and INVADER oligonucleotide) that is cleavable by a cleavage agent. Target nucleic acids from an organism are not limited to genomic DNA and RNA. Target nucleic acids from an organism may comprise any nucleic acid species, including but not limited to genomic DNAs and RNAs, messenger RNAs, structural RNAs, ribosomal and tRNAs, and small RNAs such as snRNAs, siRNAs and microRNAs (miRNAs). See, e.g., co-pending U.S. patent application Ser. No. 10/740,256, filed Dec. 18, 2003, which is incorporated herein by reference in its entirety. A "segment" is defined as a region of nucleic acid within the target sequence.

As used herein, the term "probe oligonucleotide," refers to an oligonucleotide that interacts with a target nucleic acid to form a detectable complex. In 5' nuclease cleavage assays such as the TAQMAN assay and the INVADER assay, the probe oligonucleotide hybridizes to the target nucleic acid and cleavage occurs within the probe oligonucleotide. In some embodiments, the complex between a probe and target is detected while it exists, while in some embodiments, the formation of the complex may be detected when it no longer exits, e.g., by detection of an event (e.g., a cleavage event) that occurred as a result of formation of the probe/target complex.

The term "INVADER oligonucleotide" refers to an oligonucleotide that hybridizes to a target nucleic acid at a location near the region of hybridization between a probe and the target nucleic acid, wherein the INVADER oligonucleotide comprises a portion (e.g., a chemical moiety, or nucleotide, whether complementary to that target or not) that overlaps with the region of hybridization between the probe and target. In some embodiments, the INVADER oligonucleotide contains sequences at its 3' end that are substantially the same as sequences located at the 5' end of a probe oligonucleotide.

The term "cassette," as used herein refers to an oligonucleotide or combination of oligonucleotides configured to generate a detectable signal in response to cleavage of a probe oligonucleotide. In preferred embodiments, the cassette hybridizes to a cleavage product from cleavage of the probe oligonucleotide to form a second invasive cleavage structure, such that the cassette can then be cleaved.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label. In particularly preferred embodiments, the cassette comprises labeled moieties that produce a fluorescence resonance energy transfer (FRET) effect.

An oligonucleotide is said to be present in "excess" relative to another oligonucleotide (or target nucleic acid sequence) if that oligonucleotide is present at a higher molar concentration than the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present in at least a 100-fold molar excess; typically at least 1 pmole of each probe oligonucleotide would be used when the target nucleic acid sequence was present at about 10 fmoles or less.

As used herein, the term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment polypeptide are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (e.g., hnRNA); introns may contain regulatory elements (e.g., enhancers). Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species (e.g., a viral or bacterial gene present within a human host (e.g., extrachromosomally or integrated into the host's DNA)). A heterologous gene also includes a gene native to an organism that has been altered in some way (e.g., mutated, added in multiple copies, linked to non-native regulatory sequences, etc). In some embodiments, a heterologous gene can be distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (e.g., these flanking sequences can be located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (e.g., altered characteristics) when compared to the wild-type gene or gene product. It is noted that naturally occurring mutants can be isolated (e.g., identified by the fact that they have altered characteristics (e.g., altered nucleic acid sequences) when compared to the wild-type gene or gene product).

The term "isolated" when used in relation to a nucleic acid (e.g., "an isolated oligonucleotide" or "isolated polynucleotide" or "an isolated nucleic acid sequence") refers to a nucleic acid sequence that is separated from at least one component or contaminant with which it is ordinarily associated in its natural source. Thus, an isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (e.g., the oligonucleotide or polynucleotide may be single-stranded), but may contain both the sense and anti-sense strands (e.g., the oligonucleotide or polynucleotide may be double-stranded).

As used herein, the terms "purified" or "to purify" when used in reference to a sample (e.g., a molecule (e.g., a nucleic acid or amino acid sequence)) refers to removal (e.g., isolation and/or separation) of the sample from its natural environment. The term "substantially purified" refers to a sample (e.g., molecule (e.g. a nucleic acid or amino acid sequence) that has been removed (e.g., isolated and/or purified) from its natural environment and is at least 60% free, preferably 75% free, or most preferably 90% or more free from other components with which it is naturally associated. An "isolated polynucleotide" or "isolated oligonucleotide" may therefore be substantially purified if it is rendered free (e.g., 60%, 75% or more preferably 90% or more) from other components with which it is naturally associated.

The present invention is not limited to any particular means of purification (e.g., to generate purified or substantially purified molecules (e.g., nucleic acid sequences)). Indeed, a variety of purification techniques may be utilized including, but not limited to, centrifugation (e.g., isopycnic, rate-zonal, gradient, and differential centrifugation), electrophoresis (e.g., gel and capillary electrophoresis), gel filtration, matrix capture, charge capture, mass capture, antibody capture, magnetic separation, flow cytometry, and sequence-specific hybridization array capture.

As used herein, the term "hybridization" is used in reference to the pairing of complementary nucleic acids. Hybridization and the strength of hybridization (e.g., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. A "calculated $T_m$" refers to a melting temperature determined by calculation from the physical sequence of complementary nucleic acids, along with factors of reaction conditions (e.g., salt concentration, concentrations of the complementary strands in a mixture). Several equations for calculating the $T_m$ of nucleic acids are well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See, e.g., Young and Anderson, (1985) in *Nucleic Acid Hybridisation: A Practical Approach* (Hames & Higgins, Eds.) pp 47-71, IRL Press, Oxford). Other computations for calculating $T_m$ are known in the art and take structural and environmental, as well as sequence characteristics into account (See, e.g., Allawi, H. T. and SantaLucia, J., Jr. Biochemistry 36, 10581-94 (1997)) and SantaLucia, Proc Natl Acad Sci USA., 95(4): 1460 (1998)).

As used herein, the term "INVADER assay reagents" refers to one or more reagents for detecting target sequences, said reagents comprising nucleic acid molecules capable of participating in formation of an invasive cleavage structure in the presence of the target sequence. In some embodiments, INVADER assay reagents comprise all of the nucleic acid molecules needed to form an invasive cleavage structure in preformed configuration, while in some embodiments, INVADER assay reagents provide or, are used in conjunction with one or more additional reagents (e.g., primers, polymerizing enzymes, ligases, nucleases) that allow the formation of nucleic acid molecules used in forming an invasive cleavage structure.

In some embodiments, the INVADER assay reagents further comprise an agent for detecting the presence of an invasive cleavage structure (e.g., a cleavage agent). In some embodiments, the nucleic acid molecules comprise first and second oligonucleotides, said first oligonucleotide comprising a 5' portion complementary to a first region of the target nucleic acid and said second oligonucleotide comprising a 3' portion and a 5' portion, said 5' portion complementary to a second region of the target nucleic acid downstream of and contiguous to the first portion. In some embodiments, the 3' portion of the second oligonucleotide comprises a 3' terminal nucleotide not complementary to the target nucleic acid. In preferred embodiments, the 3' portion of the second oligonucleotide consists of a single nucleotide not complementary to the target nucleic acid. INVADER assay reagents may be found, for example, in U.S. Pat. Nos. 5,846,717; 5,985,557; 5,994,069; 6,001,567; 6,913,881; and 6,090,543, WO 97/27214, WO 98/42873, U.S. Pat. Publ. Nos. 20050014163, 20050074788, 2005016596, 20050186588, 20040203035, 20040018489, and 20050164177; U.S. patent application Ser. No. 11/266,723; and Lyamichev et al., Nat. Biotech., 17:292 (1999), Hall et al., PNAS, USA, 97:8272 (2000), each of which is herein incorporated by reference in its entirety for all purposes.

In some embodiments, INVADER assay reagents are configured to detect a target nucleic acid sequence comprising first and second non-contiguous single-stranded regions separated by an intervening region comprising a double-stranded region. In certain embodiments, the INVADER assay reagents comprise a bridging oligonucleotide capable of binding to said first and second non-contiguous single-stranded regions of a target nucleic acid sequence. In particularly preferred embodiments, either or both of said first and/or said second oligonucleotides of said INVADER assay reagents are bridging oligonucleotides.

In some embodiments, the INVADER assay reagents further comprise a solid support. For example, in some embodiments, the one or more oligonucleotides of the assay reagents (e.g., first and/or second oligonucleotide, whether bridging or non-bridging) is attached to said solid support. The one or more oligonucleotides of the assay reagents may be linked to the solid support directly or indirectly (e.g., via a spacer molecule (e.g., an oligonucleotide)). Exemplary solid phase invasive cleavage reactions are described in U.S. Pat. Pub. Nos. 20050164177 and 20030143585, herein incorporated by reference in their entireties.

As used herein, a "solid support" is any material that maintains its shape under assay conditions, and that can be separated from a liquid phase. Supports that maintain their shape need not be rigid. Indeed, it is contemplated that flexible polymers such as carbohydrate chains, may be used as solid supports, so long as they can be separated from a liquid phase. The present invention is not limited by the type of solid support utilized. Indeed, a variety of solid supports are contemplated to be useful in the present invention including, but not limited to, a bead, planar surface, controlled pore glass (CPG), a wafer, glass, silicon, diamond, graphite, plastic, paramagnetic bead, magnetic bead, latex bead, superparamagnetic bead, plurality of beads, microfluidic chip, a silicon chip, a microscope slide, a microplate well, a silica gel, a polymeric membrane, a particle, a derivatized plastic film, a glass bead, cotton, a plastic bead, an alumina gel, a polysaccharide, polyvinylchloride, polypropylene, polyethylene, nylon, Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose or starch, polymeric microparticle, polymeric membrane, polymeric gel, glass slide, styrene, multi-well plate, column, microarray, latex, hydrogel, porous 3D hydrophilic polymer matrix (e.g., HYDROGEL, Packard Instrument Company, Meriden, Conn.), fiber optic bundles and beads (e.g., BEADARRAY (Illumina, San Diego, Calif.), described in U.S. Pat. App. 20050164177), small particles, membranes, frits, slides, micromachined chips, alkanethiol-gold layers, non-porous surfaces, addressable arrays, and polynucleotide-immobilizing media (e.g., described in U.S. Pat. App. 20050191660). In some embodiments, the solid support is coated with a binding layer or material (e.g., gold, diamond, or streptavidin).

In some embodiments, the INVADER assay reagents further comprise a buffer solution. In some preferred embodiments, the buffer solution comprises a source of divalent cations (e.g., $Mn^{2+}$ and/or $Mg^{2+}$ ions). Individual ingredients (e.g., oligonucleotides, enzymes, buffers, target nucleic acids) that collectively make up INVADER assay reagents are termed "INVADER assay reagent components."

In some embodiments, the INVADER assay reagents further comprise a third oligonucleotide complementary to a third portion of the target nucleic acid upstream of the first portion of the first target nucleic acid (e.g., a stacker oligonucleotides). In yet other embodiments, the INVADER assay reagents further comprise a target nucleic acid. In some embodiments, the INVADER assay reagents further comprise a second target nucleic acid. In yet other embodiments, the INVADER assay reagents further comprise a third oligonucleotide comprising a 5' portion complementary to a first region of the second target nucleic acid. In some specific embodiments, the 3' portion of the third oligonucleotide is covalently linked to the second target nucleic acid. In other specific embodiments, the second target nucleic acid further comprises a 5' portion, wherein the 5' portion of the second target nucleic acid is the third oligonucleotide. In still other embodiments, the INVADER assay reagents further comprise an ARRESTOR molecule (e.g., ARRESTOR oligonucleotide).

In some embodiments one or more of the INVADER assay reagents or INVADER assay reagent components may be provided in a predispensed format (e.g., premeasured for use in a step of the procedure without re-measurement or re-dispensing). In some embodiments, selected INVADER assay reagent components are mixed and predispensed together. In preferred embodiments, predispensed assay reagent components are predispensed and are provided in a reaction vessel (e.g., including, but not limited to, a reaction tube or a well (e.g., a microtiter plate)). In certain preferred embodiments, the INVADER assay reagents are provided in microfluidic devices such as those described in U.S. Pat. Nos. 6,627,159; 6,720,187; 6,734,401; and 6,814,935, as well as U.S. Pat. Pub. 2002/0064885, each of which is herein incorporated by reference in its entirety. In particularly preferred embodiments, predispensed INVADER assay reagent components are dried down (e.g., desiccated or lyophilized) in a reaction vessel.

In some embodiments, the INVADER assay reagents or INVADER assay reagent components are provided as a kit. As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte-specific reagents 'regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

In some embodiments, the present invention provides INVADER assay reagent kits comprising one or more of the components necessary for practicing the present invention. For example, the present invention provides kits for storing or delivering the enzymes and/or the reaction components necessary to practice an INVADER assay. The kit may include any and all components necessary or desired for assays including, but not limited to, the reagents themselves, buffers, control reagents (e.g., tissue samples, positive and negative control target oligonucleotides, etc.), solid supports, labels, written and/or pictorial instructions and product information, inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered. For example, a first container (e.g., box) may contain an enzyme (e.g., structure-specific cleavage enzyme in a suitable storage buffer and container), while a second box may contain oligonucleotides (e.g., INVADER oligonucleotides, probe oligonucleotides, control target oligonucleotides, etc.).

In some preferred embodiments, the INVADER assay reagents further comprise reagents for detecting a nucleic acid cleavage product. In some embodiments, one or more oligonucleotides in the INVADER assay reagents comprise a label. In some preferred embodiments, said first oligonucleotide comprises a label. In other preferred embodiments, said third oligonucleotide comprises a label. In particularly preferred embodiments, the reagents comprise a first and/or a third oligonucleotide labeled with moieties that produce a fluorescence resonance energy transfer (FRET) effect.

As used herein, the term "label" refers to any moiety (e.g., chemical species) that can be detected or can lead to a detectable response. In some preferred embodiments, detection of a label provides quantifiable information. Labels can be any known detectable moiety, such as, for example, a radioactive label (e.g., radionuclides), a ligand (e.g., biotin or avidin), a chromophore (e.g., a dye or particle that imparts a detectable color), a hapten (e.g., digoxygenin), a mass label, latex beads, metal particles, a paramagnetic label, a luminescent compound (e.g., bioluminescent, phosphorescent or chemiluminescent labels) or a fluorescent compound.

A label may be joined, directly or indirectly, to an oligonucleotide or other biological molecule. Direct labeling can occur through bonds or interactions that link the label to the oligonucleotide, including covalent bonds or non-covalent interactions such as hydrogen bonding, hydrophobic and ionic interactions, or through formation of chelates or coordination complexes. Indirect labeling can occur through use of a bridging moiety or "linker", such as an antibody or additional oligonucleotide(s), which is/are either directly or indirectly labeled.

Labels can be used alone or in combination with moieties that can suppress (e.g., quench), excite, or transfer (e.g., shift) emission spectra (e.g., fluorescence resonance energy transfer (FRET)) of a label (e.g., a luminescent label).

As used herein, the term "FRET" refers to fluorescence resonance energy transfer, a process in which moieties (e.g., fluorophores) transfer energy e.g., among themselves, or, from a fluorophore to a non-fluorophore (e.g., a quencher molecule). In some circumstances, FRET involves an excited donor fluorophore transferring energy to a lower-energy acceptor fluorophore via a short-range (e.g., about 10 nm or less) dipole-dipole interaction. In other circumstances, FRET involves a loss of fluorescence energy from a donor and an increase in fluorescence in an acceptor fluorophore. In still other forms of FRET, energy can be exchanged from an excited donor fluorophore to a non-fluorescing molecule (e.g., a quenching molecule). FRET is known to those of skill in the art and has been described (See, e.g., Stryer et al., 1978, Ann. Rev. Biochem., 47:819; Selvin, 1995, Methods Enzymol., 246:300; Orpana, 2004 Biomol Eng 21, 45-50; Olivier, 2005 Mutant Res 573, 103-110, each of which is incorporated herein by reference in its entirety).

As used herein, the term "unlabeled" as used in reference to a probe oligonucleotide refers to a probe oligonucleotide that does not comprise any non-nucleic acid moiety, e.g., a chromorphore or fluorophore, to facilitate detection. An unlabeled probe may comprise modifications, such as 3' blocking groups to prevent extension by a polymerase.

As used herein, the term "donor" refers to a moiety (e.g., a fluorophore) that absorbs at a first wavelength and emits at a second, longer wavelength. The term "acceptor" refers to a moiety such as a fluorophore, chromophore, or quencher and that is able to absorb some or most of the emitted energy from the donor when it is near the donor group (typically between 1-100 nm). An acceptor may have an absorption spectrum that overlaps the donor's emission spectrum. Generally, if the acceptor is a fluorophore, it then re-emits at a third, still longer wavelength; if it is a chromophore or quencher, it releases the energy absorbed from the donor without emitting a photon. In some preferred embodiments, alteration in energy levels of donor and/or acceptor moieties are detected (e.g., via measuring energy transfer (e.g., by detecting light emission) between or from donors and/or acceptor moieties). In some preferred embodiments, the emission spectrum of an acceptor moeity is distinct from the emission spectrum of a donor moiety such that emissions (e.g., of light and/or energy) from the moieties can be distinguished (e.g., spectrally resolved) from each other.

In some embodiments, a donor moiety is used in combination with multiple acceptor moieties. In a preferred embodiment, a donor moiety is used in combination with a non-fluorescing quencher moiety and with an acceptor moiety, such that when the donor moiety is close (e.g. between 1-100 nm, or more preferably, between 1-25 nm, or even more preferably around 10 nm or less) to the quencher, its excitation is transferred to the quencher moiety rather than the acceptor moiety, and when the quencher moiety is removed (e.g., by cleavage of a probe), donor moiety excitation is transferred to an acceptor moiety. In some preferred embodiments, emission from the acceptor moiety is detected (e.g., using wavelength shifting molecular beacons) (See, e.g., Tyagi, et al., Nature Biotechnology 18:1191 (2000); Mhlanga and Malmberg, 2001 Methods 25, 463-471; Olivier, 2005 Mutant Res 573, 103-110, and U.S. Pat. App. 20030228703, each of which is incorporated herein by reference in its entirety).

Suitable fluorophores include but are not limited to fluorescein, rhodamine, REDMOND RED dye, YAKIMA YELLOW dye, hexachloro-fluorescein, TAMRA dye, ROX dye, Cy3, Cy3.5, Cy5, Cy5.5, and Cy7, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid, 4,4-difluoro-5-styryl-4-bora-3a,4-adiaz-a-S-indacene-propionic acid, 6-carboxy-X-rhodamine, N,N,N',N'-tetramethyl-6-carboxyrhodamine, Texas Red, eosin, fluorescein, 4,4-difluoro-5,7-diphenyl-4-bora-3a,4a-diaza-s-indacene-3-propionic acid, 4,4-difluoro-5,p-ethoxyphenyl-4-bora-3a,4a-diaza-s-indacene 3-propionic acid and 4,4-difluoro-5-styryl-4-bora-3a,4a-diaza-5-indacene-propionic acid, 6-carboxyfluorescein (6-FAM), 2',4',1,4,-tetrachlorofluorescein (TET), 21,4',51,7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), 2'-chloro-7'-phenyl-1,4-dichloro-6-carboxyfluorescein (VIC), fluorescein isothiocyanate (FITC), 5,6-carboxymethyl fluorescein, Texas red, nitrobenz-2-oxa-1,3-diazol-4-yl (NBD), coumarin, dansyl chloride, amino-methyl coumarin (AMCA), Erythrosin, BODIPY dye, CASCADE BLUE dye, OREGON GREEN dye, pyrene, lissamine, xanthenes, acridines, oxazines, phycoerythrin, QUANTUM DYE, thiazole orange-ethidium heterodimer, and the like. Suitable quenchers include, but are not limited to, cyanine dyes, e.g., Cy3, Cy3.5, Cy5, Cy5.5, and Cy7, rhodamine dyes, e.g., tetramethyl-6-carboxyrhodamine (TAMRA) and tetrapropano-6-carboxyrhodamine (ROX), DABSYL dye, DABCYL dye, cyanine dyes, nitrothiazole blue (NTB), anthraquinone, malachite green, nitrothiazole, or nitroimidazole compounds, QSY7 (Molecular Probes, Eugene, Oreg.), ECLIPSE quencher (Nanogen, San Diego, Calif.), and the like. Analysis of factors such as absorbance and emission spectra of various molecules in selection of pairs or groups of moieties for use in FRET configurations is well known to those of skill in the art.

Detection of labels or a detectable response (e.g., provided by the labels) can be measured using a multitude of techniques, systems and methods known in the art. For example, a label may be detected because the label provides detectable fluorescence (e.g., simple fluorescence, FRET, time-resolved fluorescence, fluorescence quenching, fluorescence polarization, etc.), radioactivity, chemiluminescence, electrochemiluminescence, RAMAN, colorimetry, gravimetry, hyrbridization (e.g., to a sequence in a hybridization protection assay), X-ray diffraction or absorption, magnetism, enzymatic activity, characteristics of mass or behavior affected by mass (e.g., MALDI time-of-flight mass spectrometry), and the like.

As used herein the term "interactive label" refers to a label having two or more components that interact so as to produce a detectable effect. The interaction is not limited to any particular nature of interaction. The interaction of the label components may be via direct contact, e.g., a covalent or non-covalent contact between two moieties (e.g., a protein-protein contact, or collisional energy transfer between proximal moieties); it may comprise resonance energy transfer (e.g., between one or more dyes, or between a dye and a quencher moieties); it may comprise a diffusion effect, e.g., wherein the product from a reaction occurring at the site of one label diffuses to the site of another label to create a detectable effect. The components of an interactive label may be the same (e.g., two or more of the same molecule or atom) or they may be different.

A label may be a charged moiety (positive or negative charge) or alternatively, may be charge neutral. Labels can include or consist of nucleic acid or protein sequence, so long as the sequence comprising the label is detectable. In some embodiments, the label is not nucleic acid or protein.

In some embodiments, a label comprises a particle for detection. For example, in some embodiments, the particle is a phosphor particle. An example of a phosphor particle includes, but is not limited to, an up-converting phosphor particle (See, e.g., Ostermayer, Preparation and properties of infrared-to-visible conversion phosphors. Metall. Trans. 752, 747-755 (1971)). In some embodiments, rare earth-doped ceramic particles are used as phosphor particles. Phosphor particles may be detected by any suitable method, including but not limited to up-converting phosphor technology (UPT), in which up-converting phosphors transfer low energy infrared (IR) radiation to high-energy visible light. Although an understanding of the mechanism is not necessary to practice the present invention and the present invention is not limited to any particular mechanism of action, in some embodiments the UPT up-converts infrared light to visible light by multi-photon absorption and subsequent emission of dopant-dependant phosphorescence (See, e.g., U.S. Pat. No. 6,399,397; van De Rijke, et al., Nature Biotechnol. 19(3):273-6 (2001); Corstjens, et al., IEE Proc. Nanobiotechnol. 152(2):64 (2005), each incorporated by reference herein in its entirety.

As used herein, the term "distinct" in reference to signals (e.g., of one or more labels) refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the term "synthetic" as used in reference to a polynucleotide or oligonucleotide (e.g., a probe) refers to a nucleic acid created in a cell-free in vitro reaction, e.g., an enzymatic or chemical synthesis reaction. Examples of enzymatic formation of a synthetic nucleic acid include formation by restriction digestion, polymerization (templated or non-templated), ligation, etc. Examples of chemical synthesis of nucleic acid include but are not limited to, e.g., phosphodiester and phosphotriester chemistries, phosphoramidite and H-phosphonate, chemistries, etc. See e.g., *Methods in Molecular Biology, Vol* 20: *Protocols for Oligonucleotides and Analogs* pp. 165-189 (S. Agrawal, Ed., Humana Press, 1993); *Oligonucleotides and Analogues: A Practical Approach*, pp. 87-108 (F. Eckstein, Ed., 1991); and Uhlmann and Peyman, supra. Agrawal and Iyer, Curr. Op. in Biotech. 6: 12 (1995); and *Anti-sense Research and Applications* (Crooke and Lebleu; Eds., CRC Press, Boca Raton, 1993), Beaucage and Caruthers, Tetrahedron Lett. 22: 1859-1862 (1981), and Agrawal and Zamecnik, U.S. Pat. No. 5,149,798 (1992). In some embodiments, synthetic oligonucleotides are introduced into a reaction pre-formed, while in some embodiments, synthetic oligonucleotides are formed or modified within the reaction, e.g., by action of a polymerase, ligase, cleavage enzyme, or the like.

As used herein, the term "FEN-1" in reference to an enzyme refers to a non-polymerase flap endonuclease from a eukaryote or archaeal organism.

As used herein, the term FEN-1 activity refers to any enzymatic activity of a FEN-1 enzyme, including but not limited to flap endonuclease (FEN), nick exonuclease (EXO), and gap endonuclease (GEN) activities (see, e.g., Shen, et al., BioEssays Volume 27, Issue 7, Pages 717-729, incorporated herein by reference).

As used herein, the term "identifying the presence of a polymorphism" refers to any method of inferring the identity of a nucleotide at a position of a suspected point of genetic variation. In some embodiments, the presence of a particular polymorphism or mutation is directly detected, e.g., the presence of the polymorphism causes a detectable event to occur (e.g., probe hybridization, probe cleavage, nucleic acid target or signal amplification, etc.), while in other embodiments, the presence of a polymorphism or mutation may be inferred from the absence of a particular nucleotide or sequence of nucleotides (e.g., the absence of a wild-type nucleotide in a position in a nucleic acid sequence as an indicator of the presence of a mutant or polymorphic nucleotide at that position.)

As used herein, the term "determining an identity of an organism" encompasses any manner of assigning identification to an organism of interest, including but not limited to identification of a unique, individual organism, e.g., as a variant among a population of related organisms, and/or classification of an organism, e.g., by species, genus, family order, etc. Identity of an organism may be by phenotype or genotype.

DESCRIPTION OF THE INVENTION

The present invention relates to homogenous, real time assays for the detection of amplified nucleic acid, e.g., PCR amplified DNA. In some embodiments, the probes used comprise detectable moieties such as fluorophores, while in some embodiments, probes comprise an interactive detection system, such as fluorophore and quencher moieties. In yet other embodiments, the methods and systems of the present invention use unlabeled analyte-specific probes, coupled with a detection system configured to detect products of the cleavage of the analyte-specific probes.

The present invention provides real time detection methods using enzyme footprint probes having short analyte-specific regions. The footprint probes of the present invention are generally used in assay conditions that are at temperatures far in excess of the melting temperatures of the probes as calculated using standard methods, e.g., the nearest neighbor model and published parameters for DNA duplex formation, Allawi and SantaLucia, Biochemistry, 36:10581 (1997), and SantaLucia, Proc Natl Acad Sci USA., 95(4):1460 (1998).

Use of footprint probes in detection and characterization provides a more selective assay. While not limiting the invention to any particular mechanism of action, data suggests that the selectivity comes not only from the use of stringent hybridization conditions (e.g., elevated reaction temperatures), but also from the fact that any duplex formed must supply a successful footprint for enzyme recognition and cleavage.

One surprising result of the instant invention is that the functionality of the footprint probes has little or no dependence on the precise sequence of the probe, so long as the probe contains the correct length of ASR to form the probe-target duplex. An important aspect of this lack of dependence on sequence is that the $T_m$ of the analyte-specific region (determined, e.g., by the sequence content of the ASR) does not influence the performance of the probe in the detection reactions of the invention, even if the detection reaction is performed at a temperature substantially above the calculated $T_m$ of the probe-target duplex. Thus, in preferred embodiments, one can choose a probe based almost solely on the length (e.g. a length selected to be the known footprint of the enzyme to be used in the detection assay; e.g. 12 or fewer nucleotides for Afu FEN-1 endonuclease) and one need not even calculate $T_m$ of the analyte-specific region before proceeding with the detection assay.

This aspect of the instant invention is a dramatic departure from traditional probe based assays, in which elaborate software and probe modifications are used to select and construct probes that are operable at particular reaction temperatures. For example, in many prior art assays, e.g., the TAQMAN 5' nuclease assay or some embodiments of the INVADER and INVADER PLUS assays, a particular operating temperature for the assay is chosen as a first step in designing an assay for a new target. Reaction temperature is often selected as the first step so that numerous different experiments can be designed to be performed together, e.g., in the same thermal cycler or incubator. Once a temperature of operation is chosen, probes, primers and/or other nucleic acid components of the assay are designed for performance in the selected temperature conditions. For different target sequences, the probes and primers are adjusted, e.g., in length, G-C basepair content, and/or by the attachment of stabilizing moieties such as MGBs or peptide nucleic acids. The length of probes selected to operate at the same temperature may be very different, depending on the sequence of the target nucleic acid (e.g., whether it is G-C rich or A-T rich).

To successfully design large numbers of assays configured to operate at the same temperature (or in the same thermal cycling set of temperatures), complex software is often used in the design process. For example, Applied Biosystems provides the "PrimerExpress" software package for the design of primers and primer/probe combinations for use in TAQMAN and similar 5' nuclease PCR assays (e.g., the probe-based FULLVELOCITY assay by Stratagene, La Jolla, Calif.) to be run in preselected thermal cycling temperature profiles. Third Wave Technologies provides the INVADERCreator software for selection or INVADER oligonucleotide/probe combinations for detection assays to be run at a preselected temperature (e.g., 63° C.).

The compositions, methods, systems, and kits of the present invention obviate the need for such complex assay design steps and software.

Identification of Footprint Size

As discussed above, the present invention makes use of enzyme footprint probes. Identification of a recognition footprint for a duplex-recognizing nucleic acid modification enzyme is described here in the context of 5' nucleases, such as FEN-1 endonucleases. However, the invention is not limited to footprint probes designed for use with these enzymes. One of skill in the art would be well able to apply the same principles to the analysis of the activity requirements of other nucleic acid modifying enzymes.

A three-dimensional model of the structure-specific 5' flap endonuclease (FEN-1) from *Pyrococcus furiosus* in its complex with DNA has been proposed (see, e.g., U.S. patent application Ser. No. 10/783,557, and Allawi, et al., Journal of Molecular Biology v. 328(3):537-554 (2003)). The model is based on the known X-ray structure of the enzyme and a variety of biochemical and molecular dynamics data utilized in the form of distance restraints between the enzyme and the DNA. Contacts between the 5' flap endonuclease and the sugar-phosphate backbone of the overlap flap substrate were identified using enzyme activity assays on substrates with methylphosphonate or 2'-O-methyl substitutions. The enzyme footprint extends 2-4 base pairs upstream and 8-9 base pairs downstream of the cleavage site, thus covering 10-13 base pairs of duplex DNA. The footprint data are consistent with a model in which the substrate is bound in the DNA-binding groove such that the downstream duplex interacts with the helix-hairpin-helix motif of the enzyme.

It had been found, though, that, when used in conjunction with a probe or hairpin providing an upstream duplex, probes that provide a downstream duplex in the range of 6 to 12 nucleotides (i.e., probes that have 6-12 nucleotides of target-specific sequence) demonstrate increases in the rates of enzyme recognition and/or cleavage as the length of analyte-specific sequence approaches about 12 nucleotides when tested with the FEN-1 and polymerase-derived 5' nucleases, while no improvement in cleavage is seen for duplexes beyond that length (see, e.g., Kaiser, et al., J Biol Chem, Vol. 274, Issue 30, 21387-21394, Jul. 23, 1999. Thus, in preferred embodiments of the present invention, a footprint probe for use with the FEN-1 and polymerase-derived 5' nucleases provides an analyte-specific region of up to about 12 nucleotides in length. As noted above, in certain embodiments, one or more of the up to 12 nucleotides may be non-complementary to the target strand. In preferred embodiments, the footprint probes are used in conjunction with an oligonucleotide (e.g., a primer or INVADER oligonucleotide) that provides an upstream duplex.

Use of Footprint Probes in Amplification Assays

It is shown here that short footprint probes can be used in amplification assays, even in the presence of primers having higher melting temperatures, and even in reactions in which the "annealing temperature" used in thermal cycling is well above the calculated $T_m$ of the ASR of the footprint probe (calculated, e.g., using standard methods in the art, such as the nearest neighbor model and published parameters for DNA duplex formation, Allawi and SantaLucia, Biochemistry, 36:10581 (1997), and SantaLucia, Proc Natl Acad Sci USA., 95(4):1460 (1998). While not limiting the present invention to any particular mechanism of action, it appears that the FEN-1 enzyme may be a factor in facilitating the annealing and cleavage of short probes at temperatures well above their calculated $T_m$s. In fact, experimental data provided herewith shows that the temperatures at which the methods of the present invention can be practice have little or no dependence on the calculated $T_m$s of the ASRs of the probes used.

In some embodiments a probe that is to be cleaved in the course of the detection reaction and having a short analyte-specific region of, e.g., 6-12 nts, is used in conjunction with an oligonucleotide that hybridizes immediately downstream of the probe (downstream along the target strand and upstream of the 5' end of the ASR of the probe). To form the cleavage structure, an upstream nucleic acid (e.g., an INVADER oligonucleotide) is provided to promote cleavage of the short probe.

Although the methods, compositions, and systems of the present invention are described in this Description of the Invention, and in the Summary of the Invention (which is incorporated here by reference), in connection with certain specific embodiments, e.g., in the context of the polymerase chain reaction method of target amplification, it is to be appreciated that the invention is not limited to these embodiments. The embodiments discussed below are provided by way of example, and not to limit the invention.

Several embodiments and aspects of the present invention are discussed below.

Assays Having Improved Specificity

An aspect of the present invention is to provide systems and methods for detecting target amplification assays, such as PCR assays, in real time. In some embodiments, the present invention provides systems, methods and kits for performing target amplification assays in combination with detection assays (e.g., cleavage assays), where the detection assay employs probes with relatively short (e.g., 6-12 bases) analyte-specific regions. In preferred embodiments, these probes are configured to provide a probe/analyte duplex at or near the minimum length of duplex that is efficiently recognizable by a detection agent, e.g., a cleavage agent such as a FEN-1 nuclease, such that probes annealed to target with a mismatch in sequence to the analyte-specific portion of the probe are not cleaved with full efficiency or at all. In such embodiments, detectable cleavage from probes hybridized to mismatched target nucleic acids is reduced compared to detectable cleavage from probes hybridized to target nucleic acid that is perfectly complementary to the analyte-specific portion of the probes, and the assay thereby has greater specificity and/or lower background.

The invention is not limited to any particular mechanism of improved specificity and/or reduced background through the use of the footprint probes of the invention. One aspect of improved specificity is more selective hybridization afforded by short probes used in stringent hybridization conditions (e.g., at temperatures greater than the calculated $T_m$ of the analyte specific portion of the probe), such that only perfectly matched probes tend to anneal to a target strand, while in some embodiments, improved results may be due to discrimination by a cleavage enzyme between perfectly matched and imperfectly matched probe/target duplexes. Another aspect of improved specificity is through the use of probes configured to provide a duplex with the intended target that is at or near the minimum duplex length for efficient cleavage of the probe by a 5' nuclease, e.g., a FEN-1 enzyme. In such embodiments, if the analyte-specific portion of the probe is mismatched to the target in one or more nucleotide positions, the 5' nuclease cleavage of the duplex will be substantially reduced or absent. In particularly preferred embodiments, the FEN-1 is a thermostable FEN-1 from an archaeal species.

The effect of probe/target duplex length (also referred to as "downstream duplex length," in contrast to an "upstream duplex" such as is provided by, e.g., an INVADER oligonucleotide or a primer oligonucleotide) on cleavage efficiency of cleavage structures (e.g., invasive cleavage structures) has been studied for a variety of 5' nuclease enzymes. See, e.g., Kaiser et al., J. Biol. Chem. July 23; 274(30):21387-94 (1999), which is incorporated herein by reference. Kaiser examined the effects of probe/target duplex using substrates with downstream duplex lengths of between 6 and 16 base pairs for an overlapping flap substrate in which the upstream duplex (e.g., an INVADER oligonucleotide/target duplex) was 6 base pairs in length. Experiments examined four archaeal FEN1 enzymes, from *A. fulgidus* (AfuFEN), *P. furiosus* (PfuFEN), *M. jannaschii* (MjaFEN), and *M. thermoautotrophicum* (MthFEN), two eubacterial polymerase I enzymes from *T. aquaticus* (TaqPol) and *T. thermophilus* (TthPol) and the 5' nuclease domain of TaqPol (referred to as TaqExo). All enzymes, except TaqPol, cleaved the overlapping flap substrates at rates independent of downstream duplex length in the range from 10 to 16 base pairs; TaqPol cleaved the 10 base pair substrate approximately five times slower than the 12 base pair substrate. For most enzymes, cleavage activities decreased for the 8 base pair downstream duplex substrate and significantly dropped when the duplex length was reduced to 6 bp, although the FEN-1 enzymes of MjaFEN and MthFEN were able to cleave the substrate with the 6-base pair downstream duplex. Thus, use of probes having short analyte-specific regions provides an additional level of discrimination beyond the mechanics of hybridization in that, even if a short probe anneals to a mismatched target nucleic acid, cleavage by a 5' nuclease will be reduced compared to the same probe hybridized to it matched target sequence. Thus, for these enzymes, the use of probes having 12 or fewer bases complementary to the target nucleic acid in the analyte-specific portion of the probe provides significant advantages over the use of probes of more conventional design, when one of these enzymes is used in the cleavage reaction.

Probes comprising short analyte-specific regions have been used in certain embodiments of invasive cleavage assays, e.g. INVADER assays. See, e.g., U.S. Pat. No. 5,985,557, to Prudent et al. However, in view of long-established rules for probe design for real time detection methods in amplification reactions such as in PCR, it is surprising that probes having such short ASRs, especially probes lacking duplex stabilizing moieties such as MGBs, can be made to work for real time detection in assays performed at temperatures well above the melting temperatures of the probes. The performance of these probes is especially surprising with respect to reactions such as PCR amplifications, in which the extension of a primer having a higher $T_m$ would be expected to occlude the probe binding site altogether. While not limiting the invention to any particular mechanism of action, in some embodiments an enzyme in the reaction of the present invention, e.g., a FEN-1 enzyme, may stabilize the footprint probe-target duplex, such that short probes can anneal before extension of a primer occludes the binding sites, and can be used at temperatures that exceed their melting temperatures by several degrees or more.

As discussed in the Background section, one commonly used method for real time detection in PCR is the use of fluorescently labeled analyte-specific hydrolysis probes in the reaction. In the most commonly used methods, a polymerase is used that includes a 5' nuclease "nick translation" activity (e.g., Taq DNA polymerase) and cleavage of the probe occurs as the polymerase extends the PCR primer and encounters the hybridized probe (see, e.g., U.S. Pat. No. 5,210,015, and Holland et al., Proc. Natl. Acad. Sci. USA 88:7276 (1991)). In some types of 5' nuclease PCR reactions, the polymerase and 5' nuclease are provided as separate proteins (e.g., Pfu DNA polymerase and Pfu FEN-1 endonuclease). In the latter configuration, the polymerase extends the primer to the point where the probe is partially displaced so as to create a structure recognized by a FEN-1 enzyme and the probe molecule is then cleaved by the FEN-1 (see, e.g., U.S. Pat. Nos. 6,528,254 and 6,548,250, FULLVELOCITY Q-PCR Master Mix Instruction Manual Revision #114005, Stratagene Corp., FULLVELOCITY QRT-PCR Master Mix Instruction Manual Revision # Revision #114005, Stratagene Corp.).

In both methods described above, it is considered imperative in the assay design that the hydrolysis probe be annealed to the target strand before the primer is extended. For this reason, hydrolysis probes for use in these real time PCR methods (including FULLVELOCITY methods) are selected to bind to the target nucleic acid more stably (i.e., with a higher melting temperature, or $T_m$) than the primers used in the amplification reaction. See, e.g., U.S. Pat. No. 5,210,015, Primer Express® oligo design software from Applied Biosystems, Stratagene's "Introduction to Quantitative PCR" Methods and Applications Guide, IN #70200-00/Revision #084001 Copyright 2004 by Stratagene.

In some real time PCR assay designs, the stability of the probe is ensured by selecting an analyte-specific probe sequence having length and sequence composition selected to have a $T_m$ of above that of the primers. In other assay designs, shorter probes are used, but the melting temperature of the probe is raised by attachment to the probe of a duplex stabilizing moiety. In particular, moieties that bind duplex DNA, such as minor groove binders ("MGBs") (see, e.g., U.S. Pat. No. 6,312,894, Kutyavin, et al., Nucleic Acids Research, 2000, Vol. 28, No. 2 655-661, and ABI Primer Express manual, supra) are commonly used on hydrolysis probes for use in real time PCR. Conjugation of an MGB to an oligonucleotide dramatically increases the stability of the hybrid formed between the oligonucleotide and its target (see, e.g., U.S. Pat. No. 6,312,894, Kutyavin, et al., supra). Increased stability (i.e., increased degree of hybridization) is manifested in a higher melting temperature of hybrid duplexes formed by such MGB-oligonucleotide conjugates, compared to those formed by an unconjugated oligonucleotide of identical length and sequence. This effect is particularly pronounced for short oligonucleotides (e.g., less than about 21 nucleotides in length), and allows such conjugated short oligonucleotide probes, down to about 12 nucleotides, meet the design imperatives of homogenous 5' nuclease PCR assays, i.e., to bind the target nucleic acid more stably than the primers.

The Primer Express Software Version 3.0 "Getting Started" guide for designing probes and primers for real time PCR detection based on the TAQMAN 5' nuclease probe cleavage assay instructs that probes should always have a higher $T_m$ than the primers. For example, a standard (non-MGB) probe is taught as optimally having a $T_m$ of between 68° C. to 70° C., while the primers are taught as optimally having $T_m$s of between 58° C. to 60° C. When an MGB is used on the probe (e.g., for allelic discrimination), the manual instructs that a probe $T_m$ of 65° C. to 67° C. should be used with primers having $T_m$s of between 58° C. to 60° C. With or without a stabilizing MGB, the manual instructs that a probe used in real time 5' nuclease assay detection should have a $T_m$ at least 5 to 10° C. higher than the $T_m$s of the primers it is to be used with. For assays in which the polymerase and 5' nuclease cleavage activities are provided as separate enzymes, the recommendation is the same (see, e.g., FULLVELOCITY Q-PCR and QRT-PCR Master Mix Instruction Manuals, supra).

As discussed above, the present invention provides improved real time detection assays comprising hydrolysis probes having short analyte-specific regions selected to provide the minimal footprint duplex, e.g., for a FEN-1 enzyme. In contrast to the hydrolysis probes typically used in TAQMAN assays and FULLVELOCITY methods, the footprint probes of the present invention are selected to provide the shortest length of probe/target duplex that permits suitable performance of the FEN-1 enzyme in the reaction. The footprint probes of the present invention have melting temperatures substantially below that of the PCR primers with which they are used. In some preferred embodiments, the probes have analyte-specific portions of 12 or fewer nucleotides. Although labels and other such components may influence the stability of a probe/target duplex, in particularly preferred embodiments, the probes of the I, nstant invention do not contain a non-nucleic acid moiety provided for the purpose of increasing the stability of the duplex (e.g., a minor groove binder).

Figure 4:
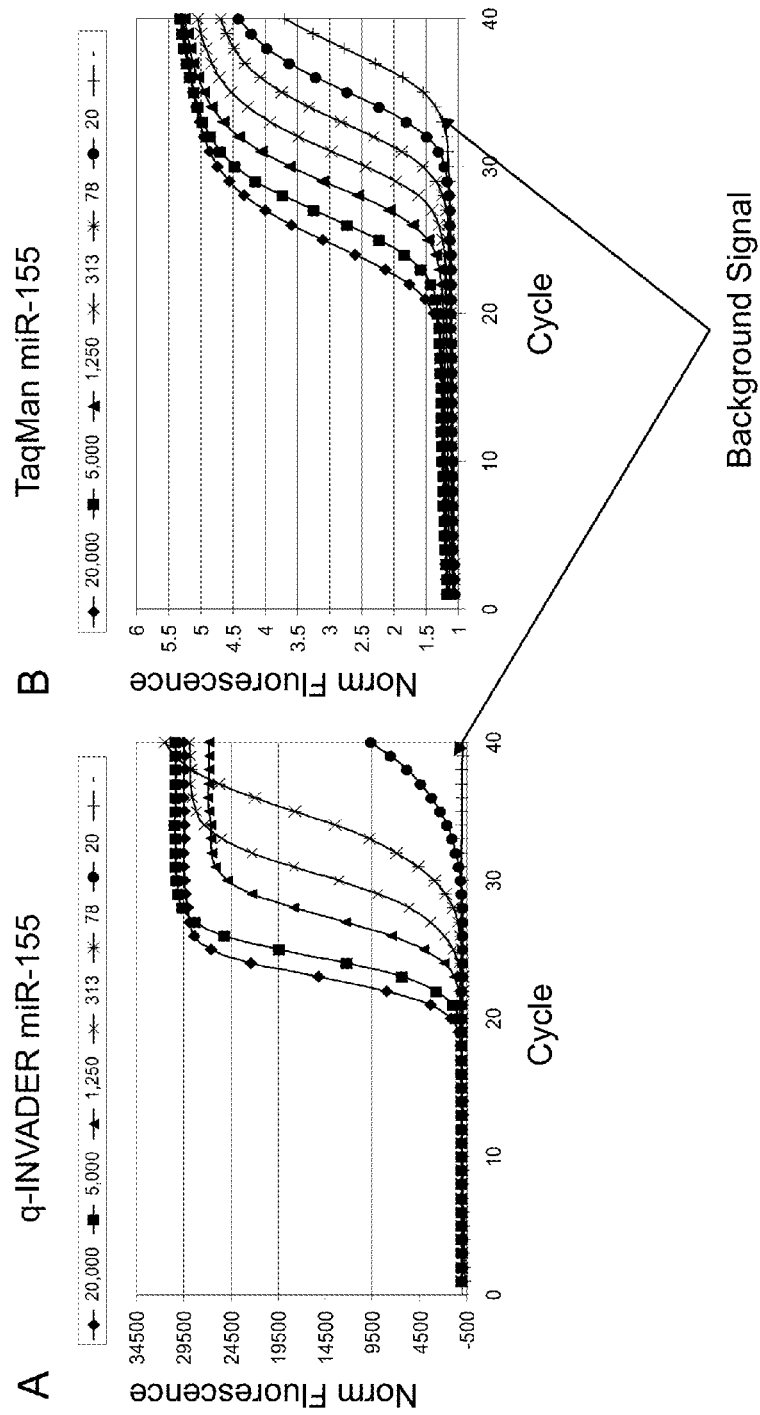
FIGS. 4A and 4B compare results using either the real time PCR+invasive cleavage using a footprint probe (Panel A) with a TAQMAN assay (Panel B) for detection of miR 155 microRNA. These data demonstrate that signal accumulation is faster in the PCR+invasive cleavage assays, and that background in a no-target control starts to appear in the TAQMAN assays but not in the reactions using the footprint probes. Reactions were performed as described in Example 3.

The examples provided herein demonstrate that the short footprint probes of the instant invention provide clean signal during real time PCR detection, with little background (e.g., little accumulation of signal in no-target controls; see, e.g., FIG. 4).

Assays Providing Faster Detection

Another aspect of the present invention is to provide faster real time detection of amplification reactions, when compared to standard hydrolysis probe-based methods. As discussed above, TAQMAN-type assays cleave hydrolysis probes as a primer is extended along a target in a cycle of PCR. Thus, the rate of signal accumulation is tied to, and limited by, the temperature cycling of the PCR.

Assays have been described that provide a secondary cleavage event that is enabled by cleavage of the hydrolysis probe during PCR. See, e.g., U.S. Pat. No. 6,893,819, in which a 5' flap from a hydrolysis probe, once cleaved, is used as a primer in a detection reaction. The flap-primer is extended to form a second cleavage structure comprising another probe, to release another flap, and so on. However, in such an assay, the cleavage product from the original hydrolysis event, the 5' flap, is consumed in the second reaction and does not contribute to additional reactions.

An aspect of the present invention is to provide detection assays in which the accumulation of detectable signal is not dependent on or limited by the thermal cycling of the concurrent PCR assay. For example, in preferred embodiments of the present invention, a cleavage product is release from the analyte-specific probe when it is annealed to the target strand, and the cleavage product then participates in the formation of many subsequent cleavage structures, e.g., with FRET cassettes as depicted in FIG. 1. In some embodiments, the initial cleavage product is not further altered during cleavage of the second and subsequent cleavage structures, while in other embodiments, any alteration of the initial cleavage product (e.g., further cleavage, primer extension) does not prevent the altered initial cleavage product from participating in the formation of second and subsequent cleavage structures.

In particularly preferred embodiments, the second and subsequent cleavage structures are configured such that they can form and dissociate without reliance on the PCR temperature cycling, such that many cleavage structures can form and be cleaved at all times that the temperature of the reaction is within the range at which at least some of the detection cleavage structures can form. When so configured, many copies of the detection cleavage structure may be cleaved for each copy of the initial cleavage product, even as the temperature of the reaction moves through the thermal cycles of the concurrent PCR. In this way, the signal amplification from the detection assay will accumulate more rapidly than accumulation of the amplicon, and more rapidly than is possible with standard hydrolysis probe cleavage, or with secondary detection assays in which the initial cleavage product is consumed rather than re-used. Rapid signal accumulation allows more sensitive detection, and earlier time-to-result.

Assays Providing Lower Costs

As noted above, one of the primary disadvantages of probe-based specific detection chemistries for real time PCR is the need to use different custom probes comprising expensive dyes, quenchers and, optionally, MGBs, for each different analyte sequence. In some embodiments, present invention provides real time detection methods that comprise use of an analyte-specific probe that is unlabeled, coupled with a secondary detection reaction using labeled oligonucleotides, such that the need to produce analyte-specific probes labeled with expensive moieties is avoided.

Assays Providing Improved Dynamic Range

The methods of the present invention are not limited by the type of target nucleic acid. For example, the target nucleic acid may include, for example, nucleic acid material prepared from viruses having an RNA genome. Typically, the RNA target sequence will be converted to a cDNA molecule through the action of a reverse transcriptase, and then detected by the nucleic acid detection assay. Incorporation of the methods of the present invention will increase the dynamic range of detection of RNA target sequences to a breadth not previously feasible.

In some embodiments, the target sequence is a synthetic sequence. For example, a fragment generated in an enzymatic reaction (e.g., a restriction fragment, a cleaved flap from an invasive cleavage reaction, etc.) can be considered a target sequence. In some such embodiments, the detection of such a molecule indirectly detects a separate target nucleic acid from which the synthetic sequence was generated. For example, in an invasive cleavage reaction, a cleaved flap from a primary reaction may be detected with first and second probes that are FRET cassettes. The FRET cassettes differ in some characteristic (e.g., length, etc.) such that the cleaved flap differentially hybridizes to the first and second probes. By using both FRET cassettes (or a third, fourth, etc.), the dynamic range of the reaction is improved.

In some embodiments, the methods of the invention are used in conjunction with methods to further increase the dynamic range of detection. See, e.g., U.S. patent application Ser. No. 11/338,244, which is incorporated here by reference. For example, in some embodiments, the present invention is used in conjunction with methods that achieve greater dynamic range of detection through the use of differential levels of amplification of regions of a target nucleic acid (e.g., no amplification, linear amplification at one or more efficiencies, and/or exponential amplification at one or more efficiencies). In some embodiments, the present invention is used in conjunction with methods that achieve greater dynamic range of detection through the use of probes with different hybridization properties to one or more analyte-specific regions of a target nucleic acid or target nucleic acids. In some preferred embodiments, the different probes have different ASRs, to provide a range of optimal and/or sub-optimal footprints, e.g., for cleavage by a detection reagent. In preferred embodiments, combinations of two or more of the methods are employed. For example, in some preferred embodiments, two or more probes (e.g., three, four, etc.) are contacted with first and second amplicons obtained via different levels of amplification. In some such embodiments, each probe generates the same type of signal so that one simply detects total signal generated by the reactions. The collective signal permits detection of target nucleic acid over a broad dynamic range. For example, experiments conducted during the development of the present invention have demonstrated the ability to detect target nucleic acid from samples differing in over eight logs of copy number of target nucleic acid originally present in the sample.

The compositions, methods, systems, and kits of the invention are useful for the detection and quantitation of a wide variety of nucleic acid targets. The compositions and methods of the present invention are particularly useful for the quantitation of viral target nucleic acids (e.g., viral pathogens). Exemplary viral nucleic acids for which a clinical or research need for the detection of a large range of viral concentrations (e.g., viral load) include, but are not limited to, human immunodeficiency virus (HIV) and other retroviruses, hepatitis C virus (HCV), hepatitis B virus (HBV), hepatitis A virus (HAV), human cytomegalovirus, (CMV), Epstein bar virus (EBV), human papilloma virus (HPV), herpes simplex virus (HSV), Varicella Zoster Virus (VZV), bacteriophages (e.g., phage lambda), adenoviruses, and lentiviruses. In other embodiments, the compositions and methods of the present invention find use in the detection of bacteria (e.g., pathogens or bacteria important in commercial and research applications). Examples include, but are not limited to, *Chlamydia* sp., *N. gonorrhea*, and group B *streptococcus*.

The quantitation of target nucleic acids using the methods and compositions of the present invention are utilized in a variety of clinical and research applications. For example, in some embodiments, the detection assays with increased dynamic range of the present invention are utilized in the detection and quantitation of viral pathogens in human samples. The detection assays of the present invention are suitable for use with a variety of purified and unpurified samples including, but not limited to, urine, stool, lymph, whole blood, and serum. In preferred embodiments, the detection assays of the present invention are suitable for use in the presence of host cells.

In other embodiments, the detection assays of the present invention find use in research applications including, but not limited to, drug screening (e.g., for drugs against viral pathogens), animal models of disease, and in vitro quantitation of target nucleic acid (e.g., bacterial, viral, or genomic nucleic acids).

The probe oligonucleotides of the present invention find use in a variety of nucleic acid detection assays including, but not limited to, those described below. It should be understood that any nucleic acid detection method that employs hybridization can benefit from the systems and methods of the present invention.

EXPERIMENTAL

In the disclosure that follows, the following abbreviations apply: Ex. (Example); Fig. (Figure); ° C. (degrees Centigrade); g (gravitational field); hr (hour); min (minute); olio (oligonucleotide); rxn (reaction); vol (volume); w/v (weight to volume); v/v (volume to volume); BSA (bovine serum albumin); CTAB (cetyltrimethylammonium bromide); HPLC (high pressure liquid chromatography); DNA (deoxyribonucleic acid); p (plasmid); μl (microliters); ml (milliliters); ng (nanograms); μg (micrograms); mg (milligrams); M (molar); mM (milliMolar); μM (microMolar); pmoles (picomoles); amoles (attomoles); zmoles (zeptomoles); nm (nanometers); kdal (kilodaltons); OD (optical density); EDTA (ethylene diamine tetra-acetic acid); FITC (fluorescein isothiocyanate) FAM (fluorescein); SDS (sodium dodecyl sulfate); NaPO4 (sodium phosphate); NP-40 (Nonidet P-40); Tris (tris(hydroxymethyl)-aminomethane); PMSF (phenylmethylsulfonylfluoride); TBE (Tris-Borate-EDTA, i.e., Tris buffer titrated with boric acid rather than HCl and containing EDTA); PBS (phosphate buffered saline); PPBS (phosphate buffered saline containing 1 mM PMSF); PAGE (polyacrylamide gel electrophoresis); Tween (polyoxyethylene-sorbitan); Red or RED (REDMOND RED Dye, Epoch Biosciences, Bothell Wash.) Z28 (ECLIPSE Quencher, Epoch Biosciences, Bothell, Wash.); Promega (Promega, Corp., Madison, Wis.); Glen Research (Glen Research, Sterling, Va.); Coriell (Coriell Cell Repositories, Camden, N.J.); Third Wave Technologies (Third Wave Technologies, Madison, Wis.); Microsoft (Microsoft, Redmond, Wash.); Qiagen (Qiagen, Valencia, Calif.).

The following examples are provided in order to demonstrate and further illustrate certain preferred embodiments and aspects of the present invention and are not to be construed as limiting the scope thereof.

Example 1

Use of Footprint Probes in an INVADER Assay During PCR

This example describes a quantitative assay composed of a combination of an INVADER assay and PCR. The INVADER assay is conducted with footprint probes that have short analyte-specific regions (e.g., 11 to 12 bases). The use of such the short enzyme footprint probes of the invention allows an increased dynamic range for the combined INVADER-PCR assay. While not limited to any specific mechanism, and while not necessary to practice the invention, it is believed that the use of probes with short analyte-specific regions in an invasive cleavage assay such as the INVADER assay allows for an increased dynamic range of target detection, since the cleaved probes do not interfere with the PCR reaction. For example, it is believed that the cleaved probes, since they are short, 1) are not stably hybridized and therefore do not inhibit PCR primer extension, and 2) and do not get extended improperly as part of the PCR reaction.

In this Example, the following six targets were employed: miR-21; miR-126; miR-21; miR-155; U6 RNA; and U24 RNA. The following 10x Oligo mixes were used for each target: reverse primer at 4 uM; forward primer at 4 uM; primer-stacker at 4 uM; probe oligo at 5 uM; and FRET oligo at 2.5 uM. The following 10x reaction buffer was used for each reaction: 100 mM MOPS, pH 7.5; 75 mM $MgCl_2$; and 250 uM dNTP. A 40x enzyme mix was also used for each reaction, which was composed of: 200 ng/ul Afu FEN-1 endonuclease; 1.33 units/ul Go Taq Polymerase; 80 units/ul MMLV reverse Transcriptase; and 7 mM DTT.

The specific probes, primers, invasive oligonucleotides, and FRET cassette sequences for each target are as shown in FIG. 11. Specifically, FIG. 11A shows the oligonucleotide sequences for amplifying and detecting the human miR-21 target; FIG. 11B shows the oligonucleotide sequences for amplifying and detecting the human miR-155 target; FIG. 11C shows the oligonucleotide sequences for amplifying and detecting the human miR-126 target; FIG. 11D shows the oligonucleotide sequences for amplifying and detecting the human U6 snRNA target; and FIG. 11E shows the oligonucleotide sequences for amplifying and detecting the human U24 snRNA target. In regard to FIG. 11A, as an example, the identity of the sequences is as follows: probe (SEQ ID NO:1); miR-21 target sequence (SEQ ID NO:2); forward primer (SEQ ID NO:3); reverse primer/invasive oligonucleotide (SEQ ID NO:4); primer-stacker (SEQ ID NO:5); and FRET cassette sequence (SEQ ID NO:6). In regard to the primer-stacker (SEQ ID NO:5 shown in FIGS. 11A-C), this sequence serves to stabilize the RT-primer/microRNA hybrid. In general, without this sequence, the level of detection may drop dramatically (~100 fold). It is noted that rather than a primer-stacker, one could employ a reverse primer that loops back on itself forming a hairpin at its 5'-end.

The reactions were set up as follow. A premix of each miRNA target was made at 1 pM and a premix of the U6 and U24 RNA targets was made at 5 pM. Next, aliquot duplicates of 10 uL of targets at 1x concentrations and 5x dilutions were made into a 96 well plate. Next was added 10 ul of tRNA no-target control (20 ng/ul tRNA) for each oligo mix to be tested. Then, a reaction mix was added to each well, where the reaction mix was composed of the following components: 2 ul of 10x Oligo mix, 2 ul of 10x reaction buffer; 0.5 ul of 40x enzyme mix; and 5.5 ul of water. Finally, the plate was spun for 30 seconds at 1200 rpm, and was then placed in real time PCR thermocycler programmed for: 42° C.-30 min; 95° C.-2 min; and 40 cycles of (95° C.-20 seconds-->50° C.-45 seconds-->60° C.-30 seconds). Data collection was set for end of each 50° C.-45 seconds step.

Figure 12D:
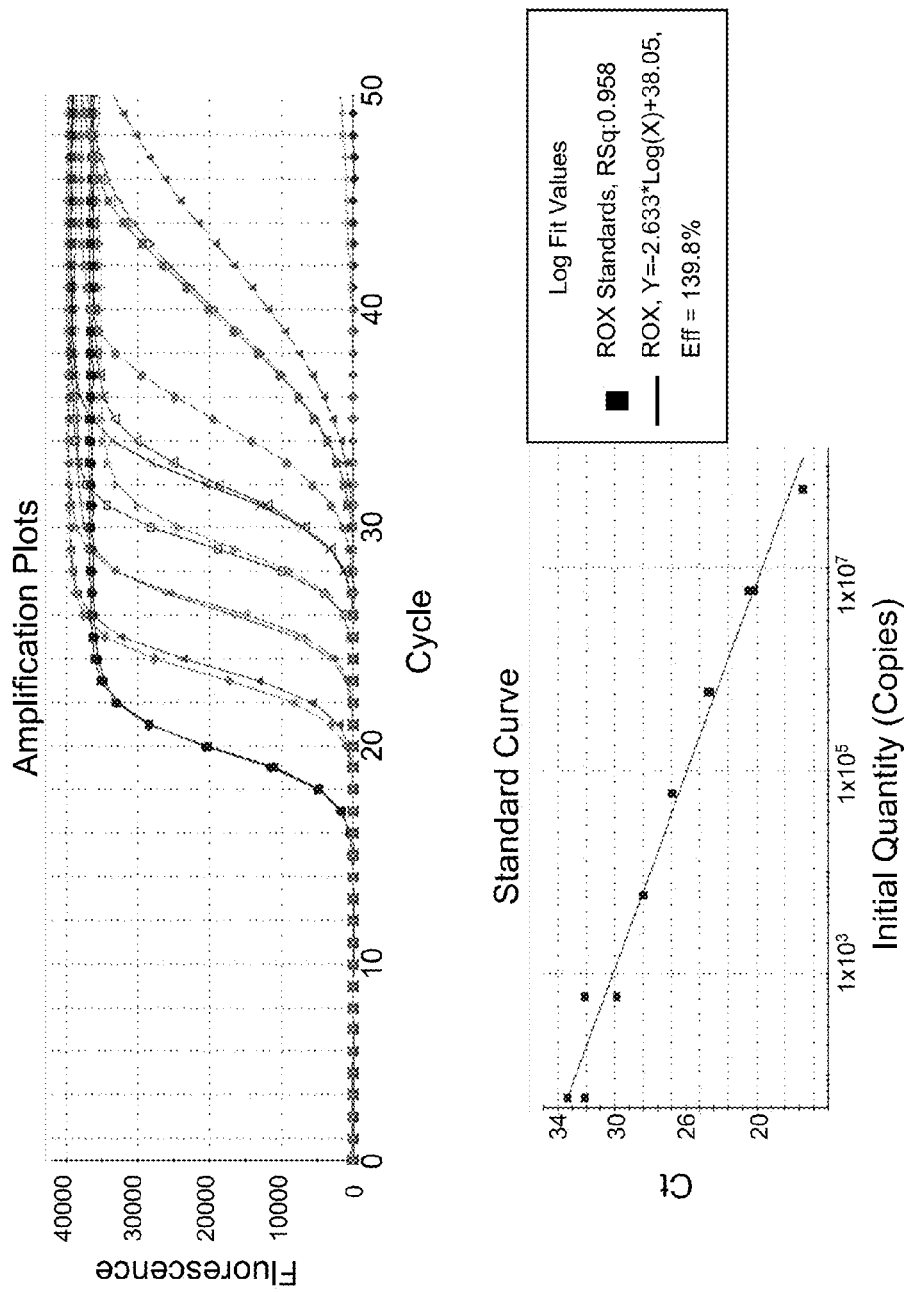
Figure 12E:
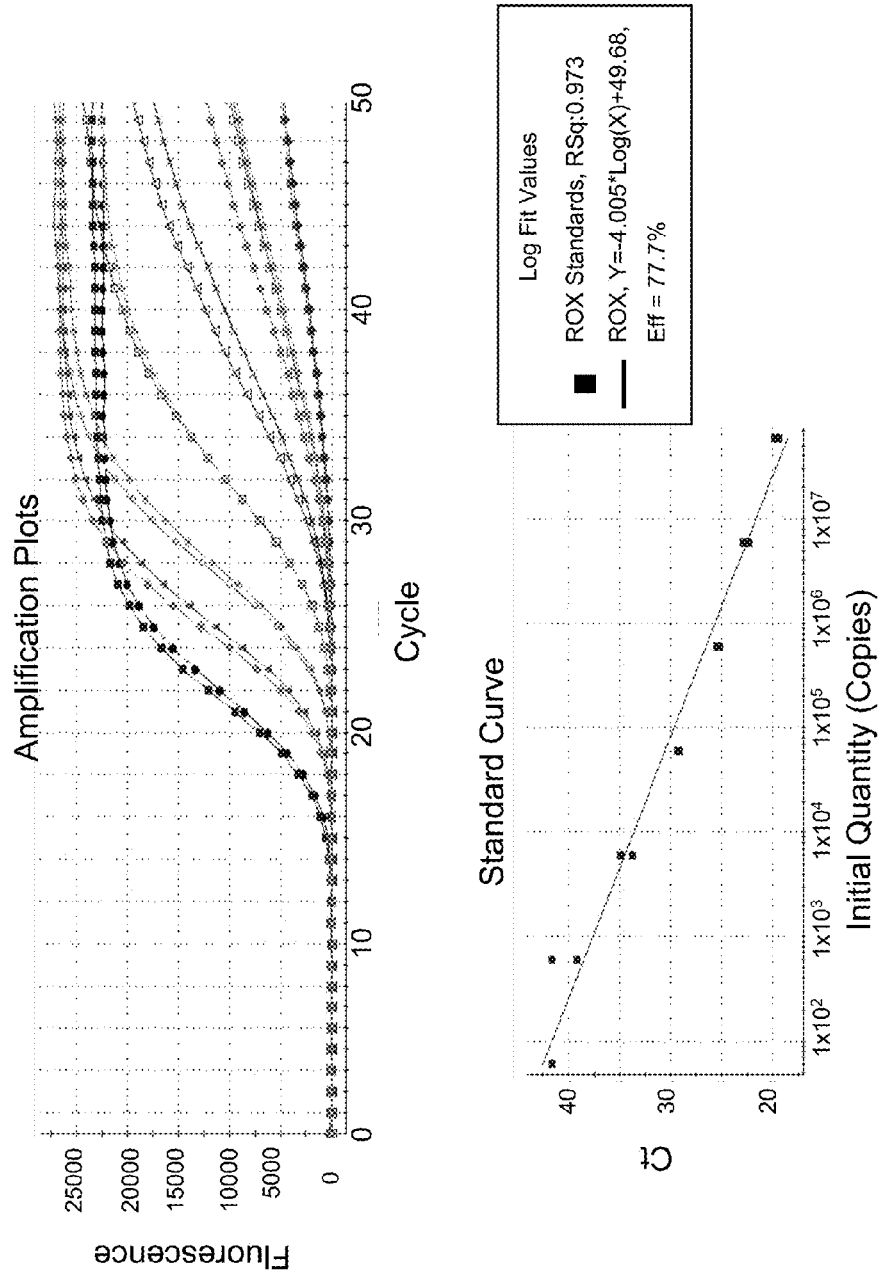

Data was plotted as fluorescence versus cycle number as shown in FIGS. 12A-E. For each target, a threshold was assigned that gave the most linear fit of copy number versus cycle threshold (see bottom panel in each figure). The results for each target are shown in the following figures: miR-155 (FIG. 12A); miR-21 (FIG. 12B); miR-126 (FIG. 12C); U6 (FIG. 12D); and U24 (FIG. 12E). These data show facile and rapid detection of the target RNAs over a wide range of initial target numbers using the methods of the present invention.

Example 2

Effect of Various Components of the PCR-Invasive Cleavage Reaction

This example describes the same type of PCR-Invasive Cleavage Reactions as Example 1, except certain components are left out, or included, to test the various components of the assay. In this Example, the following targets were employed: U6 RNA; GA-21-DNA; Factor V DNA; and Factor II DNA. 10x oligo mixer were generated for each target as follows: reverse primer at 4 uM; forward primer at 4 uM; invasive Oligo at 0.4 uM (omitted for certain conditions as indicated); probe oligo at 6.7 uM; and FRET oligo at 2.5 uM. A 10× reaction buffer was used for reaction which had the following makeup: 100 mM MOPS, pH 7.5; 75 mM MgCl$_2$; and 250 uM dNTP (omitted for certain conditions as indicated). A 40× enzyme mix was also employed, which was composed of the following components: 200 ng/ul Afu FEN-1 (omitted for certain conditions as indicated); 1.33 units/ul GoTaq Polymerase (native Taq DNA polymerase, Promega Corp.); 80 units/ul MMLV reverse Transcriptase (omitted for DNA targets); and 7 mM DTT.

The specific probes, primers, invasive oligonucleotides, and FRET cassette sequences for each target are as shown in FIG. 13. Specifically, FIG. 13A shows the oligonucleotide sequences for amplifying and detecting the U6 DNA target; FIG. 13B shows the oligonucleotide sequences for amplifying and detecting the factor V DNA target; FIG. 13C shows the oligonucleotide sequences for amplifying and detecting the factor II DNA target; FIG. 13D shows the oligonucleotide sequences for amplifying and detecting the GA-21-R DNA target; and FIG. 13E shows the oligonucleotide sequences for amplifying and detecting the human U6 RNA target.

The reactions were set up as follow. A premix was made at 1 nM of synthetic targets or 100 ng of genomic targets. Next, aliquot duplicates of 10 uL of targets at 1× concentrations and 5× dilutions into a 96 well plate were made. A 10 ul mix of tRNA no-target control (20 ng/ul tRNA) was also made for each oligo mix to be tested. To each well, 10 ul of reaction mixture is added to each well, where the reaction mix is composed of the following components: 2 ul of 10× Oligo mix; 2 ul of 10 reaction buffer; 0.5 ul 40× of enzyme mix; and 5.5 ul of water. Next, the plate is spun for 30 seconds at 1200 rpm, then placed in a real time PCR thermocycler programmed for: 95° C.-2 min; and 40 cycles of (95° C.-20 seconds-->50° C.-45 seconds-->60° C.-30 seconds). Data is collected at the end of each 50° C.-45 seconds step.

Data was plotted as fluorescence versus cycle number as shown in FIGS. 14-17. The results for the Factor II target are shown in FIGS. 14A-D. FIGS. 14A-B show the results of this Example with both the invasive oligonucleotide and the FEN-1 enzyme present, while FIGS. 14C-D show the results with the invasive oligonucleotide and FEN-1 enzyme not present. The target level of each well for Factor II is shown in Table 1 below. "Cleavase" as used here refers to Afu FEN-1 endonuclease.

TABLE 1

Factor II: Target Level Per Well

| Well # | | | | Target level (g) |
|---|---|---|---|---|
| 1 | 13 | 25 | 37 | 1.00E−06 |
| 2 | 14 | 26 | 38 | 1.00E−07 |
| 3 | 15 | 27 | 39 | 1.00E−08 |
| 4 | 16 | 28 | 40 | 1.00E−09 |
| 5 | 17 | 29 | 41 | 1.00E−10 |
| 6 | 18 | 30 | 42 | 1.00E−11 |
| 7 | 19 | 31 | 43 | 1.00E−12 |
| 8 | 20 | 32 | 44 | 1.00E−13 |
| 9 | 21 | 33 | 45 | 1.00E−14 |
| 10 | 22 | 34 | 46 | 1.00E−15 |
| 11 | 23 | 35 | 47 | 1.00E−16 |
| 12 | 24 | 36 | 48 | 0.00E+00 |
| Cleavase | + | + | − | − |
| Invasive Oligo | + | + | − | − |

Target is 10X diluted PCR amplicon of FII DNA 35 PCR cycles ~1 ug

Figure 15E:
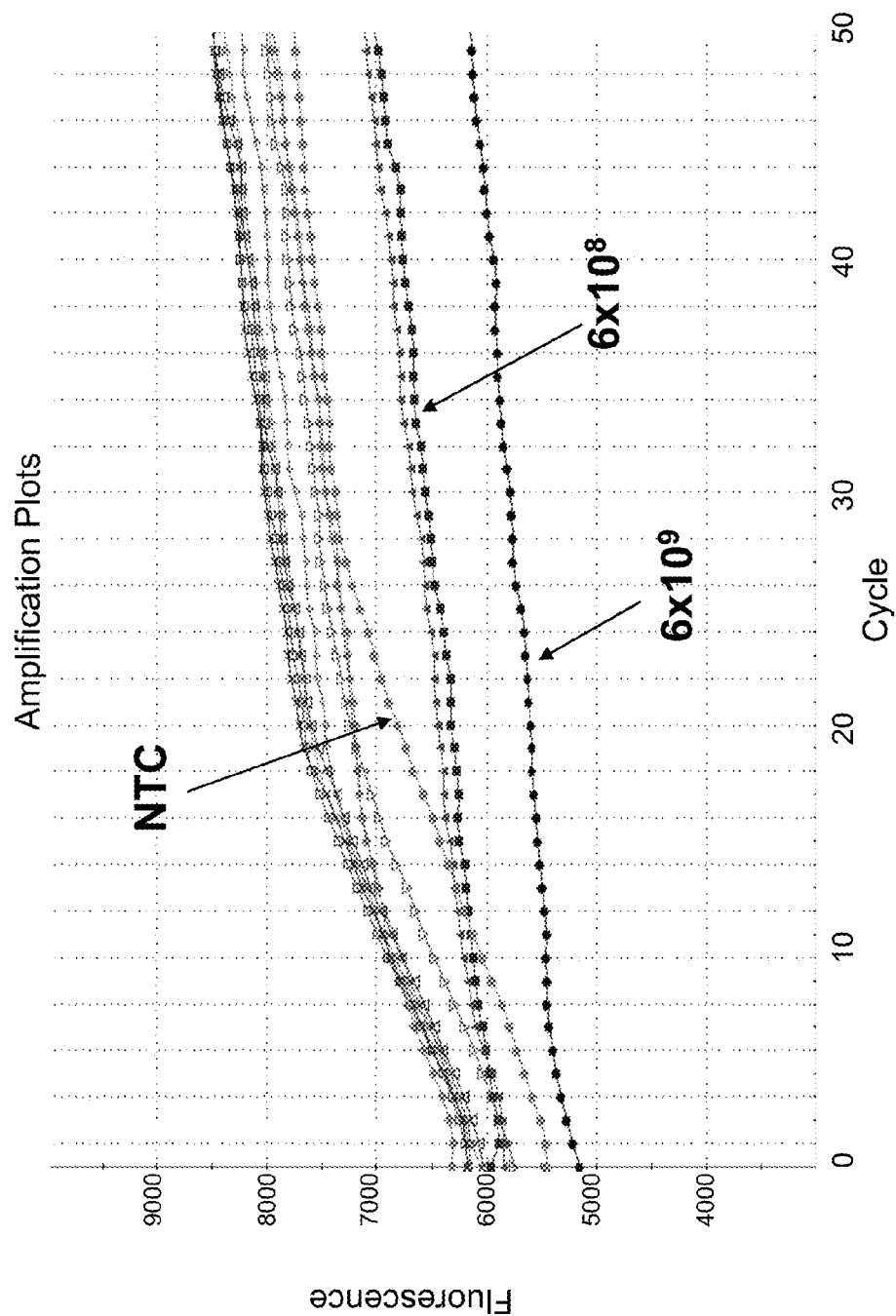
Figure 15F:
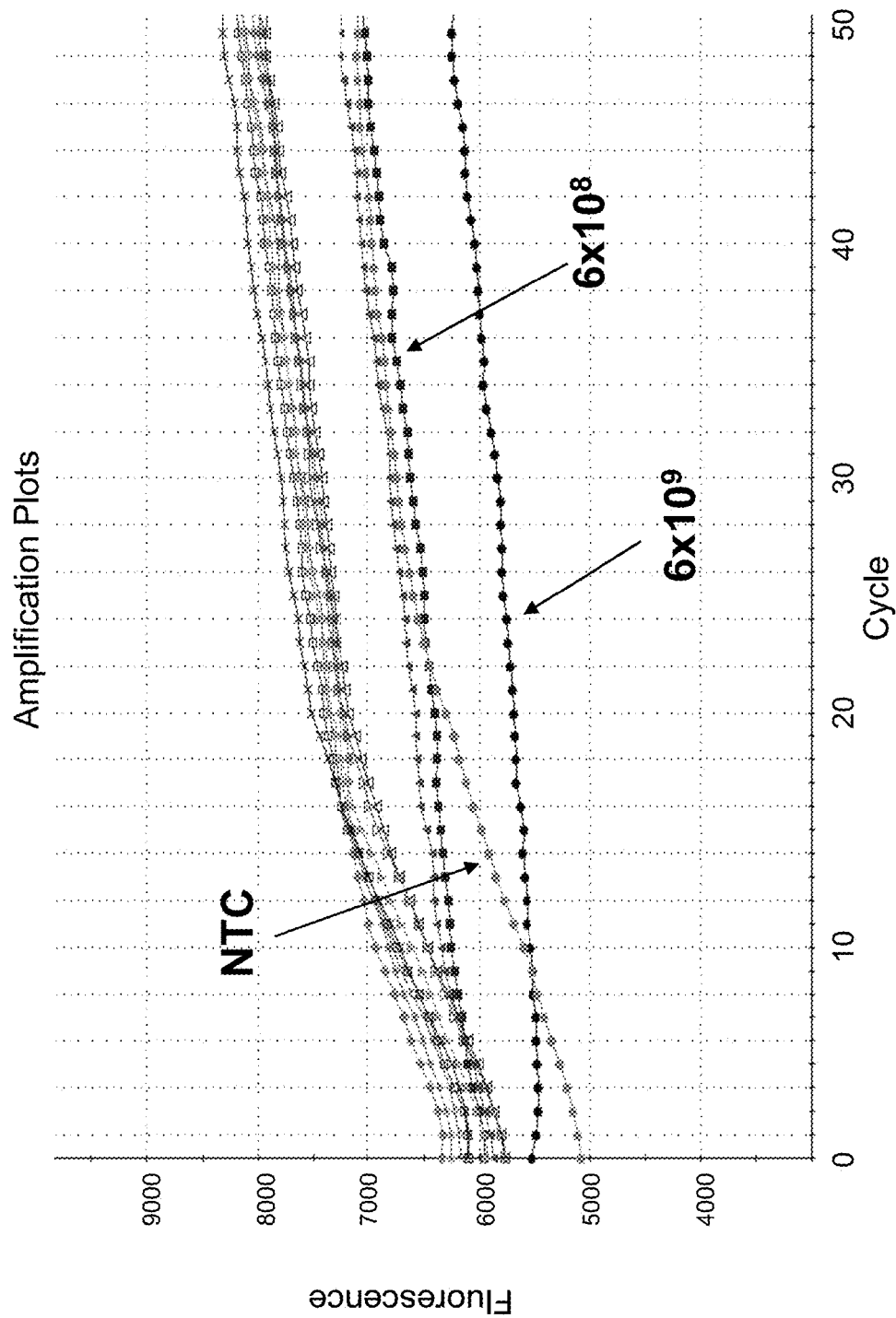

The results for the Factor V target are shown in FIGS. 15A-F. FIGS. 15A-B show the results of this Example with all the reactions components present. FIGS. 15C-D show the results with the invasive oligonucleotide and FEN-1 enzyme not present. FIGS. 15E-F show the same results as FIGS. 15C-D, except the y-axis maximum is 10,000 rather than 60,000.

The results for the corn trans gene GA-21-R target are shown in FIGS. 16A-D. FIGS. 16A-B show the results of this Example with both the invasive oligonucleotide and the FEN-1 enzyme present, while FIGS. 16C-D show the results with the invasive oligonucleotide and FEN-1 enzyme not present. The target level of each well for GA-21-R is shown in Table 2 below.

TABLE 2

GA-21-R Target Number Per Well

| Afu FEN-1 | Invasive Oligo | | 1 | 2 | 3 | 4 | 5 | 6 |
|---|---|---|---|---|---|---|---|---|
| − | − | A | 6.00E+10 | 6.00E+09 | 6.00E+08 | 6.00E+07 | 6.00E+06 | 6.00E+05 |
| − | − | B | 6.00E+10 | 6.00E+09 | 6.00E+08 | 6.00E+07 | 6.00E+06 | 6.00E+05 |
| + | + | C | 6.00E+10 | 6.00E+09 | 6.00E+08 | 6.00E+07 | 6.00E+06 | 6.00E+05 |
| + | + | D | 6.00E+10 Target copies/rxn | 6.00E+09 | 6.00E+08 | 6.00E+07 | 6.00E+06 | 6.00E+05 |

| Afu FEN-1 | Invasive Oligo | | 7 | 8 | 9 | 10 | 11 | 12 |
|---|---|---|---|---|---|---|---|---|
| − | − | A | 6.00E+04 | 6.00E+03 | 6.00E+02 | 6.00E+01 | 6.00E+00 | 0 |
| − | − | B | 6.00E+04 | 6.00E+03 | 6.00E+02 | 6.00E+01 | 6.00E+00 | 0 |
| + | + | C | 6.00E+04 | 6.00E+03 | 6.00E+02 | 6.00E+01 | 6.00E+00 | 0 |
| + | + | D | 6.00E+04 | 6.00E+03 | 6.00E+02 | 6.00E+01 | 6.00E+00 | 0 |

The results for the U6 target are shown in FIGS. 17A-D. FIGS. 17A-B show the results of this Example with both the invasive oligonucleotide and the FEN-1 enzyme present, while FIGS. 17C-D show the results with the invasive oligonucleotide and FEN-1 enzyme not present. The target level of each well for U6 is shown in Table 3 below. "Cleavase" as used here refers to Afu FEN-1 endonuclease.

TABLE 3

U6 RNA Target Number Per Well

| Cleavase | Invasive Oligo | | | | | | | | | | | |
|---|---|---|---|---|---|---|---|---|---|---|---|---|
| − | − | W1 | W2 | W3 | W4 | W5 | W6 | W7 | W8 | W9 | W10 | W11 | W12 |
| − | − | W13 | W14 | W15 | W16 | W17 | W18 | W19 | W20 | W21 | W22 | W23 | W24 |
| + | + | W25 | W26 | W27 | W28 | W29 | W30 | W31 | W32 | W33 | W34 | W35 | W36 |
| + | + | W37 | W38 | W39 | W40 | W41 | W42 | W43 | W44 | W45 | W46 | W47 | W48 |

| Cleavase | Invasive Oligo | U6 Copies per rxn | U6 Copies per rxn | U6 Copies per rxn | U6 Copies per rxn | U6 Copies per rxn | U6 Copies per rxn | U6 Copies per rxn |
|---|---|---|---|---|---|---|---|---|
| − | − | 6.00E+09 | 6.00E+08 | 6.00E+07 | 6.00E+06 | 6.00E+05 | 6.00E+04 | 6.00E+03 |
| − | − | 6.00E+09 | 6.00E+08 | 6.00E+07 | 6.00E+06 | 6.00E+05 | 6.00E+04 | 6.00E+03 |
| + | + | 6.00E+09 | 6.00E+08 | 6.00E+07 | 6.00E+06 | 6.00E+05 | 6.00E+04 | 6.00E+03 |
| + | + | 6.00E+09 | 6.00E+08 | 6.00E+07 | 6.00E+06 | 6.00E+05 | 6.00E+04 | 6.00E+03 |

| Cleavase | Invasive Oligo | U6 Copies per rxn | U6 Copies per rxn | U6 Copies per rxn | U6 Copies per rxn | U6 Copies per rxn |
|---|---|---|---|---|---|---|
| − | − | 6.00E+02 | 60 | 6.0 | 0.6 | — |
| − | − | 6.00E+02 | 60 | 6.0 | 0.6 | — |
| + | + | 6.00E+02 | 60 | 6.0 | 0.6 | — |
| + | + | 6.00E+02 | 60 | 6.0 | 0.6 | — |

In light of the above results, it is clear that essentially no signal is generated when the FEN-1 enzyme and the Invasive oligo are absent, even though the polymerase enzyme comprises a 5' nuclease activity.

Example 3

Use of Short Probes in an INVADER Assay Configured for SNP Detection During PCR This Example describes the use of probes with a short analyte-specific region (12 bases in this Example) in an invasive cleavage assays conducted during PCR for genotyping. The target in this Example is Factor V. The specific probes, primers, invasive oligonucleotides, and FRET cassette sequences for detecting the SNP in Factor V is shown in FIG. 5.

The wild-type and mutant reactions were set up as follows. An aliquot 10 ul of genomic DNA (1 ng/ul) or tRNA no-target control (20 ng/ul tRNA) in placed in a 96 well plate. 10 ul of reaction mixture is added to each well, where the reaction mixtures (as well as the 40× enzyme mix) is as described in Example 1. The 10× oligo mixture, which is part of the reaction mixtures, is composed of the following sequences as shown in Table 4.

TABLE 4

10X Oligo Mixture
10X Q-Invader FV Oligo mix =

| Oligo # | 10X conc (uM) |
|---|---|
| 2749-70-07 | 4 |
| 2749-70-06 | 4 |
| 2749-70-05 | 0.4 |
| 2749-70-04 | 5 |
| 2749-70-03 | 5 |
| Arm 6 FAM FRET | 2.5 |
| Arm 4 Yellow FRET | 2.5 |

The plate was spun for 30 seconds at 1200 rpm, then placed in a real time PCR thermocycler programmed for: 95° C.-2 min; and 50 cycles of (95° C.-20 seconds-->52° C.-60 seconds). Data was collected at the end of each 52° C.-45 seconds step.

Figure 6:
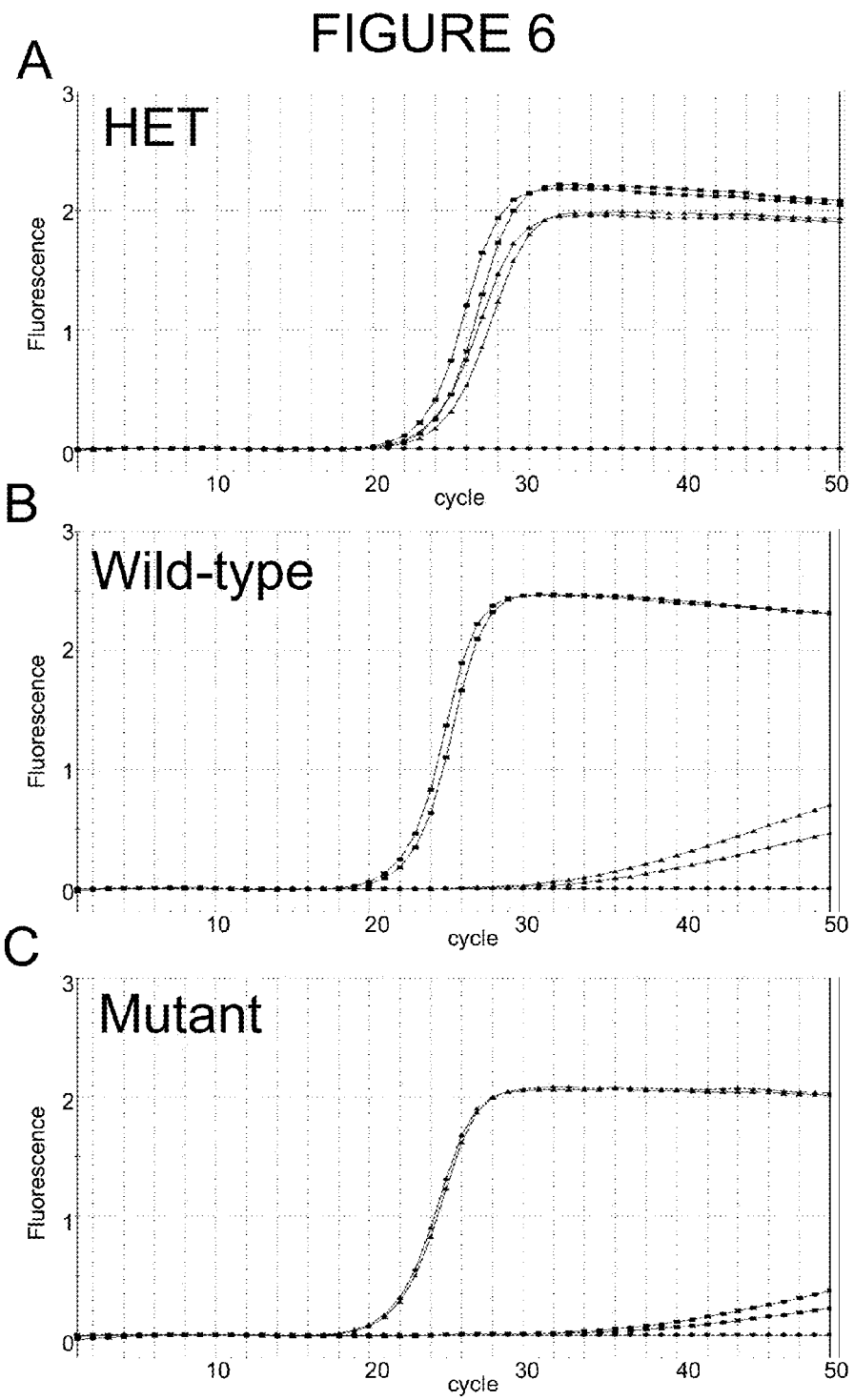
FIGS. 6A-F compare the results of PCR+invasive cleavage assays using the assay designs shown in FIG. 8, with genotyping of the same alleles using the TAQMAN assay.
Figure 6:
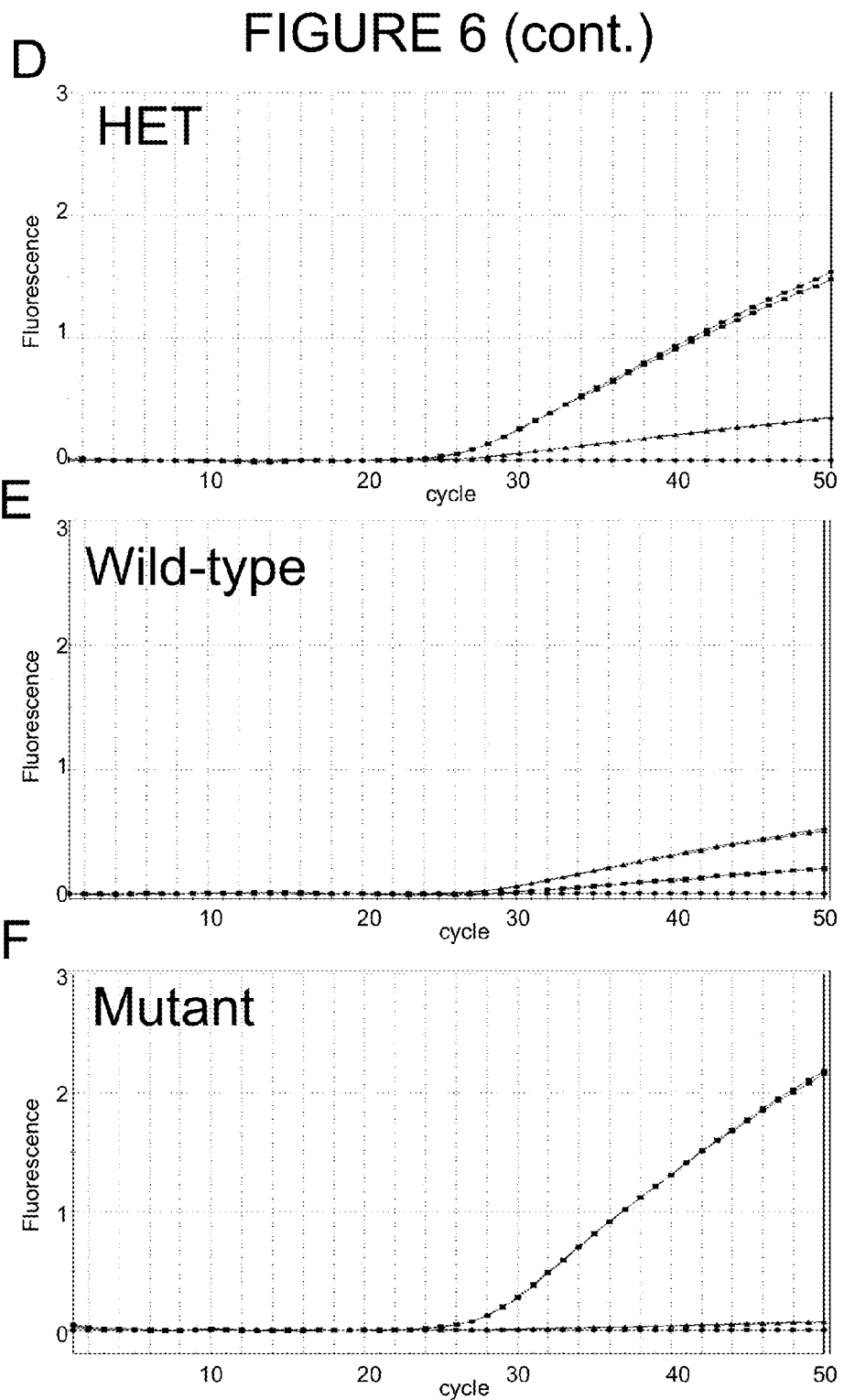

Data is plotted as fluorescence data versus cycle, as shown in FIG. 6. The results for the mutant target detection are shown in FIG. 6A, the results for the wild-type target detection are shown in FIG. 6B, and the results for heterogenous target detection are shown in FIG. 6C. For each target, a cycle threshold (Ct) that gives the least cross reactivity for each genotype is assigned. Data for detection of the same alleles using the TAQMAN assay as described in Luderer, et al., Clinical Chemistry 50, No. 4 (2004):787-788 is shown in FIGS. 6D-6F.

Figure 7:
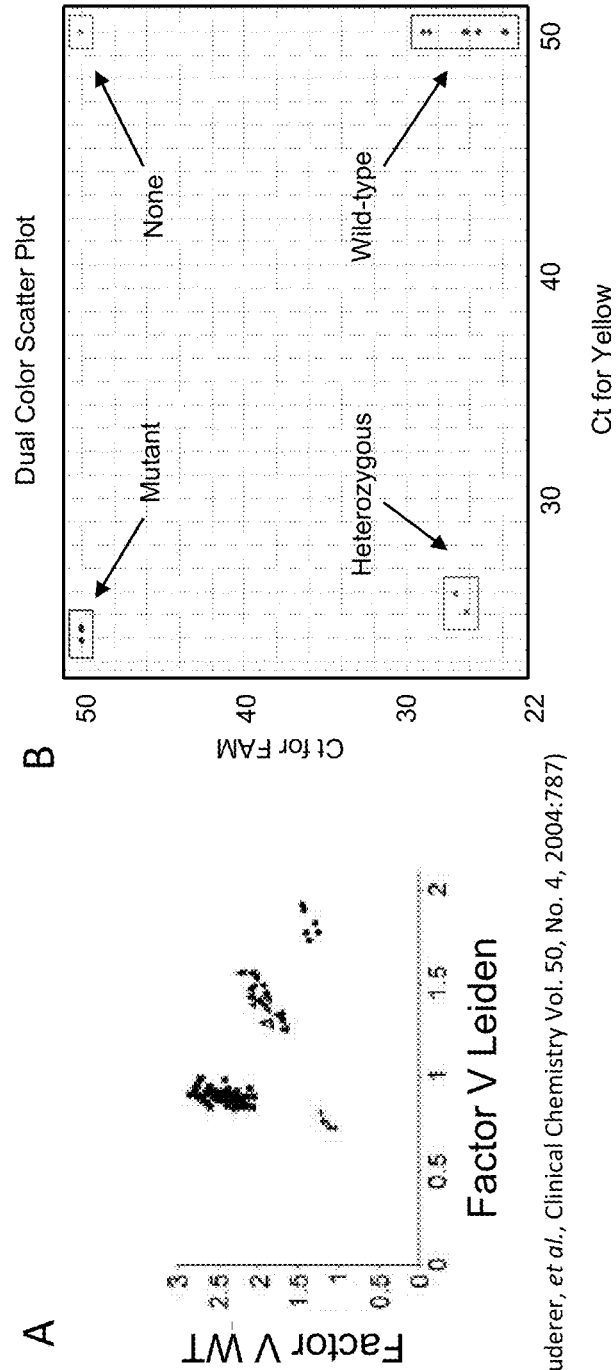
FIGS. 7A and 7B compare scatter plots for SNP detection in the Factor V gene by PCR+invasive cleavage with footprint probes (as described in Example 3)(7B) and by the TAQMAN assay (7A).
Figure 10:
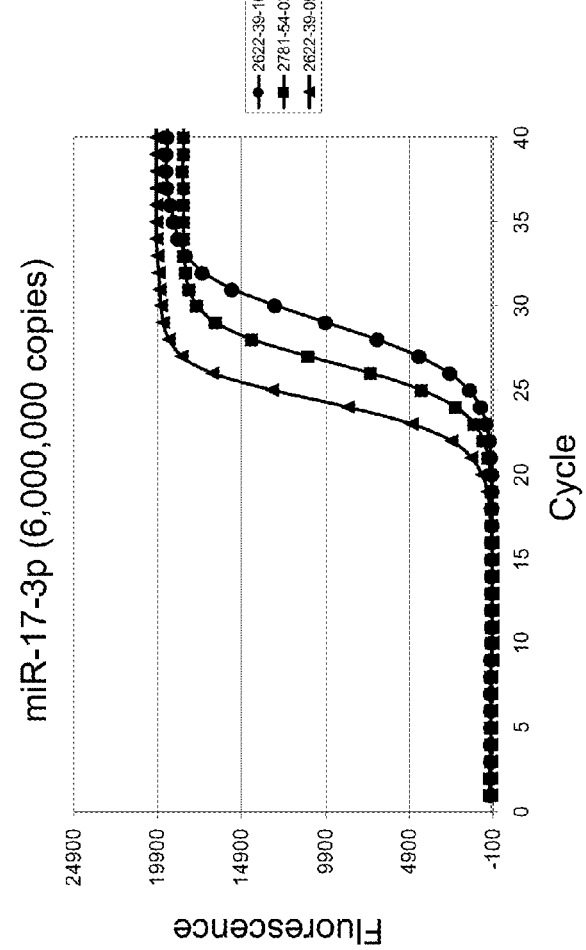
FIGS. 10A-B show results achieved in the detection of hsa-miR-17-3p microRNA with a footprint probe comprising 11 complementary nucleotides in the ASR compared with a footprint probe comprising 11 nucleotides, in which 1 nucleotide is mismatched to the target, and a footprint probe having only 10 nucleotides in the ASR, (using conditions as described in Example 3). Panel A shows a schematic diagram of the test molecules, and panel B shows data from samples having 6×10$^6$ copies of hsa-miR-17-3p microRNA. These examples show that, while having an ASR that is both near the optimal length for a FEN-1 enzyme (e.g., 11 or 12 nucleotides) provides the strongest detection signal, using a probe having an ASR of the proper length but comprising a mismatch provides stronger signal than is achieved using a probe having an ASR that is below the optimal length.

FIG. 7 shows a scatter plot of the data from Luderer, et al. (panel A), compared to a scatter plot of FAM Ct versus Yellow Ct in the PCR+invasive cleavage using foot print probes, as described here (panel B). The genotype is determined based on the Ct dye assignment. In both panels A and B, the mutant is shown in the upper left hand corner of the plot; wild-type is shown in the bottom right hand corner of the plot. In panel A, the heterogeneous result is shown in the upper right, while in panel B, the heterogeneous result is shown in the bottom left hand corner of the plot, and the no-target controls are similarly inverted (lower left for panel A and upper right hand corner of the plot for panel B).

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention should not be unduly limited to such specific embodiments. Indeed, various modifications of the described modes for carrying out the invention which are obvious to those skilled in the relevant arts are intended to be within the scope of the following claims.

We claim:

1. A method of analyzing a target nucleic acid, comprising:
   a) amplifying a target nucleic acid in the presence of a synthetic probe and a thermostable FEN-1 endonuclease under conditions such that said synthetic probe is cleaved during an amplification reaction to generate cleaved fragments;
   wherein said synthetic probe is a footprint probe comprising an analyte-specific portion and a non-target portion, wherein said non-target portion is substantially non-complementary to said target nucleic acid and wherein said analyte-specific portion is no more than 12 nucleotides in length, and contains up to 12 nucleotides that are complementary to said target nucleic acid, and
   wherein, if said amplifying is done in an isothermal reaction, said analyte-specific portion of said footprint probe has a calculated $T_m$ with said target that is at least 5° C. below the temperature at which said isothermal reaction is conducted, or if said amplifying is done in a thermal cycling reaction, said analyte-specific portion of said footprint probe has a calculated $T_m$ with said target that is at least 5° C. below the lowest temperature used in said thermal cycling; and
   b) detecting said cleaved fragments during said amplification reaction.

2. The method of claim 1, wherein, if said amplifying is done in an isothermal reaction, said analyte-specific portion of said footprint probe has a calculated $T_m$ with said target that is at least at least 8° C. below the temperature at which said isothermal reaction is conducted, or if said amplifying is done in a thermal cycling reaction, said analyte-specific portion of said footprint probe has a calculated $T_m$ with said target that is at least 8° C. below the lowest temperature used in said thermal cycling.

3. The method of claim 1, wherein, if said amplifying is done in an isothermal reaction, said analyte-specific portion of said footprint probe has a calculated $T_m$ with said target that is at least at least 10° C. below the temperature at which said isothermal reaction is conducted, or if said amplifying is done in a thermal cycling reaction, said analyte-specific portion of said footprint probe has a calculated $T_m$ with said target that is at least 10° C. below the lowest temperature used in said thermal cycling.

4. The method of claim 1, wherein said synthetic probe is unlabeled.

5. The method of claim 1, wherein said synthetic probe does not contain non-natural nucleotides and/or does not contain a minor groove binder moiety.

6. The method of claim 1, wherein said non-target portion of said synthetic probe is at least 10 nucleotides in length.

7. The method of claim 1, wherein said amplifying employs amplification primer oligonucleotides, and wherein said analyte specific portion of said synthetic probe has a calculated $T_m$ with respect to said target nucleic acid substantially below the calculated $T_m$ of said amplification primer oligonucleotides with which it is used.

8. The method of claim 1, wherein said analyte specific portion of said probe contains no more than 11 nucleotides.

9. The method of claim 1, wherein said analyte specific portion of said probe contains no more than 10 nucleotides.

10. The method of claim 1, wherein said analyte specific portion of said probe contains no more than 9 nucleotides.

11. The method of claim 1, wherein said analyte specific portion of said probe contains no more than 8 nucleotides.

12. The method of claim 1, wherein said analyte specific portion of said probe contains no more than 7 nucleotides.

13. The method of claim 1, wherein said analyte specific portion of said probe contains no more than 6 nucleotides.

14. The method of claim 1, wherein a cleavage structure is formed before said probe is cleaved, wherein said cleavage structure is formed by association of said target nucleic acid with:
   a) said synthetic probe at a first region of said target nucleic acid; and
   b) a second oligonucleotide at a second region of said target nucleic;
   wherein said second region is downstream of said first region of said target nucleic acid.

15. The method of claim 14, wherein said second region of said target nucleic acid is contiguous with said first region.

16. The method of claim 15, wherein in said cleavage structure, at least one nucleotide at the 3' end of said second oligonucleotide overlaps with a region of hybridization between said probe and said target nucleic acid.

17. The method of claim 16, wherein in said cleavage structure, the 3' terminal nucleotide of said second oligonucleotide is not complementary to said target nucleic acid.

18. The method of claim 14, wherein said second oligonucleotide is also a primer oligonucleotide used in said amplifying.

19. The method of claim 1, wherein said detecting said cleaved fragments comprises associating one or more of said cleaved fragments with a synthetic detection oligonucleotide.

20. The method of claim 19, wherein said synthetic detection oligonucleotide comprises a label.

21. The method of claim 1, wherein said cleaved fragments, when associated with said synthetic detection oligonucleotide, form a cleavage structure that is cleavable by said thermostable FEN-1 endonuclease.

* * * * *